United States Patent
Bleicher et al.

(10) Patent No.: US 7,786,128 B2
(45) Date of Patent: Aug. 31, 2010

(54) INDOLE OR BENZIMIDAZOLE DERIVATIVES AS $CB_1$ INVERSE AGONISTS

(75) Inventors: Konrad Bleicher, Freiburg (DE); Matthias Heinrich Nettekoven, Grenzach-Wyhlen (DE); Philippe Pflieger, Schwoben (FR); Stephen Roever, Inzlingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/114,219

(22) Filed: May 2, 2008

(65) Prior Publication Data

US 2008/0234290 A1 Sep. 25, 2008

Related U.S. Application Data

(62) Division of application No. 11/257,885, filed on Oct. 25, 2005, now Pat. No. 7,384,945.

(30) Foreign Application Priority Data

Oct. 27, 2004 (EP) .................................. 04105329

(51) Int. Cl.
A61K 31/415 (2006.01)
A61K 31/40 (2006.01)
A61K 31/497 (2006.01)
A01N 43/52 (2006.01)
A01N 43/38 (2006.01)
C07D 209/42 (2006.01)

(52) U.S. Cl. .................. 514/254.06; 514/394; 514/419; 548/492

(58) Field of Classification Search ........................ None
See application file for complete search history.

(56) References Cited

U.S. PATENT DOCUMENTS

| | | | |
|---|---|---|---|
| 3,940,418 A | 2/1976 | Hamilton | |
| 5,462,960 A | 10/1995 | Barth et al. | |
| 5,596,106 A | 1/1997 | Cullinan et al. | |
| 5,624,941 A | 4/1997 | Barth et al. | |
| 6,355,631 B1 | 3/2002 | Achard et al. | |
| 6,479,479 B2 | 11/2002 | Achard et al. | |
| 6,518,264 B2 | 2/2003 | Achard et al. | |
| 6,566,356 B2 | 5/2003 | Achard et al. | |
| 6,734,176 B2 | 5/2004 | Achard et al. | |
| 6,858,603 B2 | 2/2005 | Achard et al. | |
| 6,872,717 B2 | 3/2005 | Achard et al. | |
| 2001/0027193 A1 | 10/2001 | Achard et al. | |
| 2002/0019383 A1 | 2/2002 | Achard et al. | |
| 2002/0035102 A1 | 3/2002 | Achard et al. | |
| 2003/0055033 A1 | 3/2003 | Achard et al. | |
| 2003/0119810 A1 | 6/2003 | Achard et al. | |
| 2003/0162808 A1 | 8/2003 | Achard et al. | |
| 2004/0116465 A1 | 6/2004 | Cheng et al. | |
| 2004/0157823 A1 | 8/2004 | Achard et al. | |
| 2004/0235816 A1 | 11/2004 | Achard et al. | |
| 2005/0130953 A1 | 6/2005 | Achard et al. | |

FOREIGN PATENT DOCUMENTS

| | | |
|---|---|---|
| EP | 576357 | 3/1997 |
| EP | 656354 | 6/1997 |
| EP | 658546 | 5/2001 |
| FR | 2783246 A1 | 3/2000 |
| FR | 2805810 A1 | 9/2001 |
| FR | 2805817 A1 | 9/2001 |
| FR | 2805818 A1 | 9/2001 |
| WO | WO9602248 | 2/1996 |
| WO | WO9719063 | 5/1997 |
| WO | WO0015609 | 3/2000 |
| WO | WO0046209 | 8/2000 |
| WO | WO0132663 | 5/2001 |
| WO | WO0164632 | 9/2001 |
| WO | WO0164633 | 9/2001 |
| WO | WO0164634 | 9/2001 |
| WO | WO0170700 | 9/2001 |
| WO | WO0228346 | 4/2002 |
| WO | WO03/053938 A1 | 7/2003 |
| WO | WO2004/108712 A1 | 12/2004 |

OTHER PUBLICATIONS

D. Shire, et. al., J. Biol. Chem. 270 (8) (1995) 3726-31.
S. Munro, K.L. Thomas, M. Abu-Shaar, Nature 365 (1993) 61-61).
Y. Gaoni, R. Mechoulam, J. Am. Chem. Soc., 86 (1964) 1646.
R. Mechoulam (Ed.) in "Cannabinoids as therapeutic Agents", 1986, pp. 1-20, CRC Press.

(Continued)

Primary Examiner—James O Wilson
Assistant Examiner—Jeffrey H Murray
(74) Attorney, Agent, or Firm—George W. Johnston; Dennis P. Tramaloni; Samuel H. Megerditchian

(57) ABSTRACT

Provided are compounds of the formula I:

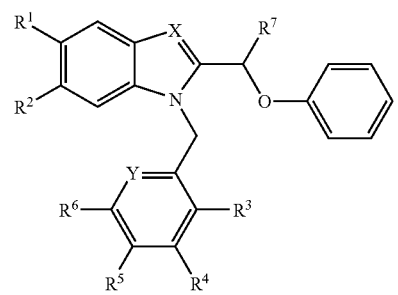

and pharmaceutically acceptable salts thereof, processes for making said compounds and pharmaceutically acceptable salts thereof, pharmaceutical compositions comprising said compound and pharmaceutically acceptable salts thereof, and methods of using said compounds. The compounds are useful for the treatment and/or prophylaxis of diseases which are associated with the modulation of CB1 receptors.

12 Claims, No Drawings

OTHER PUBLICATIONS

R. G. Pertwee, Pharmaceut. Sci. 3 (11) (1997) 539-545.
E. M. Williamson, F. J. Evans, Drugs 60 (6) (2000) 1303-1314.
R.G. Pertwee, Curr. Med. Chem., 6 (8) (1999) 635-664.
W.A. Devane, et. al., Science 258 (1992) 1946-9.
V. Di Marzo,et.al., Trends in Neuroscience 21 (12) (1998) 521-8.
A. C. Porter, C.C. Felder, Pharmacol. Ther., 90 (1) (2001) 45-60.
C.M. Williams, T.C. Kirkham, Psychopharmacology 143 (3) (1999) 315-317.
C. C. Felder, et. al., Proc. Natl. Acad. Sci. U. S. A. 90 (16) (1993) 7656-60.
G. Colombo, et al., Life Sci. 63 (8) (1998) L113-PL117.
F. Barth, et al., *"Cannabinoid antagonists: From research tools to potential new drugs."* Abstracts of Papers, 222nd ACS National Meeting, Chicago, IL, United States, Aug. 26-30, 2001.
Aai; M. Pacheco, et al., J. Pharmacol. Exp. Ther. 257 (1) (1991) 170-183.
WIN54661; F. M. Casiano, et al., NIDA Res. Monogr. 105 (1991) 295-6.
AM630, K. Hosohata, et al., Life Sci. 61 (1997) 115-118.
R. Pertwee, et al., Life Sci. 56 (23-24) (1995) 1949-55.
LY320135, C. C. Felder, et al., J. Pharmacol. Ther. 284 (1) (1998) 291-7.
M. Kanyonyo, et al., Bioorg. Med. Chem. Lett. 9 (15) (1999) 2233-2236.
F. Ooms, et. al., J. Med. Chem. 45 (9) (2002) 1748-1756.
Parker et al., Encyclopedia of Reagents for Organic Synthesis; Sodium Hydroxide (2001).
Deshayeset al., Encyclopedia of Reagents for Organic Synthesis; Sodium Hydroxide (2001).
Radbruch et al., Der Schmerz, 17(4) 274-9, (2003) Abstract in English.

INDOLE OR BENZIMIDAZOLE DERIVATIVES AS $CB_1$ INVERSE AGONISTS

PRIORITY TO RELATED APPLICATIONS

This application is a division of U.S. application Ser. No. 11/257,885, filed Oct. 25, 2005, now pending, which claims the benefit of European Application No. 04105329.9, filed Oct. 27, 2004. The entire contents of the above-identified applications are hereby incorporated by reference.

FIELD OF THE INVENTION

The present invention is directed to novel indole or benzimidazole derivatives, their manufacture, pharmaceutical compositions containing them and their use as medicaments. The active compounds of the present invention are useful in treating obesity and other disorders.

In one embodiment, the present invention relates to compounds of the general formula (I)

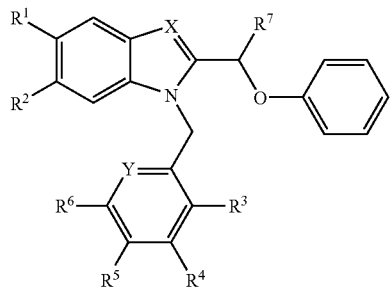

I and all pharmaceutically acceptable salts thereof.

Compounds of formula I of the present invention are modulators of the $CB_1$ receptor.

All documents cited or relied upon below are expressly incorporated herein by reference.

BACKGROUND OF THE INVENTION

Two different subtypes of cannabinoid receptors ($CB_1$ and $CB_2$) have been isolated and both belong to G protein coupled receptor superfamily. An alternative spliced form of $CB_1$, $CB_{1A}$, has also been described, but it did not exhibit different properties in terms of ligand binding and receptor activation than $CB_1$ (D. Shire, C. Carrillon, M. Kaghad, B. Calandra, M. Rinaldi-Carmona, G. Le Fur, D. Caput, P. Ferrara, J. Biol. Chem. 270 (8) (1995) 3726-31). The $CB_1$ receptor is mainly located in the brain, whereas the $CB_2$ receptor is predominately distributed in the periphery primarily localized in spleen and cells of the immune system (S. Munro, K. L. Thomas, M. Abu-Shaar, Nature 365 (1993) 61-61). Therefore in order to avoid side effects a $CB_1$-selective compound is desirable.

$\Delta^9$-tetrahydrocannabinol ($\Delta^9$-THC) is the principal psychoactive compound in the Indian hemp (Y. Gaoni, R. Mechoulam, J. Am. Chem. Soc., 86 (1964) 1646), cannabis sativa (marijuanan), and has medicinal uses (R. Mechoulam (Ed.) in "Cannabinoids as therapeutic Agents", 1986, pp. 1-20, CRC Press). $\Delta^9$-THC is a non-selective $CB_{1/2}$ receptor agonist and is available in the USA as dronabinol (marinol®) for the alleviation of cancer chemotherapy-induced emesis (CIE) and the reversal of body weight loss experienced by AIDS patients through appetite stimulation. In the UK Nabolinone (LY-109514, Cesamet®), a synthetic analogue of $\Delta^9$-THC, is used for CIE (R. G. Pertwee, Pharmaceut. Sci. 3 (11) (1997) 539-545, E. M. Williamson, F. J. Evans, Drugs 60 (6) (2000) 1303-1314).

Anandamide (arachidonylethanolamide) was identified as the endogenous ligand (agonist) for $CB_1$ (R. G. Pertwee, Curr. Med. Chem., 6 (8) (1999) 635-664; W. A. Devane, L. Hanus, A. Breuer, R. G. Pertwee, L. A. Stevenson, G. Griffin, D. Gibson, A. Mandelbaum, A. Etinger, R. Mechoulam, Science 258 (1992) 1946-9). Anandamide and 2-arachidonoylglycerol (2-AG) modulate at the presynaptic nerve terminal negatively adenylate cyclase and voltage-sensitive $Ca^{2+}$ channels and activates the inwardly rectifying $K^+$ channel (V. Di Marzo, D. Melck, T. Bisogno, L. De Petrocellis, Trends in Neuroscience 21 (12) (1998) 521-8), thereby affecting neurotransmitter release and/or action, which decreases the release of neurotransmitter (A. C. Porter, C. C. Felder, Pharmacol. Ther., 90 (1) (2001) 45-60).

Anandamide as $\Delta^9$-THC also increases feeding through $CB_1$ receptor-mediated mechanism. $CB_1$ selective antagonists block the increase in feeding associated with administration of anandamide (C. M. Williams, T. C. Kirkham, Psychopharmacology 143 (3) (1999) 315-317; C. C. Felder, E. M. Briley, J. Axelrod, J. T. Simpson, K. Mackie, W. A. Devane, Proc. Natl. Acad. Sci. U.S.A. 90 (16) (1993) 7656-60) and cause appetite suppression and weight loss (G. Colombo, R. Agabio, G. Diaz, C. Lobina, R. Reali, G. L. Gessa, Life Sci. 63 (8) (1998) L113-PL117).

Leptin is the primary signal through which the hypothalamus senses nutritional state and modulates food intake and energy balance. Following temporary food restriction, CB1 receptor knockout mice eat less than their wild-type littermates, and the CB1 antagonist SR141716A reduces food intake in wild-type but not knockout mice. Furthermore, defective leptin signaling is associated with elevated hypothalamic, but not cerebellar, levels of endocannabinoids in obese db/db and ob/ob mice and Zucker rats. Acute leptin treatment of normal rats and ob/ob mice reduces anandamide and 2-arachidonoyl glycerol in the hypothalamus. These findings indicate that endocannabinoids in the hypothalamus may tonically activate CB1 receptors to maintain food intake and form part of the neural circuitry regulated by leptin (V. Di Marzo, S. K. Goparaju, L. Wang, J. Liu, S. Bitkai, Z. Jarai, F. Fezza, G. I. Miura, R. D. Palmiter, T. Sugiura, G. Kunos, Nature 410 (6830) 822-825).

SR-141716A, a CB1 selective antagonist/inverse agonist is currently undergoing phase III clinical trials for the treatment of obesity. In a double blind placebo-controlled study, at the doses of 5, 10 and 20 mg daily, SR 141716 significantly reduced body weight when compared to placebo (F. Barth, M. Rinaldi-Carmona, M. Arnone, H. Heshmati, G. Le Fur, "Cannabinoid antagonists: From research tools to potential new drugs." Abstracts of Papers, 222nd ACS National Meeting, Chicago, Ill., United States, Aug. 26-30, 2001).

Other compounds which have been proposed as CB1 receptor antagonists respectively inverse agonists are aminoalkylindols (AAI; M. Pacheco, S. R. Childers, R. Arnold, F. Casiano, S. J. Ward, J. Pharmacol. Exp. Ther. 257 (1) (1991) 170-183), like 6-bromo-(WIN54661; F. M. Casiano, R. Arnold, D. Haycock, J. Kuster, S. J. Ward, NIDA Res. Monogr. 105 (1991) 295-6) or 6-iodopravadoline (AM630, K. Hosohata, R. M. Quock, R. M; Hosohata, T. H. Burkey, A. Makriyannis, P. Consroe, W. R. Roeske, H. I. Yamamura, Life Sci. 61 (1997) 115-118; R. Pertwee, G. Griffin, S. Fernando, X. Li, A. Hill, A. Makriyannis, Life Sci. 56 (23-24) (1995) 1949-55). Arylbenzo[b] thiophene and benzo[b] furan (LY320135, C. C. Felder, K. E. Joyce, E. M. Briley, M. Glass, K. P. Mackie, K. J. Fahey, G. J. Cullinan, D. C. Hunden, D. W. Johnson, M. O. Chaney, G. A. Koppel, M. Brownstein, J. Pharmacol. Exp. Ther. 284 (1) (1998) 291-7) disclosed in WO9602248, U.S. Pat. No. 5,596,106, 3-alkyl-(5,5-diphenyl)imidazolidinediones (M. Kanyonyo, S. J. Govaerts, E. Hermans, J. H. Poupaert, D. M. Lambert, Bioorg. Med. Chem. Lett. 9 (15) (1999) 2233-2236.) as well as 3-alkyl-5-arylimidazolidinediones (F. Ooms, J. Wouters, O. Oscaro. T. Happaerts, G. Bouchard, P.-A. Carrupt, B. Testa, D. M. Lambert, J. Med. Chem. 45 (9) (2002) 1748-1756) are known to antagonize the $CB_1$ receptor respectively act as an inverse agonist on the $hCB_1$ receptor. WO0015609 (FR2783246-A1), WO0164634 (FR2805817-A1), WO0228346, WO0164632 (FR2805818-A1), WO0164633 (FR2805810-A1) disclosed substituted 1-bis(aryl)methyl-azetidines derivatives as antagonists of $CB_1$. In WO0170700 4,5-dihydro-1H-pyrazole derivatives are described as $CB_1$ antagonists. In several patents bridged and non-bridged 1,5-diphenyl-3-pyrazolecarboxamide derivatives are disclosed as $CB_1$ antagonists/inverse agonists (WO0132663, WO0046209, WO9719063, EP658546, EP656354, U.S. Pat. No. 5,624,941, EP576357, U.S. Pat. No. 3,940,418).

A need exists in the art for selective, directly acting CB1 receptor antagonists respectively inverse agonists. Such antagonists/inverse antagonists are useful in medical therapy, particularly in the treatment and/or prevention of diseases which are associated with the modulation of CB1 receptors.

SUMMARY OF THE INVENTION

In one embodiment of the present invention, provided is a compound of the formula I:

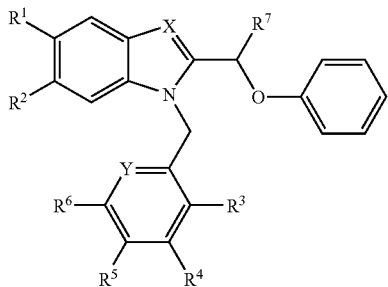

I wherein
X is N or CH;
$R^1$ is —C(O)—$NR^8R^9$ or —C(O)—$OR^{10}$ and $R^2$ is hydrogen; or, alternatively,
$R^2$ is

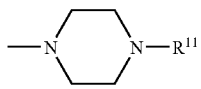

and $R^1$ is hydrogen or halogen;
Y is N or CH;
$R^3$, $R^4$, $R^5$ and $R^6$ independently from each other are selected from the group consisting of hydrogen, halogen, lower alkoxy, lower fluoroalkyl, lower fluoroalkoxy, and lower fluoroalkylsulfanyl; or $R^3$ and $R^4$ together with the carbon atoms they are attached to form a 5- or 6-membered unsaturated ring which may contain a heteroatom selected from the group consisting of N, O or S;
$R^7$ is hydrogen or lower alkyl;
$R^8$ is hydrogen or —$NH_2$;
$R^9$ is selected from the group consisting of lower alkyl, lower alkenyl, lower alkoxyalkyl,
—$(CH_2)_m$—$C_{3-7}$-cycloalkyl, —$(CH_2)_m$-piperidinyl,
—$(CH_2)_m$-phenyl, wherein the phenyl ring is unsubstituted or substituted by one or two groups selected from halogen, lower alkoxy, lower fluoroalkyl and lower fluoroalkoxy,
—$(CH_2)_m$-naphthyl, and
pyridylamino;
$R^{10}$ is lower alkyl or lower alkenyl;
$R^{11}$ is selected from the group consisting of —C(O)—$R^{12}$, —$SO_2$—$R^{13}$ and —$SO_2$—$NR^{14}R^5$;
$R^{12}$ is selected from the group consisting of lower alkyl, lower alkoxyalkyl, —$(CH_2)_n$—$C_{3-7}$-cycloalkyl, —$(CH_2)_n$-phenyl and —$(CH_2)_n$-pyridyl, wherein the phenyl or pyridyl is unsubstituted or substituted by lower alkyl;
$R^{13}$ is selected from lower alkyl or —$(CH_2)_n$-phenyl, wherein the phenyl is unsubstituted or substituted by lower alkyl;
$R^{14}$ is hydrogen or lower alkyl;
$R^{15}$ is lower alkyl or —$(CH_2)_n$—$C_{3-7}$-cycloalkyl;
m is 0, 1 or 2; and
n is 0 or 1;

and all pharmaceutically acceptable salts thereof.

In another embodiment of the present invention, provided is a process for the manufacture of compounds according to formula I, comprising the steps of:

where $R^2$ is

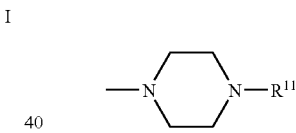

and $R^1$ is hydrogen or halogen, reacting a compound of formula

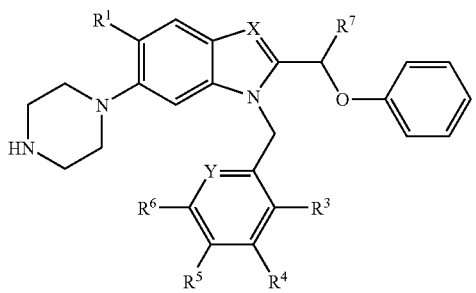

II wherein X, Y and $R^1$ to $R^7$ are as defined for formula 1, with a chloride of formula

III

Cl—$R^{11}$ wherein $R^{11}$ is selected from —C(O)—$R^{12}$, —$SO_2$—$R^{13}$ or —$SO_2$—$NR^{14}R^{15}$ and $R^{12}$, $R^{13}$, $R^{14}$ and $R^{15}$ are as defined for formula I, to obtain a compound of formula

I-A

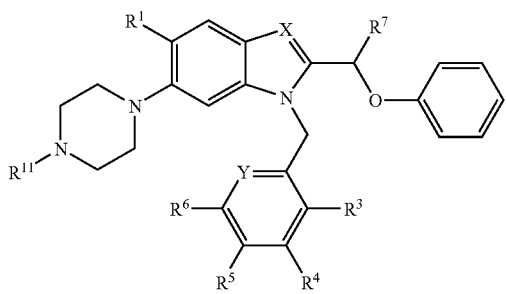

wherein X, Y, $R^1$ to $R^7$ and $R^{11}$ are as defined for formula I, or where $R^1$ is —C(O)—$NR^8R^9$ or —C(O)—$OR^{10}$ and $R^2$ is hydrogen, reacting a compound of formula

IV

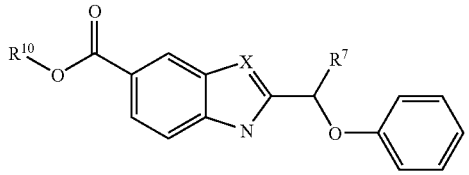

wherein X, $R^7$ and $R^{10}$ are as defined for formula I, in the presence of sodium hydride with a bromide of formula

V

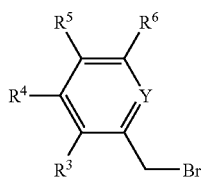

wherein Y and $R^3$ to $R^6$ are as defined for formula I, to obtain a compound of formula

I-B

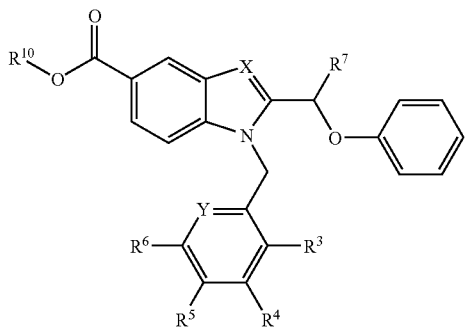

and optionally reacting this compound, after transforming it into the free acid, with an amine of the formula

H—$NR^8R^9$     VI wherein $R^8$ and $R^9$ are as defined for formula I, to obtain a compound of formula

I-C

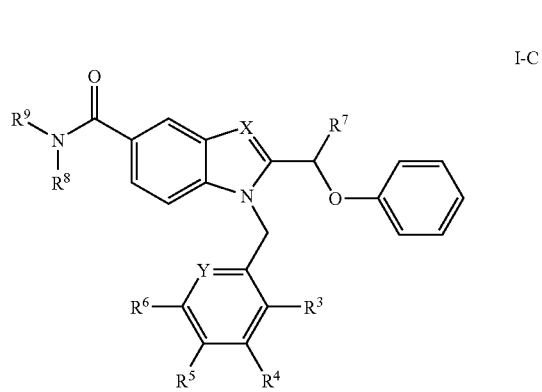

wherein X, Y and $R^3$ to $R^9$ are as defined formula I, or where $R^1$ is —C(O)—$NR^8R^9$ or —C(O)—$OR^{10}$, $R^2$ is hydrogen and X is N, reacting a compound f formula

VII

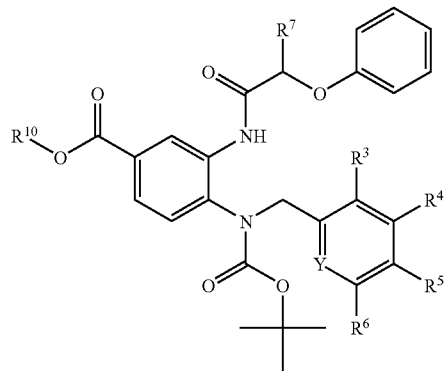

wherein Y, $R^3$ to $R^7$ and $R^{10}$ are as defined for formula I, in the presence of an acid to obtain a compound of formula

I-D

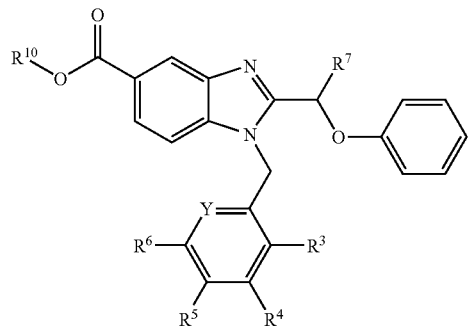

and optionally reacting this compound, after transforming it into the free acid, with an amine of the formula

wherein $R^8$ and $R^9$ are as defined for formula I, to obtain a compound of formula

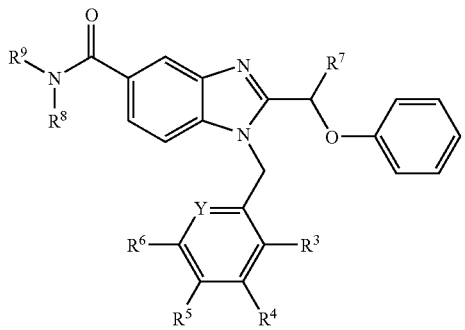

wherein Y and $R^3$ to $R^9$ are as defined formula I, and, if desired, converting the resulting compound of formula I into a pharmaceutically acceptable salt thereof.

In a further embodiment of the present invention, provided is a pharmaceutical composition, comprising a therapeutically effective amount of a compound according to formula I and a pharmaceutically acceptable carrier and/or adjuvant.

In yet another embodiment of the present invention, provided is a method for the treatment and/or prophylaxis of diseases or disorders which are associated with the modulation of the CB1 receptors, comprising the step of administering a therapeutically effective amount of a compound according to formula I to a human being or animal in need thereof.

DETAILED DESCRIPTION OF THE INVENTION

Unless otherwise indicated, the following definitions are set forth to illustrate and define the meaning and scope of the various terms used to describe the invention herein. In this specification the term "lower" is used to mean a group consisting of one to eight, preferably of one to four carbon atom(s).

The term "alkyl" alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination with other groups, refers to a branched or straight-chain monovalent alkyl radical of one to seven carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "lower alkenyl" or "$C_{2-7}$-alkenyl", alone or in combination with other groups, signifies a straight-chain or branched monovalent hydrocarbon radical comprising an olefinic bond and up to 7, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "alkoxy" refers to the group R'—O—, wherein R' is alkyl. The term "lower alkoxy" or "$C_{1-7}$-alkoxy" refers to the group R'—O—, wherein R' is lower alkyl. Examples of lower alkoxy groups are e.g. methoxy, ethoxy, propoxy, isopropoxy, butoxy, isobutoxy and hexyloxy, with methoxy being especially preferred.

The term "alkoxy-lower alkyl" or "$C_{1-7}$-alkoxy-$C_{1-7}$-alkyl" refers to a lower alkyl group as defined above which is mono- or multiply substituted with a lower alkoxy group as defined above.

Examples of alkoxy-lower alkyl groups are e.g. —CH$_2$—O—CH$_3$, —CH$_2$—CH$_2$—O—CH$_3$, —CH$_2$—O—CH$_2$—CH$_3$ and the groups specifically exemplified herein.

The term "halogen" refers to fluorine, chlorine, bromine and iodine.

The term "fluoro-lower alkyl" or "fluoro-$C_{1-7}$-alkyl" refers to lower alkyl groups which are mono- or multiply substituted with fluorine. Examples of fluoro-lower alkyl groups are —CF$_3$, —CHF$_2$, —CH$_2$CF$_3$, —CH(CF$_3$)$_2$, —CF$_2$—CF$_3$ and the groups specifically exemplified herein.

The term "fluoro-lower alkoxy" or "fluoro-$C_{1-7}$-alkoxy" refers to a lower alkoxy group as defined above wherein at least one of the hydrogens of the lower alkoxy group is replaced by fluoro. Among the preferred fluoro-lower alkoxy groups are trifluoromethoxy, difluoromethoxy and fluoromethoxy, with trifluoromethoxy being especially preferred.

The term "alkylsulfanyl" refers to the group R'—S—, wherein R' is alkyl. The term "lower alkylsulfanyl" or "$C_{1-7}$-alkylsulfanyl" refers to the group R'—O—, wherein R' is lower alkyl. Examples of lower alkylsulfanyl groups are methylsulfanyl or ethylsulfanyl.

The term "fluoro-lower alkylsulfanyl" or "fluoro-$C_{1-7}$-alkylsulfanyl" refers to a lower alkylsulfanyl group as defined above wherein at least one of the hydrogens of the lower alkyl group is replaced by fluoro. Among the preferred fluoro-lower alkylsulfanyl groups are trifluoromethylsulfanyl and pentafluoroethylsulfanyl, with trifluoromethylsulfanyl being especially preferred.

The term "cycloalkyl" refers to a monovalent carbocyclic radical of three to seven, preferably three to five carbon atoms. This term is further exemplified by radicals such as cyclopropyl, cyclobutyl, cyclopentyl, cyclohexyl and cycloheptyl, with cyclopropyl being especially preferred.

The term "pyridylamino" means an amino group which is monosubstituted by a pyridyl ring. Most preferred is a 2-pyridylamino group.

The term "pharmaceutically acceptable salts" embraces salts of the compounds of formula I with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In detail, the present invention relates to new compounds the general formula

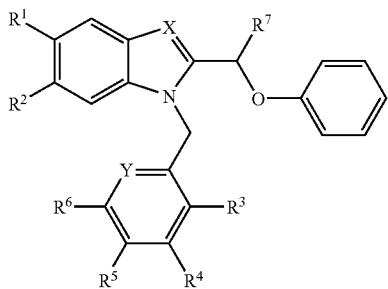

wherein
X is N or CH;
R¹ is —C(O)—NR⁸R⁹ or —C(O)—OR¹⁰ and R² is hydrogen; or, alternatively,
R² is

and R¹ is hydrogen or halogen;
Y is N or CH;
R³, R⁴, R⁵ and R⁶ independently from each other are selected from the group consisting of hydrogen, halogen, lower alkoxy, lower fluoroalkyl, lower fluoroalkoxy, and lower fluoroalkylsulfanyl; or
  R³ and R⁴ together with the carbon atoms they are attached to form a 5- or 6-membered unsaturated ring which may contain a heteroatom selected from the group consisting of N, O or S;
R⁷ is hydrogen or lower alkyl;
R⁸ is hydrogen or —NH₂;
R⁹ is selected from the group consisting of lower alkyl, lower alkenyl, lower alkoxy alkyl,
—(CH₂)$_m$—C$_{3-7}$-cycloalkyl, —(CH₂)$_m$-piperidinyl,
—(CH₂)$_m$-phenyl, wherein the phenyl ring is unsubstituted or substituted by one or two groups selected from halogen, lower alkoxy, lower fluoroalkyl and lower fluoroalkoxy,
—(CH₂)$_m$-naphthyl, and
pyridylamino;
R¹⁰ is lower alkyl or lower alkenyl;
R¹¹ is selected from the group consisting of —C(O)—R¹², —SO₂—R¹³ and —SO₂—NR¹⁴R¹⁵;
R¹² is selected from the group consisting of lower alkyl, lower alkoxy alkyl,
—(CH₂)$_n$—C$_{3-7}$-cycloalkyl, —(CH₂)$_n$-phenyl and —(CH₂)$_n$-pyridyl, wherein the phenyl or pyridyl is unsubstituted or substituted by lower alkyl;
R¹³ is selected from lower alkyl or —(CH₂)$_n$-phenyl, wherein the phenyl is unsubstituted or substituted by lower alkyl;
R¹⁴ is hydrogen or lower alkyl;
R¹⁵ is lower alkyl or —(CH₂)$_n$—C$_{3-7}$-cycloalkyl;
m is 0, 1 or 2;
n is 0 or 1; and
all pharmaceutically acceptable salts thereof.

Preferred are compounds of formula I as defined above, wherein X is N.

Preferred are also compounds of formula I according to the present invention, wherein X is N and wherein R¹ is —C(O)—NR⁸R⁹ or —C(O)—OR¹⁰, R² is hydrogen and R⁸, R⁹ and R¹⁰ are as defined herein before, with those compounds, wherein R¹ is —C(O)—NR⁸R⁹, R² is hydrogen, R⁸ is hydrogen or —NH₂ and R⁹ is selected from the group consisting of lower alkyl, lower alkenyl, lower alkoxyalkyl, —(CH₂)$_m$—C$_{3-7}$-cycloalkyl, —(CH₂)$_m$-piperidinyl, —(CH₂)$_m$-phenyl, wherein the phenyl ring is unsubstituted or substituted by one or two groups selected from halogen, lower alkoxy, lower fluoroalkyl and lower fluoroalkoxy, —(CH₂)$_m$-naphthyl, and pyridylamino, being especially preferred.

Even more preferred are those compounds, wherein X is N, R¹ is —C(O)—NR⁸R⁹, R⁸ is hydrogen and R⁹ is selected from the group consisting of lower alkyl, lower alkenyl, lower alkoxy alkyl, —(CH₂)$_m$—C$_{3-7}$-cycloalkyl, —(CH₂)$_m$-piperidinyl, —(CH₂)$_m$-phenyl, wherein the phenyl ring is unsubstituted or substituted by one or two groups selected from halogen, lower alkoxy, lower fluoroalkyl and lower fluoroalkoxy, —(CH₂)$_m$-naphthyl, and pyridylamino, and m is 0, 1 or 2. Within this group, compounds, wherein R⁹ is selected from the group consisting of lower alkyl, —(CH₂)$_m$—C$_{3-7}$-cycloalkyl and —(CH₂)$_m$-piperidinyl, are especially preferred.

Furthermore, compounds of formula I according to the present invention, wherein R² is

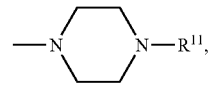

R¹ is hydrogen or halogen, and R¹¹ is selected from the group consisting of —C(O)—R¹², —SO₂—R¹³ and —SO₂—NR¹⁴R¹⁵, are preferred.

In one embodiment, compounds of formula I, wherein R² is

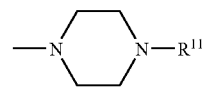

and R¹ is hydrogen, are preferred.

Compounds of formula I, wherein R² is

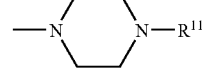

and R¹ is halogen, are also preferred.

More preferred are compounds of formula I, wherein X is N, and wherein R² is

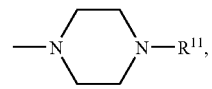

R¹ is hydrogen or halogen, and R¹¹ is selected from the group consisting of —C(O)—R¹², —SO₂—R¹³ and —SO₂—NR¹⁴R¹⁵.

Especially preferred are those compounds of formula I, wherein R¹¹ is —C(O)—R¹² and R¹² is selected from the group consisting of lower alkyl, lower alkoxyalkyl, —(CH₂)

$_n$—$C_{3-7}$-cycloalkyl, —$(CH_2)_n$-phenyl and —$(CH_2)_n$-pyridyl, wherein the phenyl or pyridyl is unsubstituted or substituted by lower alkyl, with those compounds of formula I, wherein $R^{12}$ is lower alkyl or —$(CH_2)_n$-phenyl, wherein the phenyl is unsubstituted or substituted by lower alkyl, being even more preferred.

Another group of especially preferred compounds of formula I are those, wherein $R^{11}$ is —$SO_2$—$R^{13}$ and $R^{13}$ is selected from lower alkyl or —$(CH_2)_n$-phenyl, wherein the phenyl is unsubstituted or substituted by lower alkyl, with those compounds, wherein $R^{13}$ is lower alkyl, being even more preferred.

Furthermore, compounds of formula I, wherein $R^{11}$ is —$SO_2$—$NR^{14}R^{15}$ and $R^{14}$ and $R^{15}$ lower alkyl, are also preferred.

In another embodiment, compounds of formula I, wherein X is CH, are also preferred.

Especially preferred are those compounds of formula I, wherein X is CH and wherein $R^1$ is —C(O)—$NR^8R^9$, $R^2$ is hydrogen, $R^8$ is hydrogen or —$NH_2$ and $R^9$ is selected from the group consisting of lower alkyl, lower alkenyl, lower alkoxy alkyl, —$(CH_2)_m$—$C_{3-7}$-cycloalkyl, —$(CH_2)_m$-piperidinyl, —$(CH_2)_m$-phenyl, wherein the phenyl ring is unsubstituted or substituted by one or two groups selected from halogen, lower alkoxy, lower fluoroalkyl and lower fluoroalkoxy, —$(CH_2)_m$-naphthyl, and pyridylamino.

More preferred are those compounds within this group, wherein $R^8$ is hydrogen and $R^9$ is selected from the group consisting of $C_{1-7}$-alkyl, —$(CH_2)_m$—$C_{3-7}$-cycloalkyl and —$(CH_2)_m$-piperidinyl and m is 0, 1 or 2.

Especially preferred are compounds of formula I of the present invention, wherein Y is CH.

Furthermore, compounds of formula I are preferred, wherein at least one of $R^3$, $R^4$, $R^5$ and $R^6$ is selected from the group consisting of halogen, lower alkoxy, lower fluoroalkyl, lower fluoroalkoxy, and lower fluoroalkylsulfanyl; or wherein $R^3$ and $R^4$ together with the carbon atoms they are attached to form a 5- or 6-membered unsaturated ring which may contain a heteroatom selected from the group consisting of N, O or S.

More preferred are those compounds of formula I, wherein $R^5$ is selected from the group consisting of halogen, lower alkoxy, lower fluoroalkyl, lower fluoroalkoxy, and lower fluoroalkylsulfanyl and $R^3$, $R^4$ and $R^6$ are hydrogen.

Also preferred are compounds of formula I, wherein $R^3$ is selected from the group consisting of halogen, lower alkoxy, lower fluoroalkyl, lower fluoroalkoxy, and lower fluoroalkylsulfanyl and $R^4$, $R^5$ and $R^6$ are hydrogen.

A further group of preferred compounds of formula I are those, wherein $R^4$ is selected from the group consisting of halogen, $C_{1-7}$-alkoxy, lower fluoroalkyl, lower fluoro-alkoxy, and lower fluoroalkylsulfanyl and $R^3$, $R^5$ and $R^6$ are hydrogen.

Furthermore, compounds of formula I of the present invention, wherein $R^7$ is hydrogen or lower alkyl, are preferred. Especially preferred are those compounds of formula I, wherein $R^7$ is hydrogen or methyl, with those compounds, wherein $R^7$ is methyl being especially preferred.

Preferred compounds of general formula I are the following compounds:

6-(4-methanesulfonyl-piperazin-1-yl)-2-phenoxymethyl-1-(4-trifluoromethoxy-benzyl)-1H-benzoimidazole,
6-[4-(butane-1-sulfonyl)-piperazin-1-yl]-2-phenoxymethyl-1-(4-trifluoromethoxy-benzyl)-1H-benzoimidazole,
4-[2-phenoxymethyl-3-(4-trifluoromethoxy-benzyl)-3H-benzoimidazol-5-yl]-piperazine-1-sulfonic acid dimethylamide,
6-(4-benzenesulfonyl-piperazin-1-yl)-2-phenoxymethyl-1-(4-trifluoromethoxy-benzyl)-1H-benzoimidazole,
2-phenoxymethyl-6-(4-phenylmethanesulfonyl-piperazin-1-yl)-1-(4-trifluoromethoxy-benzyl)-1H-benzoimidazole,
2-phenoxymethyl-6-[4-(toluene-2-sulfonyl)-piperazin-1-yl]-1-(4-trifluoromethoxy-benzyl)-1H-benzoimidazole,
1-{4-[2-phenoxymethyl-3-(4-trifluoromethoxy-benzyl)-3H-benzoimidazol-5-yl]-piperazin-1-yl}-ethanone,
1-{4-[2-phenoxymethyl-3-(4-trifluoromethoxy-benzyl)-3H-benzo-imidazol-5-yl]-piperazin-1-yl}-propan-1-one,
1-{4-[2-phenoxymethyl-3-(4-trifluoromethoxy-benzyl)-3H-benzo-imidazol-5-yl]-piperazin-1-yl}-pentan-1-one,
1-{4-[2-phenoxymethyl-3-(4-trifluoromethoxy-benzyl)-3H-benzo-imidazol-5-yl]-piperazin-1-yl}-2-phenyl-ethanone,
6-(4-methanesulfonyl-piperazin-1-yl)-2-phenoxymethyl-1-(4-trifluoromethyl-benzyl)-1H-benzoimidazole,
6-[4-(butane-1-sulfonyl)-piperazin-1-yl]-2-phenoxymethyl-1-(4-trifluoromethyl-benzyl)-1H-benzoimidazole,
2-phenoxymethyl-6-(4-phenylmethanesulfonyl-piperazin-1-yl)-1-(4-trifluoromethyl-benzyl)-1H-benzoimidazole,
1-{4-[2-phenoxymethyl-3-(4-trifluoromethyl-benzyl)-3H-benzo-imidazol-5-yl]-piperazin-1-yl}-propan-1-one,
1-{4-[2-phenoxymethyl-3-(4-trifluoromethyl-benzyl)-3H-benzo-imidazol-5-yl]-piperazin-1-yl}-pentan-1-one,
{4-[2-phenoxymethyl-3-(4-trifluoromethyl-benzyl)-3H-benzo-imidazol-5-yl]-piperazin-1-yl}-phenyl-methanone,
1-{4-[2-phenoxymethyl-3-(4-trifluoromethyl-benzyl)-3H-benzoimidazol-5-yl]-piperazin-1yl}-2-phenyl-ethanone,
{4-[2-phenoxymethyl-3-(4-trifluoromethyl-benzyl)-3H-benzo-imidazol-5-yl]-piperazin-1-yl}-o-tolyl-methanone,
[4-(3-benzyl-2-phenoxymethyl-3H-benzoimidazol-5-yl)-piperazin-1-yl]-phenyl-methanone,
[4-(3-benzyl-2-phenoxymethyl-3H-benzoimidazol-5-yl)-piperazin-1-yl]-o-tolyl-methanone,
6-(4-methanesulfonyl-piperazin-1-yl)-2-(1-phenoxy-ethyl)-1-(4-trifluoromethoxy-benzyl)-1H-benzoimidazole,
6-[4-(butane-1-sulfonyl)-piperazin-1-yl]-2-(1-phenoxy-ethyl)-1-(4-trifluoromethoxy-benzyl)-1H-benzoimidazole,
4-[2-(1-phenoxy-ethyl)-3-(4-trifluoromethoxy-benzyl)-3H-benzoimidazol-5-yl]-piperazine-1-sulfonic acid dimethylamide,
2-(1-phenoxy-ethyl)-6-[4-(toluene-2-sulfonyl)-piperazin-1-yl]-1-(4-trifluoromethoxy-benzyl)-1H-benzoimidazole,
1-{4-[2-(1-phenoxy-ethyl)-3-(4-trifluoro-methoxy-benzyl)-3H-benzoimidazol-5-yl]-piperazin-1-yl}-ethanone,
1-{4-[2-(1-phenoxy-ethyl)-3-(4-trifluoro-methoxy-benzyl)-3H-benzoimidazol-5-yl]-piperzin-1-yl}-propan-1-one,
1-{4-[2-(1-phenoxy-ethyl)-3-(4-trifluoro-methoxy-benzyl)-3H-benzoimidazol-5-yl]-piperazin-1-yl}-hexan-1-one,
{4-[2-(1-phenoxy-ethyl)-3-(4-trifluoromethoxy-benzyl)-3H-benzo-imidazol-5-yl]-piperazin-1-yl}-o-tolyl-methanone,
6-[4-(butane-1-sulfonyl)-piperazin-1-yl]-2-(1-phenoxy-ethyl)-1-(4-trifluoromethyl-benzyl)-1H-benzoimidazole,
4-[2-(1-phenoxy-ethyl)-3-(4-trifluoromethyl-benzyl)-3H-benzo-imidazol-5-yl]-piperazine-1-sulfonic acid dimethylamide,
6-(4-benzenesulfonyl-piperazin-1-yl)-2-(1-phenoxy-ethyl)-1-(4-trifluoromethyl-benzyl)-1H-benzoimidazole,
2-(1-phenoxy-ethyl)-6-(4-phenylmethanesulfonyl-piperazin-1-yl)-1-(4-trifluoromethyl-benzyl)-1H-benzoimidazole,
2-(1-phenoxy-ethyl)-6-[4-(toluene-2-sulfonyl)-piperazin-1-yl]-1-(4-trifluoromethyl-benzyl)-1H-benzoimidazole, 1-{4-[2-(1-phenoxy-ethyl)-3-(4-trifluoro-methyl-benzyl)-3H-benzoimidazol-5-yl]-piperzain-1-yl}-ethanone,
1-{4-[2-(1-phenoxy-ethyl)-3-(4-trifluoro-methyl-benzyl)-3H-benzoimidazol-5-yl]-piperazin-1-yl}-propan-1-one,
1-{4-[2-(1-phenoxy-ethyl)-3-(4-trifluoro-methyl-benzyl)-3H-benzoimidazol-5-yl]-piperazin-1-yl}-hexan-1-one,
{4-[2-(1-phenoxy-ethyl)-3-(4-trifluoromethyl-benzyl)-3H-benzo-imidazol-5-yl]-piperazin-1-yl}-phenyl-methanone,
1-{4-[2-(1-phenoxy-ethyl)-3-(4-trifluoro-methyl-benzyl)-3H-benzoimidazol-5-yl]-piperazin-1-yl}-2-phenyl-ethanone
{4-[2-(1-phenoxy-ethyl)-3-(4-trifluoromethyl-benzyl)-3H-benzo-imidazol-5-yl]-piperazin-1-yl}-o-tolyl-methanone,
benzyl-6-[4-(butane-1-sulfonyl)-piperazin-1-yl]-2-(1-phenoxy-ethyl)-1H-benzoimidazole,
4-[3-benzyl-2-(1-phenoxy-ethyl)-3H-benzoimidazol-5-yl]-piperazine-1-sulfonic acid dimethylamide,
6-(4-benzenesulfonyl-piperazin-1-yl)-1-benzyl-2-(1-phenoxy-ethyl)-1H-benzoimidazole,
benzyl-2-(1-phenoxy-ethyl)-6-[4-(toluene-2-sulfonyl)-piperazin-1-yl]-1H-benzoimidazole,
1-{4-[3-benzyl-2-(1-phenoxy-ethyl)-3H-benzoimidazol-5-yl]-piperazin-1-yl}-propan-1-one,
1-{4-[3-benzyl-2-(1-phenoxy-ethyl)-3H-benzoimidazol-5-yl]-piperazin-1-yl}-hexan-1-one,
{4-[3-benzyl-2-(1-phenoxy-ethyl)-3H-benzoimidazol-5-yl]-piperazin-1-yl}-phenyl-methone,
1-{4-[3-benzyl-2-(1-phenoxy-ethyl)-3H-benzoimidazol-5-yl]-piperazin-1-yl}-2-phenyl-ethanone,
{4-[3-benzyl-2-(1-phenoxy-ethyl)-3H-benzoimidazol-5-yl]-piperazin-1-yl}-o-tolyl-methone,
1-(4-chloro-benzyl)-6-(4-methanesulfonyl-piperazin-1-yl)-2-(1-phenoxy-ethyl)-1H-benzoimidazole,
6-[4-(butane-1-sulfonyl)-piperazin-1-yl]-1-(4-chloro-benzyl)-2-(1-phenoxy-ethyl)-benzoimidazole,
4-[3-(4-chloro-benzyl)-2-(1-phenoxy-ethyl)-3H-benzoimidazol-5-yl]-piperazine-1-sulfonic acid dimethylamide,
6-(4-benzenesulfonyl-piperazin-1-yl)-1-(4-chloro-benzyl)-2-(1-phenoxy-ethyl)-1H-benzoimidazole,
1-(4-chloro-benzyl)-2-(1-phenoxy-ethyl)-6-(4-phenyl-methanesulfonyl-piperazin-1-yl)-1H-benzoimidazole,
1-(4-chloro-benzyl)-2-(1-phenoxy-ethyl)-6-[4-(toluene-2-sulfonyl)-piperazin-1-yl]-1H-benzoimidazole,
1-{4-[3-(4-chloro-benzyl)-2-(1-phenoxy-ethyl)-3H-benzoimidazol-5-yl]-piperazin-1-yl}-ethanone,
1-{4-[3-(4-chloro-benzyl)-2-(1-phenoxy-ethyl)-3H-benzoimidazol-5-yl]-piperazin-1-yl}-propan-1-one,
1-{4-[3-(4-chloro-benzyl)-2-(1-phenoxy-ethyl)-3H-benzoimidazol-5-yl]-piperazin-1-yl}-hexan-1-one,
{4-[3-(4-chloro-benzyl)-2-(1-phenoxy-ethyl)-3H-benzoimidazol-5-yl]-piperazin-1-yl}-phenyl-methanone,
{4-[3-(4-chloro-benzyl)-2-(1-phenoxy-ethyl)-3H-benzoimidazol-5-yl]-piperazin-1-yl}-o-tolyl-methanone,
phenoxymethyl-1-(4-trifluoromethoxy-benzyl)-1H-benzoimidazole-5-carboxylic acid allyl ester,
phenoxymethyl-1-(4-trifluoromethoxy-benzyl)-1H-benzoimidazole-5-carboxylic acid butyl-amide,
phenoxymethyl-1-(4-trifluoromethoxy-benzyl)-1H-benzoimidazole-5-carboxylic acid cyclopropylamide,
phenoxymethyl-1-(4-trifluoromethoxy-benzyl)-1H-benzoimidazole-5-carboxylic acid [2-(3-methoxy-phenyl)-ethyl]-amide,
2-phenoxymethyl-1-(4-trifluoromethoxy-benzyl)-1H-benzoimidazole-5-carboxylic acid [2-(3-trifluoromethyl-phenyl)-ethyl]-amide,
2-phenoxymethyl-1-(4-trifluoromethoxy-benzyl)-1H-benzoimidazole-5-carboxylic acid pentylamide,
2-phenoxymethyl-1-(4-trifluoromethoxy-benzyl)-1H-benzoimidazole-5-carboxylic acid (2,2-dimethyl propyl)-amide,
2-phenoxymethyl-1-(4-trifluoromethoxy-benzyl)-1H-benzoimidazole-5-carboxylic acid allylamide,
2-phenoxymethyl-1-(4-trifluoromethoxy-benzyl)-1H-benzoimidazole-5-carboxylic acid (3-butoxy-propyl)-amide,
2-phenoxymethyl-1-(4-trifluoromethoxy-benzyl)-1H-benzoimidazole-5-carboxylic acid(naphthalen-1-ylmethyl)-amide,
2-phenoxymethyl-1-(4-trifluoromethoxy-benzyl)-1H-benzoimidazole-5-carboxylic acid 4-trifluoromethoxy-benzylamide,
2-phenoxymethyl-1-(4-trifluoromethoxy-benzyl)-1H-benzoimidazole-5-carboxylic acid 2-trifluoromethyl-benzylamide,
2-phenoxymethyl-1-(4-trifluoromethoxy-benzyl)-1H-benzoimidazole-5-carboxylic acid hexylamide,
2-phenoxymethyl-1-(4-trifluoromethoxy-benzyl)-1H-benzoimidazole-5-carboxylic acid heptylamide,
2-phenoxymethyl-1-(4-trifluoromethoxy-benzyl)-1H-benzoimidazole-5-carboxylic acid 2,4-difluoro-benzylamide,
2-phenoxymethyl-1-(4-trifluoromethoxy-benzyl)-1H-benzoimidazole-5-carboxylic acid 4-methoxy-benzylamide,
2-phenoxymethyl-1-(4-trifluoromethoxy-benzyl)-1H-benzoimidazole-5-carboxylic acid N'-pyridin-2-yl-hydrazide,
1-{4-[6-fluoro-2-phenoxymethyl-3-(4-trifluoromethoxy-benzyl)-3H-benzoimidazol-5-yl]-piperazin-1-yl}-ethanone,
{4-[6-fluoro-2-phenoxymethyl-3-(4-trifluoromethoxy-benzyl)-3H-benzoimidazol-5-yl]-piperazin-1-yl}-phenyl-methanone,
{4-[6-fluoro-2-phenoxymethyl-3-(4-trifluoromethoxy-benzyl)-3H-benzoimidazol-5-yl]-piperazin-1-yl}-pyridin-4-yl-methanone,
{4-[3-(4-chloro-benzyl)-6-fluoro-2-phenoxymethyl-3H-benzoimidazol-5-yl]-piperazin-1-cyclopropyl-methanone,
{4-[3-(4-chloro-benzyl)-6-fluoro-2-phenoxymethyl-3H-benzoimidazol-5-yl]-piperazin-1-yl}-phenyl-methanone,
1-{4-[3-(4-chloro-benzyl)-6-fluoro-2-phenoxymethyl-3H-benzoimidazol-5-yl]-piperazin-1-yl}-pentan-1-one,
cyclopropyl-{4-[6-fluoro-2-phenoxymethyl-3-(4-trifluoromethoxy-benzyl)-3H-benzoimidazol-5-yl]-piperazin-1-yl}-methanone,
1-{4-[6-fluoro-2-phenoxymethyl-3-(4-trifluoromethoxy-benzyl)-3H-benzoimidazol-5-yl]-piperazin-1-yl}-pentan-1-one,
1-{4-[6-fluoro-2-phenoxymethyl-3-(4-trifluoromethoxy-benzyl)-3H-benzoimidazol-5-yl]-piperazin-1-yl}-propan-1-one,
cyclopropyl-{4-[6-fluoro-2-phenoxymethyl-3-(4-trifluoromethoxy-benzyl)-3H-benzoimidazol-5-yl]-piperazin-1-yl}-methanone,
1-{4-[6-fluoro-2-phenoxymethyl-3-(4-trifluoromethoxy-benzyl)-3H-benzoimidazol-5-yl]-piperazin-1-yl}-pentan-1-one,
1-{4-[6-fluoro-2-phenoxymethyl-3-(4-trifluoromethoxy-benzyl)-3H-benzoimidazol-5-yl]-piperazin-1-yl}-propan-1-one,
1-{4-[6-fluoro-2-phenoxymethyl-3-(4-trifluoromethoxy-benzyl)-3H-benzoimidazol-5-yl]-piperazin-1-yl}-2-phenyl-ethanone,
1-{4-[6-fluoro-2-phenoxymethyl-3-(4-trifluoromethoxy-benzyl)-3H-benzoimidazol-5-yl]-piperazin-1-yl}-butan-1-one, {4-[6-fluoro-2-phenoxymethyl-3-(4-trifluoromethoxy-benzyl)-3H-benzoimidazol-5-yl]-piperazin-1-yl}-o-tolyl-methanone,
4-[6-fluoro-2-phenoxymethyl-3-(4-trifluoromethoxy-benzyl)-3H-benzoimidazol-5-yl]-piperazin-1-yl}-3-methoxy-propan-1-one,
1-{4-[3-(4-chloro-benzyl)-6-fluoro-2-phenoxymethyl-3H-benzoimidazol-5-yl]-piperazin-1-yl}-ethanone,
1-{4-[3-(4-chloro-benzyl)-6-fluoro-2-phenoxymethyl-3H-benzoimidazol-5-yl]-piperazin-1-yl}-propan-1-one,
1-{4-[3-(4-chloro-benzyl)-6-fluoro-2-phenoxymethyl-3H-benzoimidazol-5-yl]-piperazin-1-yl}-butan-1-one,
2-cyclopropyl-1-{4-[6-fluoro-2-phenoxymethyl-3-(4-trifluoromethoxy-benzyl)-3H-benzoimidazol-5-yl]-piperazin-1-yl}-ethanone,
1-{4-[3-(4-chloro-benzyl)-6-fluoro-2-phenoxymethyl-3H-benzoimidazol-5-yl]-piperazin-1-yl}-2-phenyl-ethanone,
1-{4-[3-(4-chloro-benzyl)-6-fluoro-2-phenoxymethyl-3H-benzoimidazol-5-yl]-piperazin-1-yl}-2-cyclopropyl-ethanone,
1-{4-[3-(4-chloro-benzyl)-6-fluoro-2-phenoxymethyl-3H-benzoimidazol-5-yl]-piperazin-1-yl}-3-methoxy-propan-1-one,
2-phenoxymethyl-1-(4-trifluoromethylsulfanyl-benzyl)-1H-indole-5-carboxylic acid butylamide,
1-(2-fluoro-4-trifluoromethyl-benzyl)-2-phenoxymethyl-1H-indole-5-carboxylic acid cyclopropylamide,
1-(2-chloro-5-trifluoromethyl-benzyl)-2-phenoxymethyl-1H-indole-5-carboxylic acid cyclopropylamide,
1-(2-difluoromethoxy-benzyl)-2 phenoxymethyl-1H-indole-5-carboxylic acid piperidin-1-ylamide,
2-phenoxymethyl-1-(4-trifluoromethoxy-benzyl)-1H-indole-5-carboxylic acid butylamide,
1-(4-methoxy-benzyl)-2-phenoxymethyl-1H-indole-5-carboxylic acid butylamide,
2-phenoxymethyl-1-(2-trifluoromethylsulfanyl-benzyl)-1H-indole-5-carboxylic acid butylamide,
1-(4-difluoromethoxy-benzyl)-2-phenoxy-methyl-1H-indole-5-carboxylic acid cyclopropylamide,
2-phenoxymethyl-1-(2-trifluoromethoxy-benzyl)-1H-indole-5-carboxylic acid piperidin-1-ylamide
2-phenoxymethyl-1-(3-trifluoromethoxy-benzyl)-1H-indole-5-carboxylic acid piperidin-1-ylamide,
1-(2-fluoro-5-trifluoro-methyl-benzyl)-2-phenoxymethyl-1H-indole-5-carboxylic acid butylamide,
2-phenoxymethyl-1-(4-trifluoromethyl-benzyl)-1H-indole-5-carboxylic acid butylamide,
2-phenoxymethyl-1-(3-trifluoromethylsulfanyl-benzyl)-1H-indole-5-carboxylic acid butylamide,
2-phenoxymethyl-1-(4-trifluoromethylsulfanyl-benzyl)-1H-indole-5-carboxylic acid piperidin-1-ylamide,
1-(2,5-difluoro-benzyl)-2-phenoxymethyl-1H-indole-5-carboxylic acid butylamide,
2-phenoxymethyl-1-(2,4,5-trifluoro-benzyl)-1H-indole-5-carboxylic acid cyclopropylamide,
1-(3-difluoromethoxy-benzyl)-2-phenoxy-methyl-1H-indole-5-carboxylic acid cyclopropylamide,
1-(2-fluoro-4-trifluoromethyl-benzyl)-2-phenoxymethyl-1H-indole-5-carboxylic acid butylamide,
2-phenoxymethyl-1-pyridin-2-ylmethyl-1H-indole-5-carboxylic acid butylamide,
1-(2-chloro-5-trifluoromethyl-benzyl)-2-phenoxymethyl-1H-indole-5-carboxylic acid butylamide,
1-(2-difluoromethoxy-benzyl)-2 phenoxymethyl-1H-indole-5-carboxylic acid cyclopropylamide,
1-(4-difluoromethoxy-benzyl)-2-phenoxy-methyl-1H-indole-5-carboxylic acid butylamide,
1-(3,5-difluoro-benzyl)-2-phenoxymethyl-1H-indole-5-carboxylic acid butylamide,
2-phenoxymethyl-1-(2-trifluoromethoxy-benzyl)-1H-indole-5-carboxylic acid cyclopropylamide,
2-phenoxymethyl-1-(3-trifluoromethoxy-benzyl)-1H-indole-5-carboxylic acid cyclopropylamide,
2-phenoxymethyl-1-(4-trifluoromethylsulfanyl-benzyl)-1H-indole-5-carboxylic acid cyclopropylamide,
1-(2-fluoro-4-trifluoromethyl-benzyl)-2-phenoxymethyl-1H-indole-5-carboxylic acid piperidin-1-ylamide,
2-phenoxymethyl-1-quinolin-8-ylmethyl-1H-indole-5-carboxylic acid butylamide,
2-phenoxymethyl-1-(4-trifluoromethoxy-benzyl)-1H-indole-5-carboxylic acid cyclopropylamide,
1-(4-methoxy-benzyl)-2-phenoxymethyl-1H-indole-5-carboxylic acid cyclopropylamide,
2-phenoxymethyl-1-(2-trifluoromethylsulfanyl-benzyl)-1H-indole-5-carboxylic acid cyclopropylamide,
2-phenoxymethyl-1-(2,4,5-trifluoro-benzyl)-1H-indole-5-carboxylic acid butylamide,
1-(2-fluoro-5-trifluoromethyl-benzyl)-2-phenoxymethyl-1H-indole-5-carboxylic acid cyclopropylamide,
2-phenoxymethyl-1-(4-trifluoromethyl-benzyl)-1H-indole-5-carboxylic acid cyclopropylamide,
1-(2-difluoromethoxy-benzyl)-2-phenoxymethyl-1H-indole-5-carboxylic acid butylamide,
1-(4-methoxy-3-trifluoromethyl-benzyl)-2-phenoxymethyl-1H-indole-5-carboxylic acid cyclopropylamide,
2-phenoxymethyl-1-(2-trifluoromethoxy-benzyl)-1H-indole-5-carboxylic acid butylamide,
2-phenoxymethyl-1-(3-trifluoromethoxy-benzyl)-1H-indole-5-carboxylic acid butylamide,
1-(2,5-difluoro-benzyl)-2-phenoxymethyl-1H-indole-5-carboxylic acid cyclopropylamide,
2-phenoxymethyl-1-(2,3,4-trifluoro-benzyl)-1H-indole-5-carboxylic acid cyclopropylamide,
1-(3-difluoromethoxy-benzyl)-2-phenoxymethyl-1H-indole-5-carboxylic acid piperidin-1-ylamide,
2-phenoxymethyl-1-(4-trifluoromethylsulfanyl-benzyl)-1H-indole-5-carboxylic acid N-butyl-hydrazide,
2-phenoxymethyl-1-(4-trifluoromethoxy-benzyl)-1H-indole-5-carboxylic acid N-butyl-hydrazide,
2-phenoxymethyl-1-(3-trifluoromethylsulfanyl-benzyl)-1H-indole-5-carboxylic acid N-butyl-hydrazide,
1-(3-difluoromethoxy-benzyl)-2-phenoxy-methyl-1H-indole-5-carboxylic acid N-butyl-hydrazide,
1-(2-difluoromethoxy-benzyl)-2-phenoxy-methyl-1H-indole-5-carboxylic acid N-butyl-hydrazide,
2-phenoxymethyl-1-(2-trifluoromethoxy-benzyl)-1H-indole-5-carboxylic acid N-butyl-hydrazide,
2-phenoxymethyl-1-(3-trifluoromethoxy-benzyl)-1H-indole-5-carboxylic acid N-butyl-hydrazide,
1-(2-chloro-5-trifluoromethyl-benzyl)-2-phenoxymethyl-1H-indole-5-carboxylic acid N-butyl-hydrazide,
and all pharmaceutically acceptable salts thereof.

Especially preferred are the compounds selected from the group consisting of:
6-[4-(butane-1-sulfonyl)-piperazin-1-yl]-2-phenoxymethyl-1-(4-trifluoromethoxy-benzyl)-1H-benzoimidazole,
4-[2-phenoxymethyl-3-(4-trifluoromethoxy-benzyl)-3H-benzoimidazol-5-yl]-piperazine-1-sulfonic acid dimethylamide,
4-[2-(1-phenoxy-ethyl)-3-(4-trifluoromethoxy-benzyl)-3H-benzoimidazol-5-yl]-piperazine-1-sulfonic acid dimethylamide,
{4-[2-(1-phenoxy-ethyl)-3-(4-trifluoromethyl-benzyl)-3H-benzoimidazol-5-yl]-piperazin-1-yl}-o-tolyl-methanone, 4-[3-(4-chloro-benzyl)-2-(1-phenoxy-ethyl)-3H-benzoimidazol-5-yl]-piperazine-1-sulfonic acid dimethylamide,
{4-[3-(4-chloro-benzyl)-2-(1-phenoxy-ethyl)-3H-benzoimidazol-5-yl]-piperazin-1-yl}-methanone,
2-phenoxymethyl-1-(4-trifluoromethoxy-benzyl)-1H-benzoimidazole-5-carboxylic acid butyl-amide,
2-phenoxymethyl-1-(4-trifluoromethoxy-benzyl)-1H-benzoimidazole-5-carboxylic acid cyclopropylamide,
{4-[6-fluoro-2-phenoxymethyl-3-(4-trifluoromethoxy-benzyl)-3H-benzoimidazol-5-yl]-piperazin-1-yl}-phenyl-methanone,
1-{4-[3-(4-chloro-benzyl)-6-fluoro-2-phenoxymethyl-3H-benzoimidazol-5-yl]-piperazin-1-yl}pentan-1-one,
1-{4-[6-fluoro-2-phenoxymethyl-3-(4-trifluoromethoxy-benzyl)-3H-benzoimidazol-5-yl]-piperazin-1-yl}-butan-1-one,
and all pharmaceutically acceptable salts thereof.

Furthermore, compounds of formula I selected from the group consisting of:
2-phenoxymethyl-1-(4-trifluoromethylsulfanyl-benzyl)-1H-indole-5-carboxylic acid butylamide,
1-(2-chloro-5-trifluoromethyl-benzyl)-2-phenoxymethyl-1H-indole-5-carboxylic acid cyclopropylamide,
2-phenoxymethyl-1-(4-trifluoromethoxy-benzyl)-1H-indole-5-carboxylic acid butylamide,
1-(4-methoxy-benzyl)-2-phenoxymethyl-1H-indole-5-carboxylic acid butylamide,
2-phenoxymethyl-1-(2-trifluoromethoxy-benzyl)-1H-indole-5-carboxylic acid piperidin-1-ylamide,
2-phenoxymethyl-1-(3-trifluoromethylsulfanyl-benzyl)-1H-indole-5-carboxylic acid butylamide,
2-phenoxymethyl-1-(2-trifluoromethoxy-benzyl)-1H-indole-5-carboxylic acid cyclopropylamide,
2-phenoxymethyl-1-(4-trifluoromethylsulfanyl-benzyl)-1H-indole-5-carboxylic acid cyclopropylamide,
2-phenoxymethyl-1-(4-trifluoromethoxy-benzyl)-1H-indole-5-carboxylic acid cyclopropylamide,
2-phenoxymethyl-1-(2-trifluoromethoxy-benzyl)-1H-indole-5-carboxylic acid butylamide, and all pharmaceutically acceptable salts thereof, are also especially preferred.

The present invention also relates to a process for the manufacture of compounds of formula I as defined above, which process comprises
where $R^2$ is

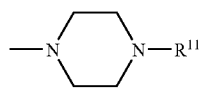

and $R^1$ is hydrogen or halogen, reacting a compound of formula

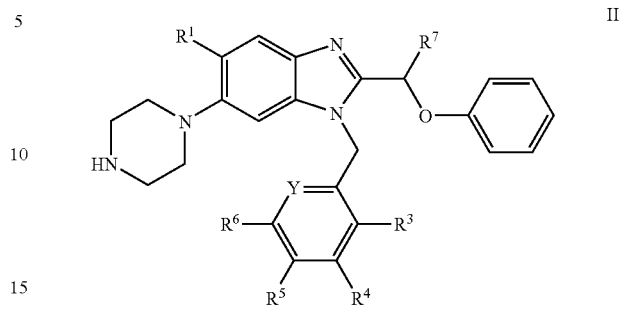

II wherein X, Y and $R^1$ to $R^7$ are as defined herein before, with a chloride of formula Cl—$R^{11}$   III wherein $R^{11}$ is selected from —C(O)—$R^{12}$, —SO$_2$—$R^{13}$ or —SO$_2$—NR$^{14}$R$^{15}$ and $R^{12}$, $R^{13}$, $R^{14}$ and $R^{15}$ are as defined herein before, to obtain a compound of formula

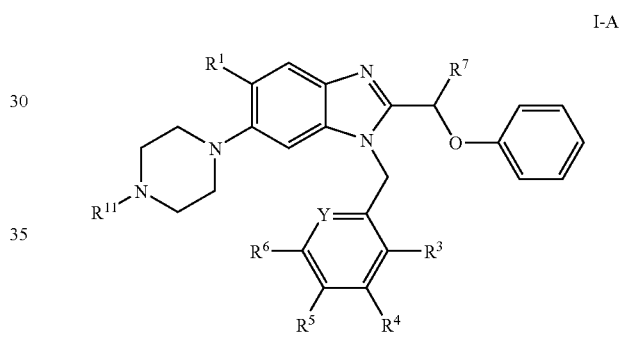

I-A wherein X, Y, $R^1$ to $R^7$ and $R^{11}$ are as defined herein before, or where $R^1$ is —C(O)—NR$^8$R$^9$ or —C(O)—OR$^{10}$ and $R^2$ is hydrogen, reacting a compound of formula

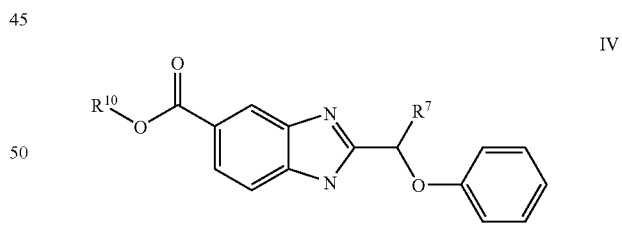

IV wherein X, $R^7$ and $R^{10}$ are as defined herein before, in the presence of sodium hydride with a bromide of formula

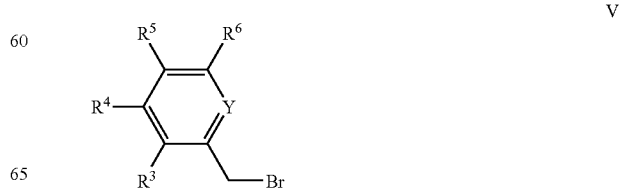

V wherein Y and $R^3$ to $R^6$ are as defined herein before, to obtain a compound of formula

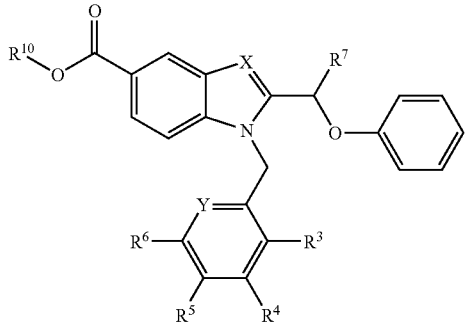

I-B and optionally reacting this compound, after transforming it into the free acid, with an amine of the formula

H—$NR^8R^9$      VI wherein $R^8$ and $R^9$ are as defined herein before, to obtain a compound of formula

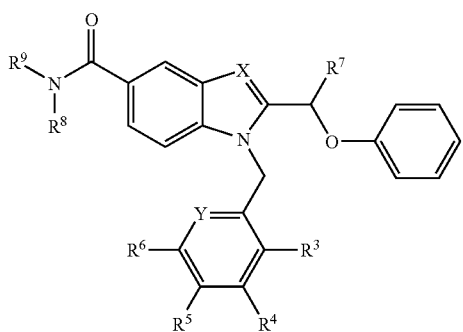

I-C wherein X, Y and $R^3$ to $R^9$ are as defined herein before, or where $R^1$ is —C(O)—$NR^8R^9$ or —C(O)—$OR^{10}$, $R^2$ is hydrogen and X is N, reacting a compound of formula

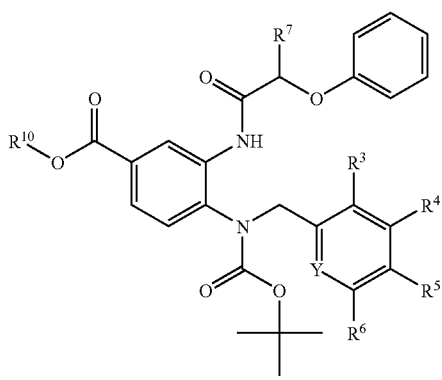

VII wherein Y, $R^3$ to $R^7$ and $R^{10}$ are as defined herein before, in the presence of an acid to obtain a compound of formula

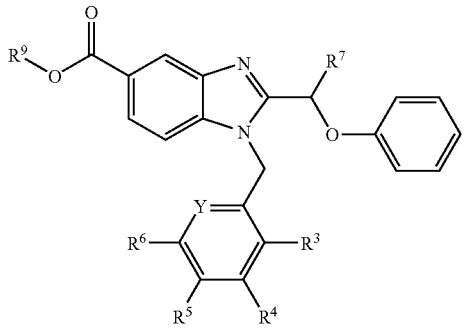

I-D and optionally reacting this compound, after transforming it into the free acid, with an amine of the formula

H—$NR^8R^9$      VI wherein $R^8$ and $R^9$ are as defined herein before, to obtain a compound of formula

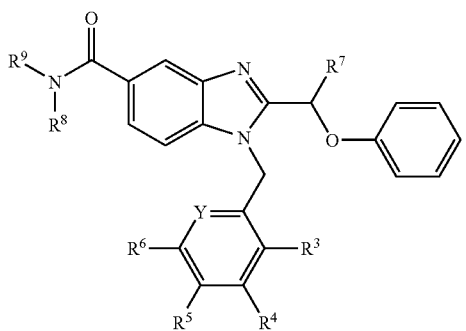

I-E wherein Y and $R^3$ to $R^9$ are as defined herein before, and, if desired, converting the resulting compound of formula I into a pharmaceutically acceptable salt thereof.

Thus, the compounds of formula I can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art.

The synthesis of compounds with the general structure I, particularly compounds according to formula I-a, wherein X is N and wherein $R^2$ is

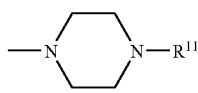

can be accomplished according to Scheme 1.

Chloro-2-nitro-phenylamine (1) is reacted with a piperazine derivative wherein one of the nitrogen atoms is protected with an amino protecting group (PG), for example a tert-butyloxycarbonyl group (BOC), an allyloxycarbonyl group or a benzyloxycarbonyl group (Z), in the presence of a base such as 1,4-diazabicyclo[2.2.2]octane (DABCO), 1,5-diazabicyclo[4.3.0non-5-ene (DBN) and the like, and heated for several hours, preferably 16 h, in a solvent like DMSO to 150° C. to obtain a compound of formula 2 wherein PG symbolizes a protecting group such as Boc (tert-butyloxycarbonyl), an allyloxycarbonyl group or a benzyloxycarbonyl group (Z).

The 2-nitro-phenylamine derivative of formula 2 is then reacted with phenoxy-acetylchloride or an 2-alkyl-2-phenoxyacetylchloride under basic conditions (for example by using an excess amount of triethylamine) to obtain a compound of formula 3 wherein $R^7$ is hydrogen or $C_{1-7}$-alkyl. In the next step the amide of formula 3 is alkylated with an appropriate benzylbromide or pyridylmethylbromide (commercially available or accessible by methods described in references or by methods known in the art, as appropriate). The introduction of the benzyl group or pyridylmethyl group must be carried out under mild conditions, we find it convenient to use cesium carbonate ($Cs_2CO_3$) in DMF similar to the method described by Wang et al., *J. Org. Chem.* 1977, 42(8), 1286-1290. The reaction can be carried out at a temperature up to 110° C., after cooling to room temperature the compounds of formula 4 precipitate.

The benzimidazole compounds of formula 5 are then formed by reduction of the nitro group of the compounds of formula 4 to the amine followed by cyclization to the benzimidazole. This reaction can be carried out in one step by using tin(II)-chloride and aqueous hydrochloride (1N) in DMF. Under the acidic conditions the amino protecting group (PG) can also be cleaved.

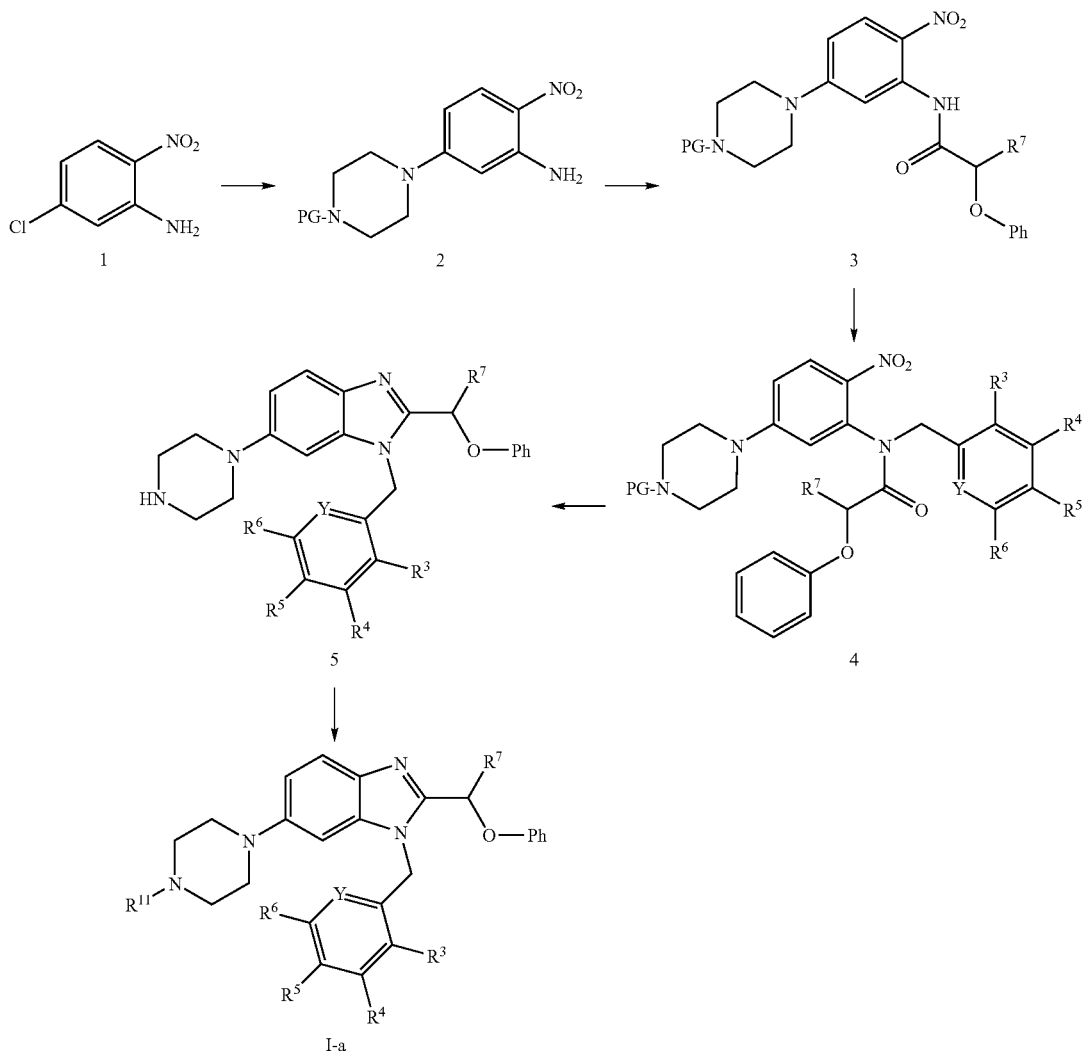

Scheme 1

PG = protecting group
$R^7$ = H or lower alkyl

In the final step the compounds of formula 5 can be reacted with the appropriate acyl chlorides (Cl—C(O)—$R^{12}$, $R^{12}$ has the meaning as defined herein before), sulfonyl chlorides (Cl—$SO_2$—$R^{13}$, $R^{13}$ is as defined herein before) or aminosulfonyl chlorides (Cl—$SO_2$—$NR^{14}R^{15}$, $R^{14}$ and $R^{15}$ defined herein before) in the presence of a base such as triethylamine. The reaction can be carried out at room temperature in a solvent like dichloromethane (DCM). The acyl chlorides, sulfonyl chlorides or aminosulfonyl chlorides are either commercially available or accessible by methods described in references or by methods known in the art, as appropriate.

The synthesis of compounds with the general structure I, particularly compounds according to formula I-b, wherein $R^1$ is —C(O)—$NR^8R^9$ or —C(O)—$OR^{10}$ and $R^2$ is hydrogen, can be accomplished according to Scheme 2.

are defined herein before (either commercially available or accessible by methods described in references or by methods known in the art).

The intermediate of formula 6a wherein X is CH can be prepared according to scheme 3 by binding a 4-amino-3-iodbenzoic acid ester 10 to a Tosylchloride resin (PS-TsCl, polystyrene sulfonyl chloride, commercially available from Argonaut Technologies) to obtain a resin bound compound of

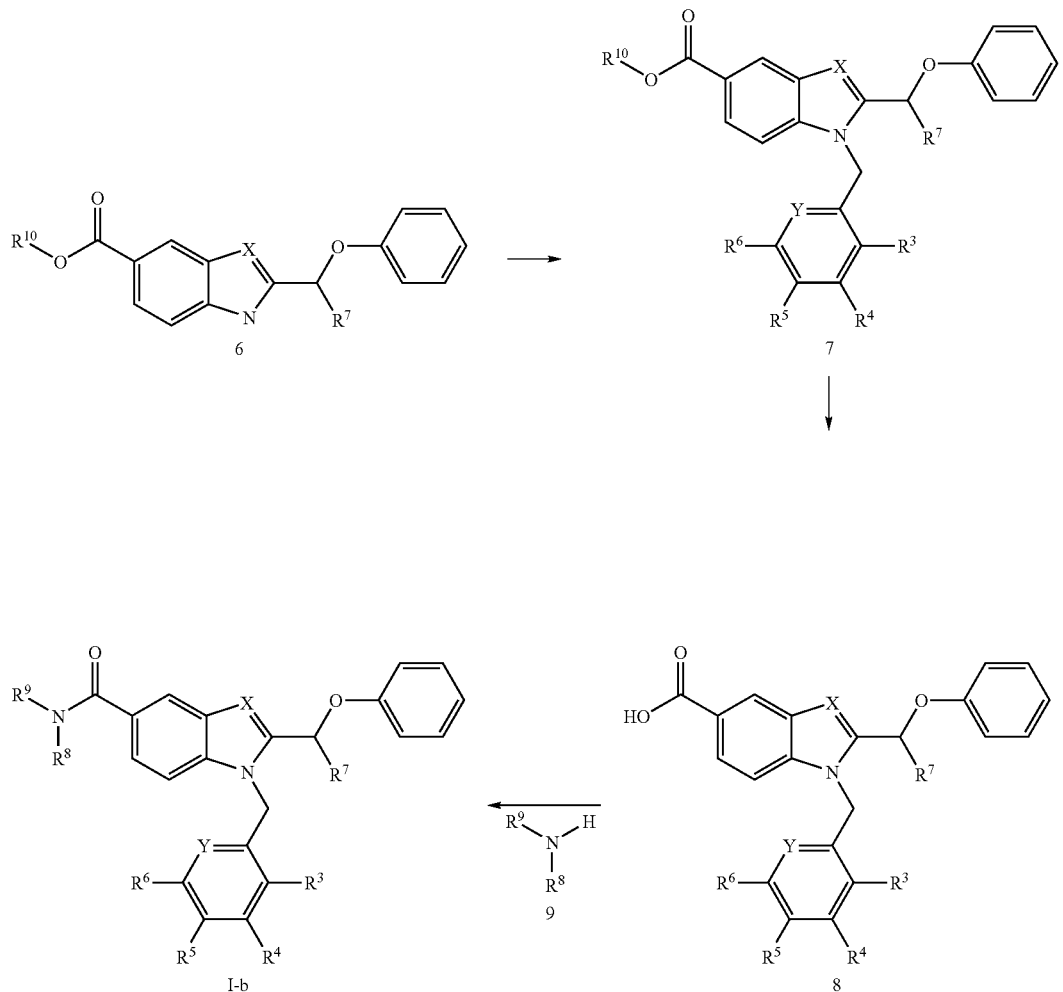

Scheme 2

The indole or benzimidazole derivative of formula 6 can be alkylated with an appropriate benzylbromide or pyridylmethylbromide with the help of a strong base such as sodium hydroxide (NaOH), potassium hydroxide KOH or, preferably, sodium hydride, to yield a compound of formula 7. The reaction can be carried out in a solvent like THF or dioxane at a temperature of 0° C.

Optionally, the ester of formula 7, wherein $R^{10}$ signifies $C_{1-7}$-alkyl, can be transformed into the respective carboxylic acid by heating it with a 1M NaOH or 1M KOH solution. We find it convenient to use dioxane as a solvent and a temperature of 50° C. for several hours. The carboxylic acids of formula 8 can conveniently be transformed to the respective amide through coupling with an amine 9 wherein $R^8$ and $R^9$ formula 11. The resin is suspended in a compatible solvent like pyridine, dichloromethane, THF or DMF. Conveniently, the ester of formula 10 is added to the suspension, the mixture is stirred for several hours at a temperature of 50° C. and the resin is subsequently washed with methylenchloride and isopropanol.

In the next step, the resin bound ester of formula 11 is reacted with the respective phenyl propargyl ether in the presence of a base such as triethylamine and catalytic amounts of CuI and bis(triphenylphosphine)palladium(II) chloride to obtain the resin bound indole of formula 12 which is finally cleaved from the resin by treating it with tetra-N-butylammoniumfluoride (TBAF) in a solvent like THF at a temperature of 70° C. for several hours.

Scheme 3

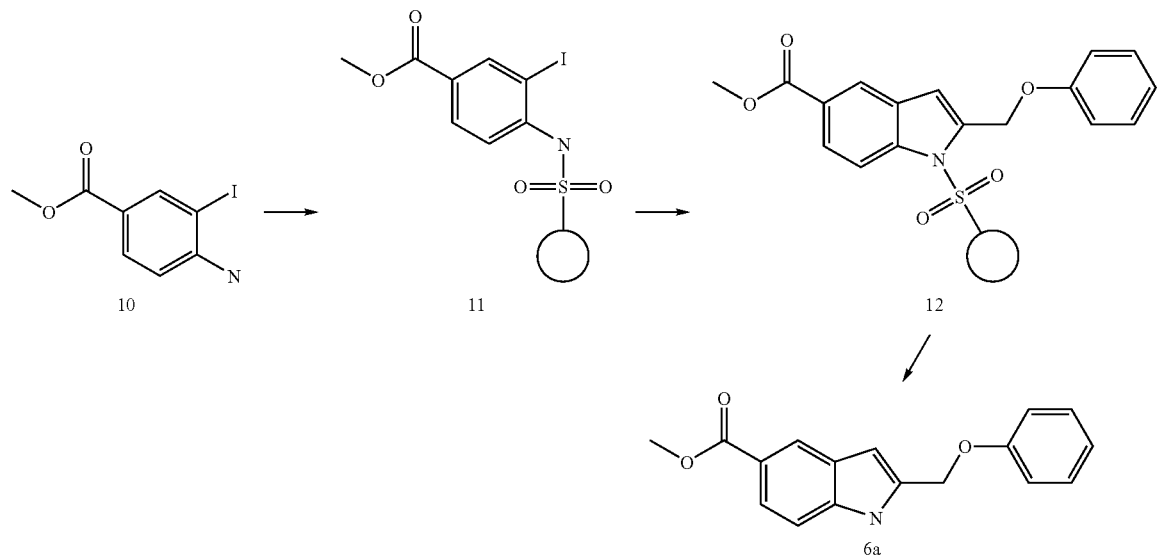

The synthesis of compounds with the general structure I, particularly compounds according to formula I-c, wherein X is N and wherein $R^1$ is —C(O)—$NR^8R^9$ or —C(O)—$OR^{10}$ and $R^2$ is hydrogen, can be accomplished according to Scheme 4.

Fluoro-3-nitro-benzoic acid allyl ester (14) is prepared by transferring 4-fluoro-3-nitrobenzoic acid (13) with cesium carbonate in ethanol into the cesium salt. The cesium salt is then dissolved in DMF and reacted with allylbromide. The reaction can be carried out by room temperature.

In the following step, 14 is substituted with an appropriate benzylamine or pyridylmethylamine (commercially available or accessible by methods described in references or by methods known in the art, as appropriate). The reaction can be carried out at room temperature in a polar organic solvent like ethanol.

Scheme 3

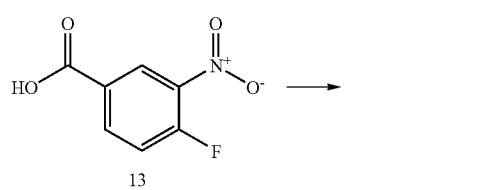

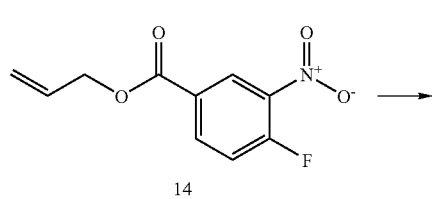

-continued

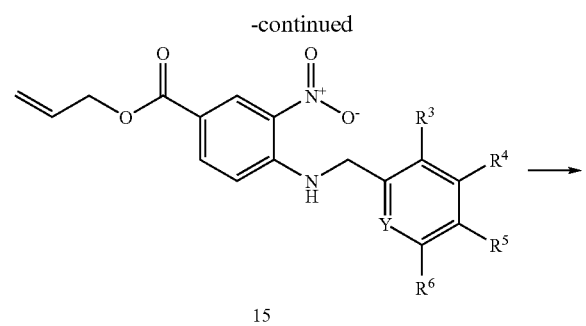

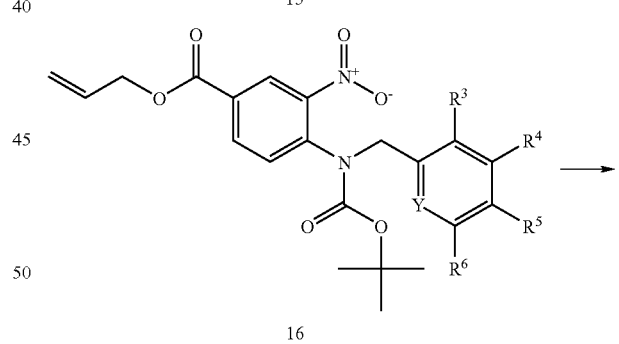

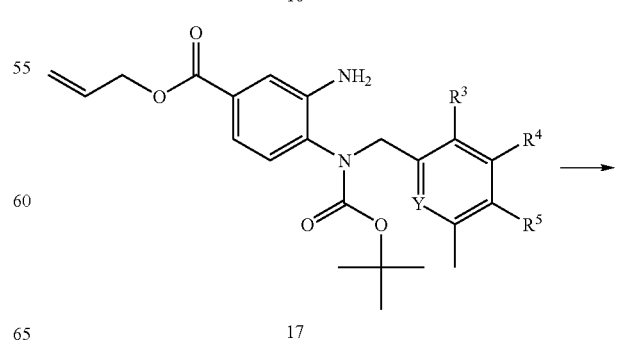

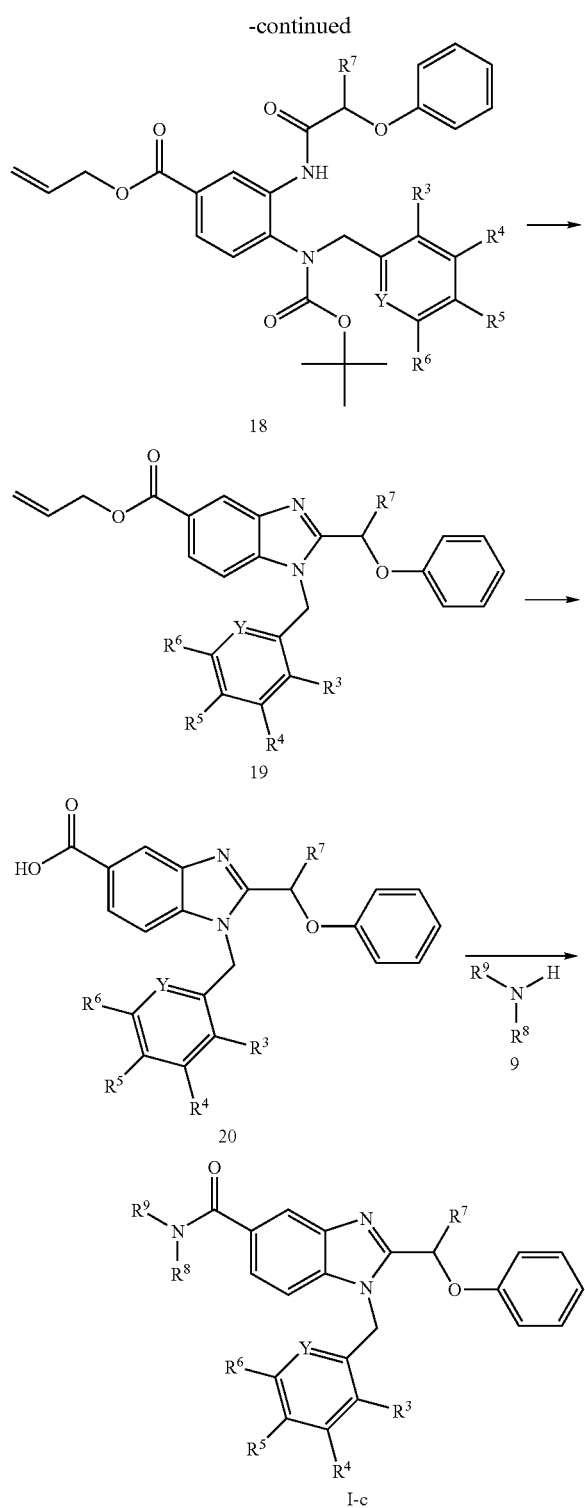

In the following step the nitro group of the compound of formula 16 is reduced with tin(II)chloride dihydrate in DMF to yield the corresponding amine of formula 17, which is then transformed to an amide of formula 18 by adding phenoxyacetic acid or 2-alkyl-2-phenoxyacetic acid, respectively, and diisopropylcarbodiimide as a coupling agent. The reaction can be carried out at room temperature and in an inert solvent like dichloromethane. Cyclization to the benzimidazole derivative 19 can be carried under acidic conditions. We find it convenient to dissolve the compound of formula 18 in a polar organic solvent like methanol, to add 4N HCl in dioxane and to stir the solution for several hours at a temperature of 40° C.

The cleavage of the allylester group can be carried out by methods known in the art, for example by using a reagent such as tetrakis(triphenylphosphine)palladium(0) and morpholine as a base in an inert solvent like dichloromethane. The carboxylic acids of formula 20 can conveniently be transformed to the respective amide of formula I-c through coupling with an amine 9 wherein $R^8$ and $R^9$ are defined herein before (either commercially available or accessible by methods described in references or by methods known in the art) by using a coupling agent such as diisopropylcarbodiimide (DIC).

Some compounds of formula I may possess asymmetric centers and are therefore capable of existing in more than one stereoisomeric form. The invention thus also relates to compounds in substantially pure isomeric form at one or more asymmetric centers as well as mixtures, including racemic mixtures, thereof. Such isomers may be prepared by asymmetric synthesis, for example using chiral intermediates, or mixtures may be resolved by conventional methods, e.g., chromatography (chromatography with a chiral adsorbens or eluent), or use of a solving agent. It will be appreciated, that the compounds of general formula I in this invention may be derivatized at functional groups to provide derivatives which are capable of conversion back to the parent compound in vivo.

As described above, the compounds of formula I or pharmaceutically acceptable salts thereof can be used as medicaments for the treatment and/or prophylaxis of diseases which are associated with the modulation of the CB1 receptors.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are associated with the modulation of CB1 receptors.

In another embodiment, the invention relates to a method for the treatment and/or prophylaxis of diseases which are associated with the modulation of CB1 receptors, which method comprises administering a compound as defined above to a human being or animal.

The invention further relates to the use of compounds as defined above for the treatment and/or prophylaxis of diseases which are associated with the modulation of CB1 receptors.

In addition, the invention relates to the use of compounds as defined above for the preparation of medicaments for the treatment and/or prophylaxis of diseases which are associated with the modulation of CB1 receptors. Such medicaments comprise a compound as defined above.

In this context, the expression 'diseases associated with modulation of CB1 receptors' means diseases which can be treated and/or prevented by modulation of CB1 receptors.

The amine of formula 15 is then protected with an amino protecting group (PG), for example a tert-butyloxycarbonyl group (BOC), an allyloxycarbonyl group or a benzyloxycarbonyl group (Z). Preferably, a tert-butyloxycarbonyl group (BOC) is introduced by methods known in the art, for example by using di-tert-butyl-dicarbonate in the presence of diisopropylamine and dimethylaminopyridine (DMAP).

Such diseases encompass, but are not limited to, psychic disorders, especially anxiety, psychosis, schizophrenia, depression, abuse of psychotropes, for example for the abuse and/or dependence of a substances, including alcohol dependency and nicotine dependency, neuropathies, multiple sclerosis, migraine, stress, epilepsy, dyskinesias, Parkinson's disease, amnesia, cognitive disorders, memory deficits, senile dementia, Alzheimer's disease, eating disorders, obesity, diabetes type II or non insulin dependent diabetes (NIDD), gastrointestinal diseases, vomiting, diarrhea, urinary disorders, cardiovascular disorders, infertility disorders, inflammations, asthma, infections, cancer, neuroinflammation, in particular in atherosclerosis, or the Guillain-Barré syndrome, viral encephalitis, cerebral vascular incidents and cranial trauma.

In a preferable aspect, the expression "diseases associated with modulation of CB1 receptors" relates to eating disorders, obesity, diabetes type II or non insulin dependent diabetes (NIDD), neuroinflammation, diarrhea, abuse and/or dependence of a substances, including alcohol dependency and nicotine dependency. In a more preferable aspect, the said term related to eating disorders, obesity, diabetes type II or non insulin dependent diabetes (NIDD), abuse and/or dependence of a substances, including alcohol dependency and nicotine dependency, with obesity being especially preferred.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is orlistat. Also an embodiment of the invention is the method as described above for the simultaneous, separate or sequential administration of a compound according to formula I and a lipase inhibitor, particularly tetrahydrolipstatin.

It is a further preferred embodiment to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include but are not limited to anorectic agents, lipase inhibitors and selective serotonin reuptake inhibitors (SSRI). Combinations or associations of the above agents may be encompassing separate, sequential or simultaneous administration.

Preferable lipase inhibitor is tetrahydrolipstatin.

Suitable anorectic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine, and pharmaceutically acceptable salts thereof.

Most preferable anorectic agents are sibutramine and phentermine.

Suitable selective serotonin reuptake inhibitors of use in combination with a compound of the present invention include: fluoxetine, fluvoxamine, paroxetine and sertraline, and pharmaceutically acceptable salts thereof.

It is a further preferred embodiment to provide a method of treatment or prevention of Type II diabetes (non-insulin dependent diabetes mellitus (NIDDM) in a human which comprises administration of a therapeutically effective amount of a compound according to formula I in combination or association with a therapeutically effective amount of an anti-diabetic agent selected from the group consisting of 1) PPARγ agonists such as pioglitazone or rosiglitazone, and the like; 2) biguanides such as metformin, and the like; 3) sulfonylureas such as glibenclamide, and the like; 4) PPARα/γ agonists such as GW-2331, and the like 5) DPP-IV-inhibitors such as LAF-237 (Vildagliptin) or MK-0431, and the like; 6) Glucokinase activators such as the compounds disclosed in e.g. WO 00/58293 A1, and the like. Also an embodiment of the invention is the method as described above for the simultaneous, separate or sequential administration of a compound according to formula I and a therapeutically effective amount of an anti-diabetic agent as 1) PPARγ agonists such as pioglitazone or rosiglitazone, and the like; 2) biguanides such as metformin, and the like; 3) sulfonylureas such as glibenclamide, and the like; 4) PPARα/γ agonists such as GW-2331 GW-2331 and the like; 5) DPP-IV-inhibitors such as LAF-237 (Vildagliptin) or MK-0431, and the like; 6) Glucokinase activators such as the compounds disclosed in e.g. WO 00/58293 A1, and the like.

It is a further preferred embodiment to provide a method of treatment or prevention of dyslipidemias in a human which comprises administration of a therapeutically effective amount of a compound according to formula I in combination or association with a therapeutically effective amount of a lipid lowering agent as 1) bile acid sequestrants such as cholestyramine, and the like; 2) HMG-CoA reductase inhibitors such as atorvastatin, and the like; 3) cholesterol absorption inhibitors such as ezetimibe, and the like; 4) CETP inhibitors such as torcetrapib, JTT 705, and the like; 5) PPARα-agonists such as beclofibrate, fenofibrate, and the like; 6) lipoprotein synthesis inhibitors such as niacin, and the like; and 7) niacin receptor agonists. Also an embodiment of the invention is the method as described above for the simultaneous, separate or sequential administration of a compound according to formula I and a therapeutically effective amount of a lipid lowering agent as 1) bile acid sequestrants such as cholestyramine, and the like; 2) HMG-CoA reductase inhibitors such as atorvastatin, and the like; 3) cholesterol absorption inhibitors such as ezetimibe, and the like; 4) CETP inhibitors such as torcetrapib, JTT 705, and the like; 5) PPARα-agonists such as beclofibrate, fenofibrate, and the like; 6) lipoprotein synthesis inhibitors such as niacin, and the like; and 7) niacin receptor agonists.

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

In addition, to demonstrate CNS activities of the compounds of the present invention, the following in vivo assays may be used.

Method for Testing Task Learning and Spatial Memory

The Morris Water Maze is routinely used to assess task learning and spatial memory (Jaspers et al., Neurosci. Lett. 117:149-153, 1990; Morris, J. Neurosci. Methods 11:47-60, 1984). In this assay, animals are placed in a water pool which is divided into quadrants. One platform is hidden in one of the quadrants. The animal is placed in the water pool and is expected to locate the hidden platform within a predetermined time. During a number of training trials, the animal learns the location of the platform and escape from the pool. The animal receives multiple trials in this task. Total distance traveled, number of trials to locate platform, latency to find platform, and the swimming path is recorded for each animal. The animal's learning ability is measured by the length of time or number of trials required to find the hidden platform. Memory deficit or improvement is determined by the number of trials or the latency to find the platform at predetermined delay time after acquisition. Leaning and memory may be measured by the number of times that the animal crosses the quadrant where the platform was located during the acquisition phase.

Method for Testing Drug Dependence

Self-administration in animals is a predictor of a compound's abuse potential in humans. Modifications to this procedure may also be used to identify compounds that prevent or block the reinforcing properties of drugs that have abuse potential. A compound that extinguishes the self-administration of a drug may prevent that drug's abuse or its dependence. (Ranaldi et al., Psychopharmacol. 161:442-448, 2002; Campbell et al., Exp. Clin. Psychopharmacol. 8:312-25, 2000). In a self-administration test, animals are placed in the operant chambers containing both an active and inactive lever. Each response on the active lever produces an infusion of either the test compound or a drug known to be self-administered. Presses on the inactive lever have no effect, but are also recorded. Animals are then trained to self-administer compound/drug over a set period of time by having drug access during each daily session. Illumination of the chamber house light signals the beginning of the session and the availability of the compound/drug. When the session ends, the house light is turned off. Initially, a drug infusion occurs with every press of the active lever. Once lever-pressing behavior has been established, the number of presses to produce a drug infusion is increased. After stable compound/drug self-administration is obtained, the effect of a second compound on the drug-reinforced behavior may be evaluated. Administration of this second compound prior to the session can either potentiate, extinguish, or produce no change to the self-administrating behavior.

Furthermore the utility of compounds of formula I in diseases or disorders may be demonstrated in animal disease models that have been reported in the literature. The following are examples of such animal disease models: a) reduction of sweet food intake in marmosets (Behavioural Pharm, 1998, 9,179-181); b) reduction of sucrose and ethanol intake in mice (Psychopharm. 1997, 132, 104-106); c) increased motor activity and place conditioning in rats (Psychopharm. 1998, 135, 324-332; Psychopharmacol 2000, 151: 25-30); d) spontaneous locomotor activity in mice (J. Pharm. Exp. Ther. 1996, 277, 586-594); e) reduction in opiate self-administration in mice (Sci. 1999, 283, 401-404).

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following examples serve to illustrate the present invention in more detail. They are, however, not intended to limit its scope in any manner.

EXAMPLES

MS=mass spectrometry; ISP=ion spray (positive ion), corresponds to ESI (electrospray, positive ion); mp=melting point; DCM=dichloromethane, DIC=N,N'-Diisopropylcarbodiimide, DIPEA=diisopropylamine, DMF=dimethylformamide, DMSO=dimethylsulfoxide, EDCI=1-ethyl-3(3'-dimethylaminopropyl)carbodiimide; HOBt=N-hydroxy-1,2,3-benzotriazole, TEA=triethylamine, TBAF=tetra-N-butylammoniumfluoride, TBTU=-(Benzotriazol-1-yl)-N,N',N'-tetramethyl-uronium-tetrafluoroborate.

Example 1

6-(4-Methanesulfonyl-piperazin-1-yl)-2-phenoxymethyl-1-(4-trifluoromethoxy-benzyl)-1-H-benzoimidazole Step 1:

4-(3-Amino-4-nitro-phenyl)-piperazine-1-carboxylic acid tert-butyl ester

A mixture of 2 g (11.6 mmol) 5-chloro-2-nitro-phenylamine, 2.14 g (11.6 mmol) piperazine-1-carboxylic acid tert-butyl ester and 1.3 g (11.6 mmol) 1,4-diazo-bicyclo[2.2.2]octane in 20 ml DMSO was heated to 150° C. for 16 h. The mixture was poured onto 200 ml water and extracted with 250 ml ethyl acetate. The emulsion was filtered through decalite and the aqueous phase was extracted with 2×200 ml. The combined organic phases were washed with 2×100 ml water, dried with $MgSO_4$ and evaporated to dryness. The residue was purified with column chromatography on silica eluting with ethyl acetate/hexane to yield the title compound as a yellow solid. MS(ISP): 321.2 (M–H)$^-$.

Step 2:

4-[4-Nitro-3-(2-phenoxy-acetylamino)-phenyl]-piperazine-1-carboxylic acid tert-butyl ester A mixture of 1 g (3.1 mmol) 4-(3-amino-4-nitro-phenyl)-piperazine-1-carboxylic acid tert-butyl ester, 0.793 g (4.65 mmol) phenoxyacetyl chloride and 2.2 g (21.7 mmol) triethylamine in 20 ml THF was stirred at room temperature for 30 min. The mixture was evaporated and 100 ml DCM were added. The organic phase was washed with 2×50 ml 0.1 M $Na_2CO_3$ aq. The combined aqueous phase was extracted with 2×100 ml DCM. The combined organic phases were dried with $MgSO_4$ and evaporated to dryness. The residue was purified over silica eluting with ethyl acetate/hexane 1/1 to yield 1.15 g (81%) of the title compound as yellow solid. MS(ISP): 455.3 (M–H)$^-$.

Step 3:

4-{4-Nitro-3-[(2-phenoxy-acetyl)-(4-trifluoromethoxy-benzyl)-amino]-phenyl}-piperazine-1-carboxylic acid tert-butyl ester A mixture of 1 g (2.19 mmol) 4-[4-nitro-3-(2-phenoxy-acetylamino)-phenyl]-piperazine-1-1-carboxylic acid tert-butyl ester, 1.07 g (3.29 mmol) cesiumcarbonate and 0.79 g (3.29 mmol) 4-(trifluoromethoxy)benzyl bromide (commercially available) in 6.6 ml DMF was stirred at 110° C. for 2 h. After cooling to room temperature the precipitate was filtered of. The residue was used without further purification. The title compound was isolated as brown solid (0.39 g; 37%). MS(ISP): 631.5 (M+H)$^+$ Step 4:

2-Phenoxymethyl-6-piperazin-1-yl-1-(4-trifluoromethoxy-benzyl)-H-benzoimidazole

A mixture of 390 mg (0.62 mmol) 4-{4-nitro-3-[(2-phenoxy-acetyl)-(4-trifluo-methoxy-benzyl)-amino]-phenyl}-piperazine-1-carboxylic acid tert-butyl ester, 837 mg (3.7 mmol) tin(II)-chloride dehydrate and 3.7 ml 1N HCl aq. in 10 ml DMF was heated to 110° C. for 2.5 h. The mixture was treated with 2N $Na_2CO_3$ until basic and extracted with 3×100 ml ethyl acetate. The combined organic phases were washed with 2×50 ml water, dried with $MgSO_4$ and evaporated to dryness. The title compound was used without further purification in the consecutive step. Yellow solid; MS(ISP): 483.4 (M+H)$^+$.

Step 5:

A mixture of 48.3 mg (0.1 mmol) 2-phenoxymethyl-6-piperazin-1-yl-1-(4-trifluoromethoxy-benzyl)-H-benzimidazole, 17.2 mg (0.15 mmol) methanesulfonyl chloride and 101 mg (1 mmol) triethylamine in 1 ml DCM was stirred at room temperature for 1 h. After evaporation of all volatiles the residue was taken up in acetonitrile/DMF and purified by preparative HPLC on reversed phase eluting with a gradient of acetonitrile/water. After evaporation of the product fractions 4.2 mg of the title compound was isolated. MS(ISP): 560.2 (M+H)$^+$.

Intermediate 1

2-Phenoxymethyl-6-piperazin-1-yl-1-(4-trifluoromethyl-benzyl)-1H-benzoimidazole

Step 1:

4-{4-Nitro-3-[(2-phenoxy-acetyl)-(4-trifluoromethyl-benzyl)-amino]-phenyl}-piperazine-1-carboxylic acid tert-butyl ester According to the procedure described for the synthesis of Example 1/step 3 (4-{4-nitro-3-[(2-phenoxy-acetyl)-(4-trifluoromethoxy-benzyl)-amino]-phenyl}-piperazine-1-carboxylic acid tert-butyl ester) the title compound was synthesized from 4-[4-nitro-3-(2-phenoxy-acetylamino)-phenyl]-piperazine-1-carboxylic acid tert-butyl ester and 4-trifluoromethoxybenzyl bromide (commercially available) in 42% yield. MS(ISP): 614.6 (M+H)$^+$.

Step 2:

According to the procedure described for the synthesis of Example 1/step 4 (2-phenoxymethyl-6-piperazin-1-yl-1-(4-trifluoromethoxy-benzyl)-H-benzoimidazole) the title compound was synthesized from 4-{4-nitro-3-[(2-phenoxy-acetyl)-(4-trifluoromethyl-benzyl)-amino]-phenyl}-piperazine-1-carboxylic acid tert-butyl ester under reductive conditions and used without further purification in the consecutive step. MS(ISP): 483.4(M+H)$^+$.

Intermediate 2

Benzyl-2-phenoxymethyl-6-piperazin-1-yl-1H-benzoimidazole

Step 1:

4-{3-[Benzyl-(2-phenoxy-acetyl)-amino]-4-nitro-phenyl}-piperazine-1-carboxylic acid tert-butyl ester According to the procedure described for the synthesis of Example 1/step 3 (4-{4-nitro-3-[(2-phenoxy-acetyl)-(4-trifluoromethoxy-benzyl)-amino]-phenyl}-piperazine-1-carboxylic acid tert-butyl ester) the title compound was synthesized from 4-[4-nitro-3-(2-phenoxy-acetylamino)-phenyl]-piperazine-1-carboxylic acid tert-butyl ester and benzyl bromide (commercially available) in 84% yield. MS(ISP): 546.6 (M+H)$^+$.

Step 2:

According to the procedure described for the synthesis of Example 1/step 4 (2-phenoxymethyl-6-piperazin-1-yl-1-(4-trifluoromethoxy-benzyl)-H-benzoimidazole) the title compound was synthesized from 4-[4-nitro-3-(2-phenoxy-acetylamino)-phenyl]-piperazine-1-carboxylic acid tert-butyl ester under reductive conditions and used without further purification in the consecutive step. MS(ISP): 399.5 (M+H)$^+$.

According to the procedure described for the synthesis of Example 1/step 5 further benzimidazole-derivatives have been synthesized from 2-phenoxymethyl-6-piperazin-1-yl-1-(4-trifluoromethoxy-benzyl)-H-benzoimidazole, 2-phenoxymethyl-6-piperazin-1-yl-1-(4-trifluoromethyl-benzyl)-1H-benzoimidazole or 1-benzyl-2-phenoxymethyl-6-piperazin-1-yl-1H-benzoimidazole and the respective carboxylic acid chloride or the respective sulfonyl chloride as indicated in table 1. The results are compiled in table 1 and comprise example 2 to example 20.

TABLE 1

| No. | MW | Name | Starting materials | (M + H)$^+$ found |
|---|---|---|---|---|
| 2 | 602.2 | 6-[4-(butane-1-sulfonyl)-piperazin-1-yl]-2-phenoxymethyl-1-(4-trifluoromethoxy-benzyl)-1H-benzoimidazole | 2-phenoxymethyl-6-piperazin-1-yl-1-(4-trifluoromethoxy-benzyl)-1H-benzoimidazole and butane-1-sulfonyl chloride (commercially available) | 603.3 |
| 3 | 589.2 | 4-[2-phenoxymethyl-3-(4-trifluoromethoxy-benzyl)-3H-benzoimidazol-5-yl]-piperazine-1-sulfonic acid dimethylamide | 2-phenoxymethyl-6-piperazin-1-yl-1-(4-trifluoromethoxy-benzyl)-1H-benzoimidazole and dimethylaminosulfamoyl chloride (commercially available) | 590.4 |
| 4 | 622.2 | 6-(4-benzenesulfonyl-piperazin-1-yl)-2-phenoxymethyl-1-(4-trifluoromethoxy-benzyl)-1H-benzoimidazole | 2-phenoxymethyl-6-piperazin-1-yl-1-(4-trifluoromethoxy-benzyl)-1H-benzoimidazole and benzenesulfonyl chloride (commercially available) | 623.4 |
| 5 | 636.2 | 2-phenoxymethyl-6-(4-phenylmethanesulfonyl-piperazin-1-yl)-1-(4-trifluoromethoxy-benzyl)-1H-benzoimidazole | 2-phenoxymethyl-6-piperazin-1-yl-1-(4-trifluoromethoxy-benzyl)-1H-benzoimidazole and phenyl-methanesulfonyl chloride (commercially available) | 637.4 |
| 6 | 636.2 | 2-phenoxymethyl-6-[4-(toluene-2-sulfonyl)-piperazin-1-yl]-1-(4-trifluoromethoxy-benzyl)-1H-benzoimidazole | 2-phenoxymethyl-6-piperazin-1-yl-1-(4-trifluoromethoxy-benzyl)-1H-benzoimidazole and 2-methylbenzenesulfonyl chloride (commercially available) | 637.3 |
| 7 | 524.3 | 1-{4-[2-phenoxymethyl-3-(4-trifluoromethoxy-benzyl)-3H-benzoimidazol-5-yl]-piperazin-1-yl}-ethanone | 2-phenoxymethyl-6-piperazin-1-yl-1-(4-trifluoromethoxy-benzyl)-1H-benzoimidazole and acetyl chloride (commercially available) | 525.3 |
| 8 | 538.2 | 1-{4-[2-phenoxymethyl-3-(4-trifluoromethoxy-benzyl)-3H-benzoimidazol-5-yl]-piperazin-1-yl}-propan-1-one | 2-phenoxymethyl-6-piperazin-1-yl-1-(4-trifluoromethoxy-benzyl)-1H-benzoimidazole and propionyl chloride (commercially available) | 539.2 |
| 9 | 566.3 | 1-{4-[2-phenoxymethyl-3-(4-trifluoromethoxy-benzyl)-3H-benzoimidazol-5-yl]-piperazin-1-yl}-pentan-1-one | 2-phenoxymethyl-6-piperazin-1-yl-1-(4-trifluoromethoxy-benzyl)-1H-benzoimidazole and pentanoyl chloride (commercially available) | 567.4 |
| 10 | 600.2 | 1-{4-[2-phenoxymethyl-3-(4-trifluoromethoxy-benzyl)-3H-benzoimidazol-5-yl]-piperazin- | 2-phenoxymethyl-6-piperazin-1-yl-1-(4-trifluoromethoxy-benzyl)-1H-benzoimidazole and | 601.3 |

TABLE 1-continued

| No. | MW | Name | Starting materials | (M + H)+ found |
|---|---|---|---|---|
| | | 1-yl}-2-phenyl-ethanone | phenyl-acetyl chloride (commercially available) | |
| 11 | 544.2 | 6-(4-methanesulfonyl-piperazin-1-yl)-2-phenoxymethyl-1-(4-trifluoromethyl-benzyl)-1H-benzoimidazole | 2-phenoxymethyl-6-piperazin-1-yl-1-(4-trifluoromethyl-benzyl)-1H-benzoimidazole and methanesulfonyl chloride (commercially available) | 545.2 |
| 12 | 586.2 | 6-[4-(butane-1-sulfonyl)-piperazin-1-yl]-2-phenoxymethyl-1-(4-trifluoromethyl-benzyl)-1H-benzoimidazole | 2-phenoxymethyl-6-piperazin-1-yl-1-(4-trifluoromethyl-benzyl)-1H-benzoimidazole and butane-1-sulfonyl chloride (commercially available) | 587.4 |
| 13 | 620.2 | 2-phenoxymethyl-6-(4-phenylmethanesulfonyl-piperazin-1-yl)-1-(4-trifluoromethyl-benzyl)-1H-benzoimidazole | 2-phenoxymethyl-6-piperazin-1-yl-1-(4-trifluoromethyl-benzyl)-1H-benzoimidazole and phenyl-methanesulfonyl chloride (commercially available) | 621.3 |
| 14 | 522.2 | 1-{4-[2-phenoxymethyl-3-(4-trifluoromethyl-benzyl)-3H-benzo-imidazol-5-yl]-piperazin-1-yl}-propan-1-one | 2-phenoxymethyl-6-piperazin-1-yl-1-(4-trifluoromethyl-benzyl)-1H-benzoimidazole and propionyl chloride (commercially available) | 523.2 |
| 15 | 550.3 | 1-{4-[2-phenoxymethyl-3-(4-trifluoromethyl-benzyl)-3H-benzo-imidazol-5-yl]-piperazin-1-yl}-pentan-1-one | 2-phenoxymethyl-6-piperazin-1-yl-1-(4-trifluoromethyl-benzyl)-1H-benzoimidazole and pentanoyl chloride (commercially available) | 551.3 |
| 16 | 570.2 | {4-[2-phenoxymethyl-3-(4-trifluoromethyl-benzyl)-3H-benzo-imidazol-5-yl]-piperazin-1-yl}-phenyl-methanone | 2-phenoxymethyl-6-piperazin-1-yl-1-(4-trifluoromethyl-benzyl)-1H-benzoimidazole and benzoylchloride (commercially available) | 571.3 |
| 17 | 584.2 | 1-{4-[2-phenoxymethyl-3-(4-trifluoromethyl-benzyl)-3H-benzoimidazol-5-yl]-piperazin-1-yl}-2-phenyl-ethanone | 2-phenoxymethyl-6-piperazin-1-yl-1-(4-trifluoromethyl-benzyl)-1H-benzoimidazole and phenyl-acetyl chloride (commercially available) | 585.2 |
| 18 | 584.2 | {4-[2-phenoxymethyl-3-(4-trifluoromethyl-benzyl)-3H-benzo-imidazol-5-yl]-piperazin-1-yl}-o-tolyl-methanone | 2-phenoxymethyl-6-piperazin-1-yl-1-(4-trifluoromethyl-benzyl)-1H-benzoimidazole and o-tolyl-acetyl chloride (commercially available) | 585.3 |
| 19 | 502.2 | [4-(3-benzyl-2-phenoxymethyl-3H-benzoimidazol-5-yl)-piperazin-1-yl]-phenyl-methanone | 1-benzyl-2-phenoxymethyl-6-piperazin-1-yl-1H-benzoimidazole and benzoyl chloride (commercially available) | 503.5 |
| 20 | 516.3 | [4-(3-benzyl-2-phenoxymethyl-3H-benzoimidazol-5-yl)-piperazin-1-yl]-o-tolyl-methanone | 1-benzyl-2-phenoxymethyl-6-piperazin-1-yl-1H-benzoimidazole and o-tolyl-acetyl chloride (commercially available) | 517.4 |

Example 21

6-(4-Methanesulfonyl-piperazin-1-yl)-2-(1-phenoxy-ethyl)-1-(4-trifluoromethoxy-benzyl)-1H-benzoimidazole Step 1:

4-[4-Nitro-3-(2-phenoxy-propionylamino)-phenyl]-piperazine-1-carboxylic acid tert-butyl ester According to the procedure described for the synthesis of Example 1/step 2 (4-[4-nitro-3-(2-phenoxy-acetylamino)-phenyl]-piperazine-1-carboxylic acid tert-butyl ester) the title compound was synthesized from 4-(3-amino-4-nitro-phenyl)-piperazine-1-carboxylic acid tert-butyl ester and 2-phenoxy-propionyl chloride in 95% yield.

Step 2:

4-{4-Nitro-3-[(2-phenoxy-propionyl)-(4-trifluoromethoxy-benzyl)-amino]-phenyl}-piperazine-1-carboxylic acid tert-butyl ester According to the procedure described for the synthesis of Example 1/step 3 (4-{4-nitro-3-[(2-phenoxy-acetyl)-(4-trifluoromethoxy-benzyl)-amino]-phenyl}-piperazine-1-carboxylic acid tert-butyl ester) the title compound was synthesized from 4-[4-nitro-3-(2-phenoxy-propionylamino)-phenyl]-piperazine-1-carboxylic acid tert-butyl ester and 4-trifluoromethoxybenzyl bromide (commercially available) in 85.4% yield. MS(ISP): 645.1 (M+H)+.

Step 3:

2-(1-Phenoxy-ethyl)-6-piperazin-1-yl-1-(4-trifluoromethoxy-benzyl)-H-benzoimidazole According to the procedure described for the synthesis of Example 1/step 4 (2-phenoxymethyl-6-piperazin-1-yl-1-(4-trifluoromethoxy-benzyl)-H-benzoimidazole) the title compound was synthesized from 4-{4-nitro-3-[(2-phenoxy-propionyl)-(4-trifluoromethoxy-benzyl)-amino]-phenyl}-piperazine-1-carboxylic acid tert-butyl ester under reductive conditions and used without further purification in the consecutive step. MS(ISP): 497.3 (M+H)+.

Step 4:

According to the procedure described for the synthesis of Example 1/step 5 (6-(4-methanesulfonyl-piperazin-1-yl)-2-phenoxymethyl-1-(4-trifluoromethoxy-benzyl)-1H-benzoimidazole) the title compound was synthesized in 12.5% yield from 2-(1-phenoxy-ethyl)-6-piperazin-1-yl-1-(4-trifluoromethoxy-benzyl)-H-benzoimidazole and methanesulfonyl chloride (commercially available). MS(ISP): 497.3 (M+H)+.

Intermediate 3

2-(1-Phenoxy-ethyl)-6-piperazin-1-yl-1-(4-trifluoromethyl-benzyl)-1H-benzoimidazole Step 1:

4-{4-Nitro-3-[(2-phenoxy-propionyl)-(4-trifluoromethyl-benzyl)-amino]-phenyl}-piperazine-1-carboxylic acid tert-butyl ester According to the procedure described for the synthesis of Example 20/step 2 (4-{4-nitro-3-[(2-phenoxy-propionyl)-(4-trifluoromethoxy-benzyl)-amino]-phenyl}-piperazine-1-carboxylic acid tert-butyl ester) the title compound was synthesized from 4-[4-nitro-3-(2-phenoxy-propionylamino)-phenyl]-piperazine-1-carboxylic acid tert-butyl ester and 4-trifluoromethyl-benzyl bromide (commercially available) in 91.2% yield. MS(ISP): 629.0 (M+H)+.

Step 2:

According to the procedure described for the synthesis of Example 20/step 3 (2-(1-phenoxy-ethyl)-6-piperazin-1-yl-1-(4-trifluoromethoxy-benzyl)-H-benzoimidazole) the title compound was synthesized from 4-{4-nitro-3-[(2-phenoxy-propionyl)-(4-trifluoromethyl-benzyl)-amino]-phenyl}-piperazine-1-carboxylic acid tert-butyl ester under reductive conditions and used without further purification in the consecutive step. MS(ISP): 481.4 (M+H)+.

Intermediate 4

Benzyl-2-(1-phenoxy-ethyl)-6-piperazin-1-yl-1H-benzoimidazole

Step 1:

4-{3-[Benzyl-(2-phenoxy-propionyl)-amino]-4-nitro-phenyl}-piperazine-1-carboxylic acid tert-butyl ester According to the procedure described for the synthesis of Example 20/step 2 (4-{4-Nitro-3-[(2-phenoxy-propionyl)-(4-trifluoromethoxy-benzyl)-amino]-phenyl}-piperazine-1-carboxylic acid tert-butyl ester) the title compound was synthesized from 4-[4-nitro-3-(2-phenoxy-propionylamino)-phenyl]-piperazine-1-carboxylic acid tert-butyl ester and benzyl bromide (commercially available) in 51% yield. MS(ISP): 561.0 (M+H)+.

Step 2:

According to the procedure described for the synthesis of Example 20/step 3 (2-(1-phenoxy-ethyl)-6-piperazin-1-yl-1-(4-trifluoromethoxy-benzyl)-H-benzoimidazole) the title compound was synthesized from 4-{3-[benzyl-(2-phenoxy-propionyl)-amino]-4-nitro-phenyl}-piperazine-1-carboxylic acid tert-butyl ester under reductive conditions and used without further purification in the consecutive step. MS(ISP): 413.4 (M+H)+.

Intermediate 5

1-(4-Chloro-benzyl)-2-(1-phenoxy-ethyl)-6-piperazin-1-yl-1H-benzoimidazole

Step 1:

4-{3-[(4-Chloro-benzyl)-(2-phenoxy-propionyl)-amino]-4-nitro-phenyl}-piperazine-1-carboxylic acid tert-butyl ester According to the procedure described for the synthesis of Example 20/step 2 (4-{4-nitro-3-[(2-phenoxy-propionyl)-(4-trifluoromethoxy-benzyl)-amino]-phenyl}-piperazine-1-carboxylic acid tert-butyl ester) the title compound was synthesized from 4-[4-nitro-3-(2-phenoxy-propionylamino)-phenyl]-piperazine-1-carboxylic acid tert-butyl ester and 4-chlorobenzyl bromide (commercially available) in 53% yield. MS(ISP): 595.0 (M+H)+.

Step 2:

According to the procedure described for the synthesis of Example 20/step 3 (2-(1-phenoxy-ethyl)-6-piperazin-1-yl-1-(4-trifluoromethoxy-benzyl)-H-benzoimidazole) the title compound was synthesized from 4-{3-[(4-chloro-benzyl)-(2-phenoxy-propionyl)-amino]-4-nitro-phenyl}-piperazine-1-carboxylic acid tert-butyl ester under reductive conditions and used without further purification in the consecutive step. MS(ISP): 447.4 (M+H)+.

According to the procedure described for the synthesis of example 20/step 4 further benzoimidazole-derivatives have been synthesized from 2-(1-phenoxy-ethyl)-6-piperazin-1-yl-1-(4-trifluoromethoxy-benzyl)-H-benzoimidazole, 2-(1-phenoxy-ethyl)-6-piperazin-1-yl-1-(4-trifluoromethyl-benzyl)-1H-benzoimidazole, 1-benzyl-2-(1-phenoxy-ethyl)-6-piperazin-1-yl-1H-benzoimidazole or 1-(4-chloro-benzyl)-2-(1-phenoxy-ethyl)-6-piperazin-1-yl-1H-benzoimidazole and the respective carboxylic acid chloride or the respective sulfonyl chloride as indicated in table 2. The results are compiled in table 2 and comprise example 22 to example 59.

TABLE 2

| No. | MW | Name | Starting materials | (M + H)+ |
|---|---|---|---|---|
| 22 | 616.2 | 6-[4-(butane-1-sulfonyl)-piperazin-1-yl]-2-(1-phenoxy-ethyl)-1-(4-trifluoromethoxy-benzyl)-1H-benzoimidazole | 2-(1-phenoxy-ethyl)-6-piperazin-1-yl-1-(4-trifluoromethoxy-benzyl)-1H-benzoimidazole and butane-1-sulfonyl chloride (commercially available) | 617.4 |
| 23 | 603.2 | 4-[2-(1-phenoxy-ethyl)-3-(4-trifluoromethoxy-benzyl)-3H-benzoimidazol-5-yl]-piperazine-1-sulfonic acid dimethylamide | 2-(1-phenoxy-ethyl)-6-piperazin-1-yl-1-(4-trifluoromethoxy-benzyl)-1H-benzoimidazole and dimethylaminosulfamoyl chloride (commercially available) | 604.3 |
| 24 | 650.2 | 2-(1-phenoxy-ethyl)-6-[4-(toluene-2-sulfonyl)-piperazin-1-yl]-1-(4-trifluoromethoxy-benzyl)-1H-benzoimidazole | 2-(1-phenoxy-ethyl)-6-piperazin-1-yl-1-(4-trifluoromethoxy-benzyl)-1H-benzoimidazole and o-Tolyl-acetyl chloride (commercially available) | 651.3 |
| 25 | 538.2 | 1-{4-[2-(1-phenoxy-ethyl)-3-(4-trifluoro-methoxy-benzyl)-3H-benzoimidazol-5-yl]-piperazin-1-yl}-ethanone | 2-(1-phenoxy-ethyl)-6-piperazin-1-yl-1-(4-trifluoromethoxy-benzyl)-1H-benzoimidazole and acetyl chloride (commercially available) | 539.5 |
| 26 | 552.2 | 1-{4-[2-(1-phenoxy-ethyl)-3-(4-trifluoro-methoxy-benzyl)-3H-benzoimidazol-5-yl]-piperazin-1-yl}-propan-1-one | 2-(1-phenoxy-ethyl)-6-piperazin-1-yl-1-(4-trifluoromethoxy-benzyl)-1H-benzoimidazole and propionyl chloride (commercially available) | 553.4 |
| 27 | 594.3 | 1-{4-[2-(1-phenoxy-ethyl)-3-(4-trifluoro-methoxy-benzyl)-3H-benzoimidazol-5-yl]-piperazin-1-yl}-hexan-1-one | 2-(1-phenoxy-ethyl)-6-piperazin-1-yl-1-(4-trifluoromethoxy-benzyl)-1H-benzoimidazole and hexanoyl chloride (commercially available) | 595.3 |
| 28 | 614.3 | {4-[2-(1-phenoxy-ethyl)-3-(4-trifluoromethoxy-benzyl)-3H-benzo-imidazol-5-yl]-piperazin-1-yl}-o-tolyl-methanone | 2-(1-phenoxy-ethyl)-6-piperazin-1-yl-1-(4-trifluoromethoxy-benzyl)-1H-benzoimidazole and o-tolyl-acetyl chloride (commercially available) | 615.4 |
| 29 | 600.2 | 6-[4-(butane-1-sulfonyl)-piperazin-1-yl]-2-(1-phenoxy-ethyl)-1-(4-trifluoromethyl-benzyl)-1H-benzoimidazole | 2-(1-phenoxy-ethyl)-6-piperazin-1-yl-1-(4-trifluoromethyl-benzyl)-1H-benzoimidazole and butane-1-sulfonyl chloride (commercially available) | 601.3 |
| 30 | 587.2 | 4-[2-(1-phenoxy-ethyl)-3-(4-trifluoromethyl-benzyl)-3H-benzo-imidazol-5-yl]-piperazine-1-sulfonic acid dimethylamide | 2-(1-phenoxy-ethyl)-6-piperazin-1-yl-1-(4-trifluoromethyl-benzyl)-1H-benzoimidazole and dimethylaminosulfamoyl chloride (commercially available) | 588.5 |
| 31 | 620.2 | 6-(4-benzenesulfonyl-piperazin-1-yl)-2-(1-phenoxy-ethyl)-1-(4-trifluoromethyl-benzyl)-1H-benzoimidazole | 2-(1-phenoxy-ethyl)-6-piperazin-1-yl-1-(4-trifluoromethyl-benzyl)-1H-benzoimidazole and benzenesulfonyl chloride (commercially available) | 621.3 |
| 32 | 634.2 | 2-(1-phenoxy-ethyl)-6-(4-phenylmethanesulfonyl-piperazin-1-yl)-1-(4-trifluoromethyl-benzyl)-1H-benzoimidazole | 2-(1-phenoxy-ethyl)-6-piperazin-1-yl-1-(4-trifluoromethyl-benzyl)-1H-benzoimidazole and phenyl-methanesulfonyl chloride (commercially available) | 635.3 |
| 33 | 634.2 | 2-(1-phenoxy-ethyl)-6-[4-(toluene-2-sulfonyl)-piperazin-1-yl]-1-(4-trifluoromethyl-benzyl)-1H-benzoimidazole | 2-(1-phenoxy-ethyl)-6-piperazin-1-yl-1-(4-trifluoromethyl-benzyl)-1H-benzoimidazole and 2-methylbenzenesulfonyl chloride (commercially available) | 635.3 |
| 34 | 522.2 | 1-{4-[2-(1-phenoxy-ethyl)-3-(4-trifluoro-methyl-benzyl)-3H- | 2-(1-phenoxy-ethyl)-6-piperazin-1-yl-1-(4-trifluoromethyl-benzyl)-1H- | 523.3 |

TABLE 2-continued

| No. | MW | Name | Starting materials | (M + H)+ |
|---|---|---|---|---|
| | | benzoimidazol-5-yl]-piperazin-1-yl}-ethanone | benzoimidazole and acetyl chloride (commercially available) | |
| 35 | 536.2 | 1-{4-[2-(1-phenoxy-ethyl)-3-(4-trifluoro-methyl-benzyl)-3H-benzoimidazol-5-yl]-piperazin-1-yl}-propan-1-one | 2-(1-phenoxy-ethyl)-6-piperazin-1-yl-1-(4-trifluoromethyl-benzyl)-1H-benzoimidazole and propionyl chloride (commercially available) | 537.4 |
| 36 | 578.3 | 1-{4-[2-(1-phenoxy-ethyl)-3-(4-trifluoro-methyl-benzyl)-3H-benzoimidazol-5-yl]-piperazin-1-yl}-hexan-1-one | 2-(1-phenoxy-ethyl)-6-piperazin-1-yl-1-(4-trifluoromethyl-benzyl)-1H-benzoimidazole and hexanoyl chloride (commercially available) | 579.4 |
| 37 | 584.2 | {4-[2-(1-phenoxy-ethyl)-3-(4-trifluoromethyl-benzyl)-3H-benzo-imidazol-5-yl]-piperazin-1-yl}-phenyl-methanone | 2-(1-phenoxy-ethyl)-6-piperazin-1-yl-1-(4-trifluoromethyl-benzyl)-1H-benzoimidazole and benzoyl chloride (commercially available) | 585.4 |
| 38 | 598.3 | 1-{4-[2-(1-phenoxy-ethyl)-3-(4-trifluoro-methyl-benzyl)-3H-benzoimidazol-5-yl]-piperazin-1-yl}-2-phenyl-ethanone | 2-(1-phenoxy-ethyl)-6-piperazin-1-yl-1-(4-trifluoromethyl-benzyl)-1H-benzoimidazole and phenyl-acetyl chloride (commercially available) | 599.4 |
| 39 | 598.3 | {4-[2-(1-phenoxy-ethyl)-3-(4-trifluoromethyl-benzyl)-3H-benzo-imidazol-5-yl]-piperazin-1-yl}-o-tolyl-methanone | 2-(1-phenoxy-ethyl)-6-piperazin-1-yl-1-(4-trifluoromethyl-benzyl)-1H-benzoimidazole and 2-methylbenzoyl chloride (commercially available) | 599.4 |
| 40 | 532.3 | 1-benzyl-6-[4-(butane-1-sulfonyl)-piperazin-1-yl]-2-(1-phenoxy-ethyl)-1H-benzoimidazole | 1-benzyl-2-(1-phenoxy-ethyl)-6-piperazin-1-yl-1H-benzoimidazole and butane-1-sulfonyl chloride (commercially available) | 533.5 |
| 41 | 519.2 | 4-[3-benzyl-2-(1-phenoxy-ethyl)-3H-benzoimidazol-5-yl]-piperazine-1-sulfonic acid dimethylamide | 1-benzyl-2-(1-phenoxy-ethyl)-6-piperazin-1-yl-1H-benzoimidazole and dimethylaminosulfamoyl chloride (commercially available) | 520.4 |
| 42 | 552.2 | 6(4-benzenesulfonyl-piperazin-1-yl)-1-benzyl-2-(1-phenoxy-ethyl)-1H-benzoimidazole | 1-benzyl-2-(1-phenoxy-ethyl)-6-piperazin-1-yl-1H benzoimidazole and benzenesulfonyl chloride (commercially available) | 553.4 |
| 43 | 566.2 | 1-benzyl-2-(1-phenoxy-ethyl)-6-[4-(toluene-2-sulfonyl)-piperazin-1-yl]-1H-benzoimidazole | 1-benzyl-2-(1-phenoxy-ethyl)-6-piperazin-1-yl-1H benzoimidazole and 2-methylbenzenesulfonyl chloride (commercially available) | 567.4 |
| 44 | 468.3 | 1-{4-[3-benzyl-2-(1-phenoxy-ethyl)-3H-benzoimidazol-5-yl]-piperazin-1-yl}-propan-1-one | 1-benzyl-2-(1-phenoxy-ethyl)-6-piperazin-1-yl-1H-benzoimidazole and propionyl chloride (commercially available) | 469.4 |
| 45 | 510.3 | 1-{4-[3-benzyl-2-(1-phenoxy-ethyl)-3H-benzoimidazol-5-yl]-piperazin-1-yl}-hexan-1-one | 1-benzyl-2-(1-phenoxy-ethyl)-6-piperazin-1-yl-1H-benzo-imidazole and hexanoyl chloride (commercially available) | 511.5 |
| 46 | 516.3 | {4-[3-benzyl-2-(1-phenoxy-ethyl)-3H-benzoimidazol-5-yl]-piperazin-1-yl}-phenyl-methanone | 1-benzyl-2-(1-phenoxy-ethyl)-6-piperazin-1-yl-1H-benzo-imidazole and benzoyl chloride (commercially available) | 517.4 |
| 47 | 530.3 | 1-{4-[3-benzyl-2-(1-phenoxy-ethyl)-3H-benzoimidazol-5-yl]-piperazin-1-yl}-2-phenyl-ethanone | 1-benzyl-2-(1-phenoxy-ethyl)-6-piperazin-1-yl-1H-benzo-imidazole and phenyl-acetyl chloride (commercially available) | 531.4 |
| 48 | 530.3 | {4-[3-benzyl-2-(1-phenoxy-ethyl)-3H- | 1-benzyl-2-(1-phenoxy-ethyl)-6-piperazin-1-yl-1H-benzo- | 531.4 |

TABLE 2-continued

| No. | MW | Name | Starting materials | (M + H)+ |
|---|---|---|---|---|
| | | benzoimidazol-5-yl]-piperazin-1-yl}-o-tolyl-methanone | imidazole and o-tolyl-acetyl chloride (commercially available) | |
| 49 | 524.2 | 1-(4-chloro-benzyl)-6-(4-methanesulfonyl-piperazin-1-yl)-2-(1-phenoxy-ethyl)-1H-benzoimidazole | 1-(4-chloro-benzyl)-2-(1-phenoxy-ethyl)-6-piperazin-1-yl-1H-benzoimidazole and methanesulfonyl chloride (commercially available) | 525.3 |
| 50 | 566.2 | 6-[4-(butane-1-sulfonyl)-piperazin-1-yl]-1-(4-chloro-benzyl)-2-(1-phenoxy-ethyl)-1H-benzoimidazole | 1-(4-chloro-benzyl)-2-(1-phenoxy-ethyl)-6-piperazin-1-yl-1H-benzoimidazole and butane-1-sulfonyl chloride (commercially available) | 567.4 |
| 51 | 553.2 | 4-[3-(4-chloro-benzyl)-2-(1-phenoxy-ethyl)-3H-benzoimidazol-5-yl]-piperazine-1-sulfonic acid dimethylamide | 1-(4-chloro-benzyl)-2-(1-phenoxy-ethyl)-6-piperazin-1-yl-1H-benzoimidazole and dimethylaminosulfamoyl chloride (commercially available) | 554.4 |
| 52 | 586.2 | 6-(4-benzenesulfonyl-piperazin-1-yl)-1-(4-chloro-benzyl)-2-(1-phenoxy-ethyl)-1H-benzoimidazole | 1-(4-chloro-benzyl)-2-(1-phenoxy-ethyl)-6-piperazin-1-yl-1H-benzoimidazole and benzenesulfonyl chloride (commercially available) | 587.4 |
| 53 | 600.2 | 1-(4-chloro-benzyl)-2-(1-phenoxy-ethyl)-6-(4-phenylmethanesulfonyl-piperazin-1-yl)-1H-benzoimidazole | 1-(4-chloro-benzyl)-2-(1-phenoxy-ethyl)-6-piperazin-1-yl-1H-benzoimidazole and phenyl-methanesulfonyl chloride (commercially available) | 601.3 |
| 54 | 600.2 | 1-(4-chloro-benzyl)-2-(1-phenoxy-ethyl)-6-[4-(toluene-2-sulfonyl)-piperazin-1-yl]-1H-benzoimidazole | 1-(4-chloro-benzyl)-2-(1-phenoxy-ethyl)-6-piperazin-1-yl-1H-benzoimidazole and 2-methylbenzenesulfonyl chloride (commercially available) | 601.3 |
| 55 | 488.2 | 1-{4-[3-(4-chloro-benzyl)-2-(1-phenoxy-ethyl)-3H-benzoimidazol-5-yl]-piperazin-1-yl}-ethanone | 1-(4-chloro-benzyl)-2-(1-phenoxy-ethyl)-6-piperazin-1-yl-1H-benzoimidazole and acetyl chloride (commercially available) | 489.4 |
| 56 | 502.2 | 1-{4-[3-(4-chloro-benzyl)-2-(1-phenoxy-ethyl)-3H-benzoimidazol-5-yl]-piperazin-1-yl}-propan-1-one | 1-(4-chloro-benzyl)-2-(1-phenoxy-ethyl)-6-piperazin-1-yl-1H-benzoimidazole and propionyl chloride (commercially available) | 503.4 |
| 57 | 544.3 | 1-{4-[3-(4-chloro-benzyl)-2-(1-phenoxy-ethyl)-3H-benzoimidazol-5-yl]-piperazin-1-yl}-hexan-1-one | 1-(4-chloro-benzyl)-2-(1-phenoxy-ethyl)-6-piperazin-1-yl-1H-benzoimidazole and hexanoyl chloride (commercially available) | 545.4 |
| 58 | 550.2 | {4-[3-(4-chloro-benzyl)-2-(1-phenoxy-ethyl)-3H-benzoimidazol-5-yl]-piperazin-1-yl}-phenyl-methanone | 1-(4-chloro-benzyl)-2-(1-phenoxy-ethyl)-6-piperazin-1-yl-1H-benzoimidazole and benzoyl chloride (commercially available) | 551.3 |
| 59 | 564.2 | {4-[3-(4-chloro-benzyl)-2-(1-phenoxy-ethyl)-3H-benzoimidazol-5-yl]-piperazin-1-yl}-o-tolyl-methanone | 1-(4-chloro-benzyl)-2-(1-phenoxy-ethyl)-6-piperazin-1-yl-1H-benzoimidazole and o-tolyl-acetyl chloride (commercially available) | 565.4 |

Example 60

Phenoxymethyl-1-(4-trifluoromethoxy-benzyl)-1H-benzoimidazole-5-carboxylic acid allyl ester Step 1:

Fluoro-3-nitro-benzoic acid allyl ester 50.6 g of 4-fluoro-3-nitrobenzoic acid were dissolved in ethanol and treated with 44.5 g of cesium carbonate. The solvent was evaporated and the resulting residue taken up in DMF. 25 ml of allylbromide were added and the resulting cesium bromide filtered off. After evaporation of the solvent and extraction from tert. butylmethyl ether/water a yellow oil resulted.

Step 2:

Nitro-4-(4-trifluoromethoxy-benzylamino)-benzoic acid allyl ester 5.0 g of 4-fluoro-3-nitro-benzoic acid allyl ester (22 mmol) were dissolved in 100 ml ethanol. 4.25 g of 4-(trifluoromethoxy)-benzylamine (22 mmol) were added and stirred at room temperature for 1 h. The product was extracted from methylenchloride/water and dried over sodium sulfate. The crude product was crystallized from isopropyl ether to result in yellow crystals (7.5 g). MS(ISP): 397.2 (M+H)+.

Step 3:

4-[tert-Butoxycarbonyl-(4-trifluoromethoxy-benzyl)-amino]-3-nitro-benzoic acid allyl ester 7.5 g of 3-nitro-4-(4-trifluoromethoxy-benzylamino)-benzoic acid allyl ester (18.9 mmol) were dissolved in 100 ml THF. 8.25 g di-tert. butyl-dicarbonate (37.8 mmol), 8 ml diisopropylethylamine (47.2 mmol) and 3.4 g dimethylaminopyridine (28.3 mmol) were added and the reaction stirred at room temperature for 16 h. The solvent was evaporated and the crude product digerated from cyclohexane to result in orange crystals which were not further characterized.

Step 4:

Amino-4-[tert-butoxycarbonyl-(4-trifluoromethoxy-benzyl)-amino]-benzoic acid allyl ester 2 g of 4-[tert-butoxycarbonyl-(4-trifluoromethoxy-benzyl)-amino]-3-nitro-benzoic acid allyl ester (4.0 mmol) were dissolved in 20 ml DMF. 2.8 g $SnCl_2 \times 2\ H_2O$ (12 mmol) are added and the reaction stirred at room temperature for 16 h. The crude was filtered over Kieselgel and the solvent evaporated. MS(ISP): 467.3 (M+H)+.

Step 5:

4-[tert-Butoxycarbonyl-(4-trifluoromethoxy-benzyl)-amino]-3-(2-phenoxy-acetylamino)-benzoic acid allyl ester 318 mg of phenoxyacetic acid were dissolved in methylenchloride and 0.36 ml of diisopropylcarbodiimide added. 950 mg of 3-amino-4-[tert-butoxycarbonyl-(4-trifluoromethoxy-benzyl)-amino]-benzoic acid allylester were added and the reaction mixture stirred at room temperature for 16 h. The product was extracted from methylenchloride/water without further characterization.

Step 6:

1-(4-Methoxy-benzyl)-2-phenoxymethyl-1H-benzoimidazole-5-carboxylic acid allyl ester Crude 4-[tert-butoxycarbonyl-(4-trifluoromethoxy-benzyl)-amino]-3-(2-phenoxy-acetylamino)-benzoic acid allyl ester was dissolved in methanol and 4N HCl in dioxan added. The reaction was stirred at 40° C. for 16 h. The crude material was purified via reversed phase preparative HPLC. MS(ISP): 483.3 (M+H)⁺.

Example 61

Phenoxymethyl-1-(4-trifluoromethoxy-benzyl)-1H-benzoimidazole-5-carboxylic acid butyl-amide Step 1:

2-Phenoxymethyl-1-(4-trifluoromethoxy-benzyl)-1H-benzoimidazole-5-carboxylic acid 0.6 g of 1-(4-methoxy-benzyl)-2-phenoxymethyl-1H-benzoimidazole-5-carboxylic acid allyl ester were dissolved in methylenchloride. 55 mg of tetrakis(triphenylphosphine)palladium(0) and 1 ml of morpholine were added and stirred at room temperature for 1 h. The product was extracted from methylenechloride/water. MS(ISP): 441.1 (M−H)⁻.

Step 2:

2-Phenoxymethyl-1-(4-trifluoromethoxy-benzyl)-1H-benzoimidazole-5-carboxylic acid butyl-amide 0.16 mmol of 2-phenoxymethyl-1-(4-trifluoromethoxy-benzyl)-1H-benzoimidazole-5-carboxylic acid were dissolved in 1 ml THF with 1 eq. DIC. After 15 min 1.5 eq of butylamine was added and the reaction stirred at room temperature for 16 h. The crude material was purified via reversed phase preparative HPLC. MS(ISP) 498.3 (M+H)⁺.

Example 62

2-Phenoxymethyl-1-(4-trifluoromethoxy-benzyl)-1H-benzoimidazole-5-carboxylic acid cyclopropylamide 0.16 mmol of 2-phenoxymethyl-1-(4-trifluoromethoxy-benzyl)-1H-benzoimidazole-5-carboxylic acid were dissolved in 1 ml THF with 1 eq. DIC. After 15 min 1.5 eq of cyclopropylamine was added and the reaction stirred at room temperature for 16 h. The crude material was purified via reversed phase preparative HPLC. MS(ISP): 482.4 (M+H)⁺.

Example 63

2-Phenoxymethyl-1-(4-trifluoromethoxy-benzyl)-1H-benzoimidazole-5-carboxylic acid [2-(3-methoxy-phenyl)-ethyl]-amide 0.16 mmol of 2-phenoxymethyl-1-(4-trifluoromethoxy-benzyl)-1H-benzoimidazole-5-carboxylic acid were dissolved in 1 ml THF with 1 eq. DIC. After 15 min 1.5 eq of 3-methoxyphenethylamine were added and the reaction stirred at room temperature for 16 h. The crude material was purified via reversed phase preparative HPLC. MS(ISP): 576.3 (M+H)⁺.

Example 64

2-Phenoxymethyl-1-(4-trifluoromethoxy-benzyl)-1H-benzoimidazole-5-carboxylic acid [2-(3-trifluoromethyl-phenyl)-ethyl]-amide 0.16 mmol of 2-phenoxymethyl-1-(4-trifluoromethoxy-benzyl)-1H-benzoimidazole-5-carboxylic acid were dissolved in 1 ml THF with 1 eq. DIC. After 15 min 1.5 eq of 3-trifluoromethylphenethylamine were added and the reaction stirred at room temperature for 16 h. The crude material was purified via reversed phase preparative HPLC MS(ISP): 614.6 (M+H)⁺.

Example 65

2-Phenoxymethyl-1-(4-trifluoromethoxy-benzyl)-1H-benzoimidazole-5-carboxylic acid pentylamide 0.16 mmol of 2-phenoxymethyl-1-(4-trifluoromethoxy-benzyl)-1H-benzoimidazole-5-carboxylic acid were dissolved in 1 ml THF with 1 eq. DIC. After 15 min 1.5 eq of n-pentylamine were added and the reaction stirred at room temperature for 16 h. The crude material was purified via reversed phase preparative HPLC. MS(ISP): 512.3 (M+H)⁺.

Example 66

2-Phenoxymethyl-1-(4-trifluoromethoxy-benzyl)-1H-benzoimidazole-5-carboxylic acid (2,2-dimethyl propyl)-amide

0.16 mmol of 2-phenoxymethyl-1-(4-trifluoromethoxy-benzyl)-1H-benzoimidazole-5-carboxylic acid were dissolved in 1 ml THF with 1 eq. DIC. After 15 min 1.5 eq of 2,2-dimethylpropylamine were added and the reaction stirred at room temperature for 16 h. The crude material was purified via reversed phase preparative HPLC. MS(ISP): 512.3 $(M+H)^+$.

Example 67

2-Phenoxymethyl-1-(4-trifluoromethoxy-benzyl)-1H-benzoimidazole-5-carboxylic acid allylamide

0.16 mmol of 2-phenoxymethyl-1-(4-trifluoromethoxy-benzyl)-1H-benzoimidazole-5-carboxylic acid were dissolved in 1 ml THF with 1 eq. DIC. After 15 min 1.5 eq of allylamine were added and the reaction stirred at room temperature for 16 h. The crude material was purified via reversed phase preparative HPLC. MS(ISP): 482.2 $(M+H)^+$.

Example 68

2-Phenoxymethyl-1-(4-trifluoromethoxy-benzyl)-1H-benzoimidazole-5-carboxylic acid (3-butoxy-propyl)-amide

0.16 mmol of 2-phenoxymethyl-1-(4-trifluoromethoxy-benzyl)-1H-benzoimidazole-5-carboxylic acid were dissolved in 1 ml THF with 1 eq. DIC. After 15 min 1.5 eq of 3-butoxypropylamine were added and the reaction stirred at room temperature for 16 h. The crude material was purified via reversed phase preparative HPLC. MS(ISP): 556.3 $(M+H)^+$.

Example 69

2-Phenoxymethyl-1-(4-trifluoromethoxy-benzyl)-1H-benzoimidazole-5-carboxylic acid (naphthalen-1-ylmethyl)-amide

0.16 mmol of 2-phenoxymethyl-1-(4-trifluoromethoxy-benzyl)-1H-benzoimidazole-5-carboxylic acid were dissolved in 1 ml THF with 1 eq. DIC. After 15 min 1.5 eq of naphthalen-1-ylmethyl-amine were added and the reaction stirred at room temperature for 16 h. The crude material was purified via reversed phase preparative HPLC. MS(ISP): 582.3 $(M+H)^+$.

Example 70

2-Phenoxymethyl-1-(4-trifluoromethoxy-benzyl)-1H-benzoimidazole-5-carboxylic acid 4-trifluoromethoxy-benzylamide

0.16 mmol of 2-phenoxymethyl-1-(4-trifluoromethoxy-benzyl)-1H-benzoimidazole-5-carboxylic acid were dissolved in 1 ml THF with 1 eq. DIC. After 15 min 1.5 eq of 4-trifluormethoxy-benzylamine were added and the reaction stirred at room temperature for 16 h. The crude material was purified via reversed phase preparative HPLC. MS(ISP): 616.3 $(M+H)^+$.

Example 71

2-Phenoxymethyl-1-(4-trifluoromethoxy-benzyl)-1H-benzoimidazole-5-carboxylic acid 2-trifluoromethyl-benzylamide

0.16 mmol of 2-phenoxymethyl-1-(4-trifluoromethoxy-benzyl)-1H-benzoimidazole-5-carboxylic acid were dissolved in 1 ml THF with 1 eq. DIC. After 15 min 1.5 eq of 2-trifluoromethyl-benzylamine were added and the reaction stirred at room temperature for 16 h. The crude material was purified via reversed phase preparative HPLC. MS(ISP): 600.3 $(M+H)^+$.

Example 72

2-Phenoxymethyl-1-(4-trifluoromethoxy-benzyl)-1H-benzoimidazole-5-carboxylic acid hexylamide

0.16 mmol of 2-phenoxymethyl-1-(4-trifluoromethoxy-benzyl)-1H-benzoimidazole-5-carboxylic acid were dissolved in 1 ml THF with 1 eq. DIC. After 15 min 1.5 eq of hexylamine were added and the reaction stirred at room temperature for 16 h. The crude material was purified via reversed phase preparative HPLC. MS(ISP): 526.3 $(M+H)^+$.

Example 73

2-Phenoxymethyl-1-(4-trifluoromethoxy-benzyl)-1H-benzoimidazole-5-carboxylic acid heptylamide

0.16 mmol of 2-phenoxymethyl-1-(4-trifluoromethoxy-benzyl)-1H-benzoimidazole-5-carboxylic acid were dissolved in 1 ml THF with 1 eq. DIC. After 15 min 1.5 eq of heptylamine were added and the reaction stirred at room temperature for 16 h. The crude material was purified via reversed phase preparative HPLC. MS(ISP): 540.3 $(M+H)^+$.

Example 74

2-Phenoxymethyl-1-(4-trifluoromethoxy-benzyl)-1H-benzoimidazole-5-carboxylic acid 2,4-difluoro-benzylamide

0.16 mmol of 2-phenoxymethyl-1-(4-trifluoromethoxy-benzyl)-1H-benzoimidazole-5-carboxylic acid were dissolved in 1 ml THF with 1 eq. DIC. After 15 min 1.5 eq of 2,4-difluoro-benzylamine were added and the reaction stirred at room temperature for 16 h. The crude material was purified via reversed phase preparative HPLC. MS(ISP): 568.3 $(M+H)^+$.

Example 75

2-Phenoxymethyl-1-(4-trifluoromethoxy-benzyl)-1H-benzoimidazole-5-carboxylic acid 4-methoxy-benzylamide

0.16 mmol of 2-phenoxymethyl-1-(4-trifluoromethoxy-benzyl)-1H-benzoimidazole-5-carboxylic acid were dissolved in 1 ml THF with 1 eq. DIC. After 15 min 1.5 eq of 4-methoxy-benzylamine were added and the reaction stirred at room temperature for 16 h. The crude material was purified via reversed phase preparative HPLC. MS(ISP): 562.3 (M+H)⁺.

Example 76

2-Phenoxymethyl-1-(4-trifluoromethoxy-benzyl)-1H-benzoimidazole-5-carboxylic acid N'-pyridin-2-yl-hydrazide 0.16 mmol of 2-phenoxymethyl-1-(4-trifluoromethoxy-benzyl)-1H-benzoimidazole-5-carboxylic acid were dissolved in 1 ml THF with 1 eq. DIC. After 15 min 1.5 eq of N'-pyridin-2-yl-hydrazine were added and the reaction stirred at room temperature for 16 h. The crude material was purified via reversed phase preparative HPLC. MS(ISP): 534.2 (M+H)⁺.

Example 77

1-{4-[6-Fluoro-2-phenoxymethyl-3-(4-trifluoromethoxy-benzyl)-3H-benzoimidazol-5-yl]-piperazin-1-yl}-ethanone 80 mg of 5-fluoro-2-phenoxymethyl-6-piperazin-1-yl-1-(4-trifluoromethoxy-benzyl)-1H-benzoimidazole (0.16 mmol) and 0.033 ml TEA (0.24 mmol) were dissolved in 1.5 ml dichloromethane and treated with 0.0145 ml acetylchloride (0.2 mmol). After 5 h stirring at rt, the reaction mixture was diluted with dichloromethane, washed with water, saturated sodium bicarbonate and brine, dried with magnesium sulfate, filtered and concentrated in vacuo, leading to 85 mg yellow solid (98%). MS (ISP) 543.3 (M+H)⁺.

Preparation of 5-fluoro-2-phenoxymethyl-6-piperazin-1-yl-1-(4-trifluoromethoxy-benzyl)-1H-benzoimidazole To a suspension of 12.5 g 1,2,4-trifluoro-5-nitro-benzene (70.6 mmol) and 10.25 g potassium carbonate (74.1 mmol) in 280 ml DMF was added a solution of 14.1 g of piperazine-1-carboxylic acid tert-butyl ester (74.1 mmol) in 70 ml DMF bei keeping the temperature between −2 and 2° C. At the end of the addition, which took 30 minutes, the reaction mixture was further stirred at the same temperature for additional 15 minutes, followed by 1 h at rt. The precipitated salt was removed by filtration and the DMF solution was concentrated in vacuo. The residue was stirred with 200 ml diethylether/hexane 1:1, filtered and dried in high-vacuo, leading to 16.37 g of 4-(2,5-difluoro-4-nitro-phenyl)-piperazine-1-carboxylic acid tert-butyl ester (66.8%) as a yellow solid. MS(ISP) 361.3 (M+NH₄)⁺.

8 g of 4-(2,5-difluoro-4-nitro-phenyl)-piperazine-1-carboxylic acid tert-butyl ester (23 mmol) and 3.82 g potassium carbonate (27.65 mmol) were suspended in 80 ml DMF under stirring and then treated dropwise within 10 min with a solution of 5.29 g of 4-trifluoromethoxy-benzylamine (27.65 mmol) in 30 ml DMF. The reaction mixture was then stirred for 48 h at rt, diluted with 500 ml dichloromethane and 1 liter of water. After separation, the organic phase was washed with brine (500 ml). The two aqueous phases were then reextracted with 2×250 ml dichloromethane. The combined organic phases were dried over magnesium sulfate, filtered and concentrated in vacuo. The solid residue was stirred with 150 ml heptane/ethylacetate 4:1. After 10 minutes the suspension was diluted with 100 ml heptane, and after additional 10 min stirring, filtered. After drying in vacuo, 9.5 g of 4-[2-fluoro-4-nitro-5-(4-trifluoromethoxy-benzylamino)-phenyl]-piperazine-1-carboxylic acid tert-butyl ester was obtained as a yellow solid (80%). MS(ISP): 515.3 (M+H)⁺.

5.1 g of 4-[2-fluoro-4-nitro-5-(4-trifluoromethoxy-benzylamino)-phenyl]-piperazine-1-carboxylic acid tert-butyl ester (9.9 mmol) and 8.4 g of zinc powder (128.7 mmol) were suspended in 200 ml methanol and treated under stirring with 100 ml saturated aqueous ammonium chloride and refluxed for 45 minutes. The reaction mixture was cooled down to rt and the zinc salts eliminated by filtration and heavily washed with methanol. The methanolic solutions were combined and concentrated in vacuo, the residue was diluted with ethylacetate/water. The organic phases were separated, washed twice with water, once with brine and dried over magnesium sulfate. After filtration the solvent was removed in vacuo and the residue was dried under high vacuum, leading to 4.8 g of 4-[4-amino-2-fluoro-5-(4-trifluoromethoxy-benzylamino)-phenyl]-piperazine-1-carboxylic acid tert-butyl ester as a red foam, directly used in the next step.

4.8 g of 4-[4-amino-2-fluoro-5-(4-trifluoromethoxy-benzylamino)-phenyl]-piperazine-carboxylic acid tert-butyl ester (9.9 mmol) and 3.2 g of 1-ethoxy-2-phenoxy-1-ethaniminium chloride (14.9 mmol, CAS Registry-No. 67386-33-8) were suspended in 105 ml dioxane and 35 ml conc acetic acid and refluxed for 2 h. The solvents were removed in vacuo and the residue taken up in water/ethylacetate. Concentrated ammonium hydroxide was then added until the pH was basic. The organic phases were washed twice with water and once with brine, dried over magnesium sulfate, filtered and concentrated in vacuo. The residue was purified by column chromatography (310 g silicagel, ethylacetate/heptane 1:1) leading to 4.6 g of 4-[6-fluoro-2-phenoxymethyl-3-(4-trifluoromethoxy-benzyl)-3H-benzoimidazol-5-yl]-piperazine-1-carboxylic acid tert-butyl ester as a yellow solid (76%). MS(ISP): 600.1 (M+H)⁺.

4.6 g of 4-[6-fluoro-2-phenoxymethyl-3-(4-trifluoromethoxy-benzyl)-3H-benzoimidazol-5-yl]-piperazine-1-carboxylic acid tert-butyl ester (7.6 mmol) were stirred in 51 ml trifluoroacetic acid (661 mmol) for 2 h at rt. The reaction mixture was diluted with 500 ml water and the pH adjusted to 8 with solid sodium bicarbonate. The mixture was extracted twice with ethyl acetate and the combined organic phases were washed with brine, dried over magnesium sulfate, filtered and concentrated in vacuo. The residue was then suspended in 70 ml water, the pH adjusted to 9 with ammonium hydroxide, extracted with ethylacetate, washed with water and brine, dried over magnesium sulfate, filtered and concentrated in vacuo., leading to 3.67 g of 5-fluoro-2-phenoxymethyl-6-piperazin-1-yl-1-(4-trifluoromethoxy-benzyl)-1H-benzoimidazole as a light yellow solid (95%). MS(ISP): 500.3 (M+H)⁺.

Example 78

{4-[6-Fluoro-2-phenoxymethyl-3-(4-trifluoromethoxy-benzyl)-3H-benzoimidazol-5-yl]-piperazin-1-yl}-phenyl-methanone 80 mg of 5-fluoro-2-phenoxymethyl-6-piperazin-1-yl-1-(4-trifluoromethoxy-benzyl)-1H-benzoimidazole (0.16 mmol) and 0.033 ml TEA (0.24 mmol) were dissolved in 1.5 ml dichloromethane and treated with 0.023 ml benzoylchloride (0.2 mmol). After 4 h of stirring at rt, the reaction mixture was diluted with dichloromethane, washed with water, saturated sodium bicarbonate and brine, dried with magnesium sulfate, filtered and concentrated in vacuo, leading to 85 mg yellow solid which was purified by column chromatography (10 g silicagel, dichloromethane/methanol 30:1). 71 mg product as a light yellow solid (73%) was obtained. MS (ISP) 605.3 (M+H)$^+$.

Preparation of 5-fluoro-2-phenoxymethyl-6-piperazin-1-yl-1-(4-trifluoromethoxy-benzyl)-1H-benzoimidazole: as described in example 77.

Example 79

{4-[6-Fluoro-2-phenoxymethyl-3-(4-trifluoromethoxy-benzyl)-3H-benzoimidazol-5-yl]-piperazin-1-yl}-pyridin-4-yl-methanone 80 mg of 5-fluoro-2-phenoxymethyl-6-piperazin-1-yl-1-(4-trifluoromethoxy-benzyl)-1H-benzoimidazole (0.16 mmol) and 0.06 ml TEA (0.44 mmol) were dissolved in 1.5 ml dichloromethane and treated with 36 mg isonicotinic acid chloride hydrochloride (0.2 mmol). After 22 h of stirring at rt, the reaction mixture was diluted with dichloromethane, washed with water, saturated sodium bicarbonate and brine, dried with magnesium sulfate, filtered and concentrated in vacuo, leading to 86 mg yellow solid which was purified by column chromatography (9.5 g silicagel, dichloromethane/methanol 24:1). 46 mg product as a light yellow solid (48%) was obtained. MS (ISP) 606.3 (M+H)$^+$.

Preparation of 5-fluoro-2-phenoxymethyl-6-piperazin-1-yl-1-(4-trifluoromethoxy-benzyl)-1H-benzoimidazole: as described in example 77.

Example 80

{4-[3-(4-Chloro-benzyl)-6-fluoro-2-phenoxymethyl-3H-benzoimidazol-5-yl]-piperazin-1-yl}-cyclopropyl-methanone 72 mg of 1-(4-chloro-benzyl)-5-fluoro-2-phenoxymethyl-6-piperazin-1-yl-1H-benzoimidazole (0.16 mmol) and 0.033 ml TEA (0.24 mmol) were dissolved in 1.5 ml dichloromethane and treated with 0.0145 ml cyclopropanecarbonyl chloride (0.2 mmol). After 1.5 h of stirring at rt, the reaction mixture was diluted with dichloromethane, washed with water, saturated sodium bicarbonate and brine, dried with magnesium sulfate, filtered and concentrated in vacuo, leading to 82 mg white solid (98%). MS (ISP) 519.3 (M+H)$^+$.

Preparation of 1-(4-chloro-benzyl)-5-fluoro-2-phenoxymethyl-6-piperazin-1-yl-1H-benzoimidazole:

To a suspension of 12.5 g of 1,2,4-trifluoro-5-nitro-benzene (70.6 mmol) and 10.25 g of potassium carbonate (74.1 mmol) in 280 ml DMF was added a solution of 14.1 g of piperazine-1-carboxylic acid tert-butyl ester (74.1 mmol) in 70 ml DMF by keeping the temperature between −2 and 2° C. At the end of the addition, which took 30 minutes, the reaction mixture was further stirred at the same temperature for additional 15 minutes, followed by 1 h at rt. The precipitated salt was removed by filtration and the DMF solution was concentrated in vacuo. The residue was stirred with 200 ml diethylether/hexane 1:1, filtered and dried in high-vacuo, leading to 16.37 g of 4-(2,5-difluoro-4-nitro-phenyl)-piperazine-1-carboxylic acid tert-butyl ester (66.8%) as a yellow solid. MS(ISP) 361.3 (M+NH$_4$)$^+$.

8 g of 4-(2,5-difluoro-4-nitro-phenyl)-piperazine-1-carboxylic acid tert-butyl ester (23 mmol) and 3.82 g of potassium carbonate (27.65 mmol) were suspended in 80 ml DMF under stirring and then treated dropwise within 10 min with a solution of 3.56 ml of 4-chloro-benzylamine (27.65 mmol) in 30 ml DMF. The reaction mixture was then stirred for 28 h at rt, diluted with 500 ml 1 liter water and extracted twice with 500 ml dichloromethane and once with 250 ml dichloromethane. The combined organic phases were washed with brine (500 ml). The two aqueous phases were then reextracted with 2×250 ml dichloromethane. The combined organic phases were dried over magnesium sulfate, filtered and concentrated in vacuo. The solid residue was stirred with 150 ml heptane/ethylacetate 4:1. After 10 minutes the suspension was diluted with 100 ml heptane, and after additional 10 min stirring, filtered. After drying in high vacuo, 8.8 g 4-[5-(4-Chloro-benzylamino)-2-fluoro-4-nitro-phenyl]-piperazine-1-carboxylic acid tert-butyl ester as a yellow solid (77%) are obtained. MS(ISP): 465.4 (M+H)$^+$.

4.6 g of 4-[5-(4-chloro-benzylamino)-2-fluoro-4-nitro-phenyl]-piperazine-1-carboxylic acid tert-butyl ester (9.9 mmol) and 8.4 g of zinc powder (128.7 mmol) were suspended in 200 ml methanol and treated under stirring with 100 ml saturated aqueous ammonium chloride and refluxed for 45 minutes. The reaction mixture was cooled down to rt and the zinc salts eliminated by filtration and heavily washed with methanol. The methanolic solutions were combined and concentrated in vacuo, the residue was diluted with ethylacetate/water. The organic phases were separated, washed twice with water, once with brine and dried over magnesium sulfate. After filtration the solvent was removed in vacuo and the residue was dried under high vacuo, leading to 4.4 g of 4-[4-amino-5-(4-chloro-benzylamino)-2-fluoro-phenyl]-piperazine-1-carboxylic acid tert-butyl ester as a dark brown foam, directly used in the next step.

4.3 g of 4-[4-amino-5-(4-chloro-benzylamino)-2-fluoro-phenyl]-piperazine-1-carboxylic acid tert-butyl ester (9.9 mmol) and 3.2 g 1-ethoxy-2-phenoxy-1-ethaniminium chloride (14.9 mmol, CAS Registry No. 67386-33-8) were suspended in 105 ml dioxane and 35 ml conc. acetic acid and refluxed for 2 h. The solvents were removed in vacuo and the residue taken up in water/ethylacetate. Conc. ammonium hydroxide was then added until the pH was basic. The organic phases were washed twice with water and once with brine, dried over magnesium sulfate, filtered and concentrated in vacuo. The residue was purified by column chromatography (300 g silicagel, ethylacetate/heptane 1:1) leading to 4.2 g 4-[3-(4-chloro-benzyl)-6-fluoro-2-phenoxymethyl-3H-benzoimidazol-5-yl]-piperazine-1-carboxylic acid tert-butyl ester as a yellow solid (75%). MS(ISP): 551.3 (M+H)$^+$.

4.2 g of 4-[3-(4-chloro-benzyl)-6-fluoro-2-phenoxymethyl-3H-benzoimidazol-5-yl]-piperazine-1-carboxylic acid tert-butyl ester (7.6 mmol) were stirred in 50 ml trifluoroacetic acid (651 mmol) for 2 h at rt. The reaction mixture was diluted with 500 ml water and the pH adjusted to 8 with solid sodium bicarbonate and then to 9-10 with ammonium hydroxide, extracted with ethylacetate, washed with water and brine, dried over magnesium sulfate, filtered and concentrated in vacuo, leading to 3.34 g of 1-(4-chloro-benzyl)-5-fluoro-2-phenoxymethyl-6-piperazin-1-yl-1H-benzoimidazole as a light yellow solid (99%). MS(ISP): 451.2 (M+H)$^+$.

Example 81

{4-[3-(4-Chloro-benzyl)-6-fluoro-2-phenoxymethyl-3H-benzoimidazol-5-yl]-piperazin-1-yl}-phenyl-methanone 72 mg of 1-(4-chloro-benzyl)-5-fluoro-2-phenoxymethyl-6-piperazin-1-yl-1H-benzoimidazole (0.16 mmol) and 0.033 ml TEA (0.24 mmol) were dissolved in 1.5 ml dichloromethane and treated with 0.023 ml benzoylchloride (0.2 mmol). After 1.5 h of stirring at rt, the reaction mixture was diluted with dichloromethane, washed with water, saturated sodium bicarbonate and brine, dried with magnesium sulfate, filtered and concentrated in vacuo, leading to 84 mg residue which was purified by column chromatography (9 g silicagel, ethylacetate/heptane 2:1). 69 mg product as a light yellow solid (98%) was obtained. MS (ISP) 555.3 (M+H)$^+$.

Preparation of 1-(4-chloro-benzyl)-5-fluoro-2-phenoxymethyl-6-piperazin-1-yl-1H-benzoimidazole: as described in example 80.

Example 82

1-{4-[3-(4-Chloro-benzyl)-6-fluoro-2-phenoxymethyl-3H-benzoimidazol-5-yl]-piperazin-1-yl}-pentan-1-one 72 mg of 1-(4-chloro-benzyl)-5-fluoro-2-phenoxymethyl-6-piperazin-1-yl-1H-benzoimidazole (0.16 mmol) and 0.033 ml TEA (0.24 mmol) were dissolved in 1.5 ml dichloromethane and treated with 0.024 ml pentanoyl chloride (0.2 mmol). After 1.5 h stirring at rt, the reaction mixture was diluted with dichloromethane, washed with water, saturated sodium bicarbonate and brine, dried with magnesium sulfate, filtered and concentrated in vacuo, leading to 84 mg product as a light yellow solid (98%). MS (ISP) 535.3 (M+H)$^+$.

Preparation of 1-(4-chloro-benzyl)-5-fluoro-2-phenoxymethyl-6-piperazin-1-yl-1-yl-1H-benzoimidazole: as described in example 80.

Example 83

Cyclopropyl-{4-[6-fluoro-2-phenoxymethyl-3-(4-trifluoromethoxy-benzyl)-3H-benzoimidazol-5-yl]-piperazin-1-yl}-methanone 80 mg of 5-fluoro-2-phenoxymethyl-6-piperazin-1-yl-1-(4-trifluoromethoxy-benzyl)-1H-benzoimidazole (0.16 mmol) and 0.033 ml TEA (0.24 mmol) were dissolved in 1.5 ml dichloromethane and treated with 0.019 ml cyclopropanecarbonyl chloride (0.2 mmol). After 2 h stirring at rt, the reaction mixture was diluted with dichloromethane, washed with water, saturated sodium bicarbonate and brine, dried with magnesium sulfate, filtered and concentrated in vacuo, leading to 89 mg yellow solid (98%). MS (ISP) 569.4 (M+H)$^+$.

Preparation of 5-fluoro-2-phenoxymethyl-6-piperazin-1-yl-1-(4-trifluoromethoxy-benzyl)-1H-benzoimidazole: as described in example 77.

Example 84

1-{4-[6-Fluoro-2-phenoxymethyl-3-(4-trifluoromethoxy-benzyl)-3H-benzoimidazol-5-yl]-piperazin-1-yl}-pentan-1-one 80 mg of 5-fluoro-2-phenoxymethyl-6-piperazin-1-yl-1-(4-trifluoromethoxy-benzyl)-1H-benzoimidazole (0.16 mmol) and 0.033 ml TEA (0.24 mmol) were dissolved in 1.5 ml dichloromethane and treated with 0.025 ml pentanoyl chloride (0.2 mmol). After 2 h stirring at rt, the reaction mixture was diluted with dichloromethane, washed with water, saturated sodium bicarbonate and brine, dried with magnesium sulfate, filtered and concentrated in vacuo, leading to 89 mg yellow solid (93%). MS (ISP) 585.3 (M+H)$^+$.

Preparation of 5-fluoro-2-phenoxymethyl-6-piperazin-1-yl-1-(4-trifluoromethoxy-benzyl)-1H-benzoimidazole: as described in example 77.

Example 85

1-{4-[6-Fluoro-2-phenoxymethyl-3-(4-trifluoromethoxy-benzyl)-3H-benzoimidazol-5-yl]-piperazin-1-yl}-propan-1-one 80 mg of 5-fluoro-2-phenoxymethyl-6-piperazin-1-yl-1-(4-trifluoromethoxy-benzyl)-1H-benzoimidazole (0.16 mmol) and 0.033 ml TEA (0.24 mmol) were dissolved in 1.5 ml dichloromethane and treated with 0.018 ml propionyl chloride (0.2 mmol). After 2 h stirring at rt, the reaction mixture was diluted with dichloromethane, washed with water, saturated sodium bicarbonate and brine, dried with magnesium sulfate, filtered and concentrated in vacuo, leading to 87 mg yellow solid (98%). MS (ISP) 557.2 (M+H)$^+$.

Preparation of 5-fluoro-2-phenoxymethyl-6-piperazin-1-yl-1-(4-trifluoromethoxy-benzyl)-1H-benzoimidazole: as described in example 77.

Example 86

1-{4-[6-Fluoro-2-phenoxymethyl-3-(4-trifluoromethoxy-benzyl)-3H-benzoimidazol-5-yl]-piperazin-1-yl}-2-phenyl-ethanone 80 mg of 5-fluoro-2-phenoxymethyl-6-piperazin-1-yl-1-(4-trifluoromethoxy-benzyl)-1H-benzoimidazole (0.16 mmol) and 0.033 ml TEA (0.24 mmol) were dissolved in 1.5 ml dichloromethane and treated with 0.027 ml phenyl-acetyl chloride (0.2 mmol). After 5 h stirring at rt, the reaction mixture was diluted with dichloromethane, washed with water, saturated sodium bicarbonate and brine, dried with magnesium sulfate, filtered and concentrated in vacuo, leading to 89 mg light yellow solid (86%). MS (ISP) 619.4 (M+H)$^+$.

Preparation of 5-fluoro-2-phenoxymethyl-6-piperazin-1-yl-1-(4-trifluoromethoxy-benzyl)-1H-benzoimidazole: as described in example 77.

Example 87

1-{4-[6-Fluoro-2-phenoxymethyl-3-(4-trifluoromethoxy-benzyl)-3H-benzoimidazol-5-yl]-piperazin-1-yl}-butan-1-one 80 mg of 5-fluoro-2-phenoxymethyl-6-piperazin-1-yl-1-(4-trifluoromethoxy-benzyl)-1H-benzoimidazole (0.16 mmol) and 0.033 ml TEA (0.24 mmol) were dissolved in 1.5 ml dichloromethane and treated with 0.021 ml butyryl chloride (0.2 mmol). After 5 h stirring at rt, the reaction mixture was diluted with dichloromethane, washed with water, saturated sodium bicarbonate and brine, dried with magnesium sulfate, filtered and concentrated in vacuo, leading to 88 mg of light yellow solid (97%). MS (ISP) 571.3 (M+H)$^+$.

Preparation of 5-fluoro-2-phenoxymethyl-6-piperazin-1-yl-1-(4-trifluoromethoxy-benzyl)-1H-benzoimidazole: as described in example 77.

Example 88

{4-[6-Fluoro-2-phenoxymethyl-3-(4-trifluoromethoxy-benzyl)-3H-benzoimidazol-5-yl]-piperazin-1-yl}-o-tolyl-methanone 80 mg of 5-fluoro-2-phenoxymethyl-6-piperazin-1-yl-1-(4-trifluoromethoxy-benzyl)-1H-benzoimidazole (0.16 mmol) and 0.033 ml TEA (0.24 mmol) were dissolved in 1.5 ml dichloromethane and treated with 0.026 ml 2-Methylbenzoyl chloride (0.2 mmol). After 5 h stirring at rt, the reaction mixture was diluted with dichloromethane, washed with water, saturated sodium bicarbonate and brine, dried with magnesium sulfate, filtered and concentrated in vacuo, leading to 74 mg light yellow solid (73%). MS (ISP) 619.4 (M+H)$^+$.

Preparation of 5-fluoro-2-phenoxymethyl-6-piperazin-1-yl-1-(4-trifluoromethoxy-benzyl)-1H-benzoimidazole: described in example 77.

Example 89

1-{4-[6-Fluoro-2-phenoxymethyl-3-(4-trifluoromethoxy-benzyl)-3H-benzoimidazol-5-yl]-piperazin-1-yl}-3-methoxy-propan-1-one 0.020 ml 3-methoxy-propionic acid (0.2 mmol) and 40 mg 1,1-carbonyldiimidazole (0.24 mmol) were refluxed in 4 ml dichloromethane under nitrogen for 40 minutes. 100 mg of 5-fluoro-2-phenoxymethyl-6-piperazin-1-yl-1-(4-trifluoromethoxy-benzyl)-1H-benzoimidazole (0.2 mmol) were added and the resulting mixture refluxed for additional 4.5 h. The reaction mixture was then diluted with dichloromethane, washed with water, saturated sodium bicarbonate and brine, dried with magnesium sulfate, filtered and concentrated in vacuo, leading to 129 mg yellow solid. This residue was purified by column chromatography (40 g silicagel, dichloromethane/methanol 24:1) leading to 44 mg off-white solid (37%). MS (ISP) 587.2 (M+H)$^+$.

Preparation of 5-fluoro-2-phenoxymethyl-6-piperazin-1-yl-1-(4-trifluoromethoxy-benzyl)-1H-benzoimidazole: as described in example 77.

Example 90

1-{4-[3-(4-chloro-benzyl)-6-fluoro-2-phenoxymethyl-3H-benzoimidazol-5-yl]-piperazin-1-yl}-ethanone 72 mg of 1-(4-chloro-benzyl)-5-fluoro-2-phenoxymethyl-6-piperazin-1-yl-1H-benzoimidazole (0.16 mmol) and 0.033 ml TEA (0.24 mmol) were dissolved in 1.5 ml dichloromethane and treated with 0.0145 ml acetylchloride (0.2 mmol). After 1.5 h stirring at rt, the reaction mixture was diluted with dichloromethane, washed with water, saturated sodium bicarbonate and brine, dried with magnesium sulfate, filtered and concentrated in vacuo, leading to 68 mg of an off-white solid (84%). MS (ISP) 493.3 (M+H)$^+$.

Preparation of 1-(4-chloro-benzyl)-5-fluoro-2-phenoxymethyl-6-piperazin-1-yl-1H-benzoimidazole: described in example 80.

Example 91

1-{4-[3-(4-Chloro-benzyl)-6-fluoro-2-phenoxymethyl-3H-benzoimidazol-5-yl]-piperazin-1-yl}-propan-1-one 72 mg of 1-(4-chloro-benzyl)-5-fluoro-2-phenoxymethyl-6-piperazin-1-yl-1H-benzoimidazole (0.16 mmol) and 0.033 ml TEA (0.24 mmol) were dissolved in 1.5 ml dichloromethane and treated with 0.018 ml propionyl chloride (0.2 mmol). After 1.5 h stirring at rt, the reaction mixture was diluted with dichloromethane, washed with water, saturated sodium bicarbonate and brine, dried with magnesium sulfate, filtered and concentrated in vacuo, leading to 79 mg of a light brown solid (96%). MS (ISP) 507.3 (M+H)$^+$.

Preparation of 1-(4-chloro-benzyl)-5-fluoro-2-phenoxymethyl-6-piperazin-1-yl-1H-benzoimidazole: as described in example 80.

Example 92

1-{4-[3-(4-Chloro-benzyl)-6-fluoro-2-phenoxymethyl-3H-benzoimidazol-5-yl]-piperazin-1-yl}-butan-1-one 72 mg of 1-(4-chloro-benzyl)-5-fluoro-2-phenoxymethyl-6-piperazin-1-yl-1H-benzoimidazole (0.16 mmol) and 0.033 ml TEA (0.24 mmol) were dissolved in 1.5 ml dichloromethane and treated with 0.0145 ml 0.021 ml butyryl chloride (0.2 mmol). After 1.5 h stirring at rt, the reaction mixture was diluted with dichloromethane, washed with water, saturated sodium bicarbonate and brine, dried with magnesium sulfate, filtered and concentrated in vacuo, leading to 79 mg of a light red solid (94%). MS (ISP) 521.3 (M+H)$^+$.

Preparation of 1-(4-chloro-benzyl)-5-fluoro-2-phenoxymethyl-6-piperazin-1-yl-1H-benzoimidazole: described in example 80.

Example 93

2-Cyclopropyl-1-{4-[6-fluoro-2-phenoxymethyl-3-(4-trifluoromethoxy-benzyl)-3H-benzoimidazol-5-yl]-piperazin-1-yl}-ethanone 0.020 ml of cyclopropyl-acetic acid (0.2 mmol) and 40 mg of 1,1-carbonyldiimidazole (0.24 mmol) were refluxed in 4 ml dichloromethane under nitrogen for 40 minutes. 100 mg 5-Fluoro-2-phenoxymethyl-6-piperazin-1-yl-1-(4-trifluoromethoxy-benzyl)-1H-benzoimidazole (0.2 mmol) were added and the resulting mixture refluxed for additional 26 h. The reaction mixture was then diluted with dichloromethane, washed with water, saturated sodium bicarbonate and brine, dried with magnesium sulfate, filtered and concentrated in vacuo, leading to 129 mg yellow solid. This residue was purified by column chromatography (24 g silicagel, dichloromethane/methanol 24:1) leading to 77 mg light yellow solid (63%). MS (ISP) 583.3 (M+H)$^+$.

Preparation of 5-fluoro-2-phenoxymethyl-6-piperazin-1-yl-1-(4-trifluoromethoxy-benzyl)-1H-benzoimidazole: as described in example 77.

Example 94

1-{4-[3-(4-Chloro-benzyl)-6-fluoro-2-phenoxymethyl-3H-benzoimidazol-5-yl]-piperazin-1-yl}-2-phenyl-ethanone 72 mg of 1-(4-chloro-benzyl)-5-fluoro-2-phenoxymethyl-6-piperazin-1-yl-1H-benzoimidazole (0.16 mmol) and 0.033 ml TEA (0.24 mmol) were dissolved in 1.5 ml dichloromethane and treated with 0.027 ml phenyl-acetyl chloride (0.2 mmol). After 22 h stirring at reflux, the reaction mixture was diluted with dichloromethane, washed with water, saturated sodium bicarbonate and brine, dried with magnesium sulfate, filtered and concentrated in vacuo, leading to 90 mg of a light brown solid (94%). MS (ISP) 469.3 (M+H)$^+$.

Preparation of 1-(4-chloro-benzyl)-5-fluoro-2-phenoxymethyl-6-piperazin-1-yl-1H-benzoimidazole: as described in example 80.

Example 95

1-{4-[3-(4-Chloro-benzyl)-6-fluoro-2-phenoxymethyl-3H-benzoimidazol-5-yl]-piperazin-1-yl}-2-cyclopropyl-ethanone 71 mg of TBTU (0.22 mmol), 0.19 ml of ethyldiisopropylamine and 0.022 ml of cyclopropyl-acetic acid were dissolved in 6 ml DMF and stirred for one minute at rt under argon. Then 100 mg of 1-(4-chloro-benzyl)-5-fluoro-2-phenoxymethyl-6-piperazin-1-yl-1H-benzoimidazole (0.22 mmol) were added and the reaction mixture was stirred for 22 h at rt. The reaction mixture was then diluted with 30 ml water and extracted with ethylacetate (twice). The combined organic phases were washed with water and brine, dried with magnesium sulfate, filtered and concentrated in vacuo, leading to 130 mg of a light red solid (100%). MS (ISP) 533.4 $(M+H)^+$.

Preparation of 1-(4-chloro-benzyl)-5-fluoro-2-phenoxymethyl-6-piperazin-1-yl-1H-benzoimidazole: as described in example 80.

Example 96

1-{4-[3-(4-Chloro-benzyl)-6-fluoro-2-phenoxymethyl-3H-benzoimidazol-5-yl]-piperazin-1-yl}-3-methoxy-propan-1-one 71 mg of TBTU (0.22 mmol), 0.19 ml of ethyldiisopropylamine and 0.023 ml of 3-methoxy-propionic acid (0.22 mmol) were dissolved in 6 ml DMF and stirred for one minute at rt under argon. Then 100 mg of 1-(4-chloro-benzyl)-5-fluoro-2-phenoxymethyl-6-piperazin-1-yl-1H-benzoimidazole (0.22 mmol) were added and the reaction mixture was stirred for 22 h at rt. The reaction mixture was then diluted with 30 ml water and extracted with ethylacetate (twice). The combined organic phases were washed with water and brine, dried with magnesium sulfate, filtered and concentrated in vacuo, leading to 121 mg of a light red solid (97%). MS (ISP) 537.4 $(M+H)^+$.

Preparation of 1-(4-chloro-benzyl)-5-fluoro-2-phenoxymethyl-6-piperazin-1-yl-1H-benzoimidazole: described in example 80.

Intermediate 1

2-Phenoxymethyl-1H-indole-5-carboxylic acid methyl ester

Step 1: Resin Bound 4-Amino-3-iodo-benzoic acid methyl ester 16.3 g of 4-amino-3-iodo-benzoic acid methyl ester were added to a suspension of 10 g of tosylchloride resin (loading: 1.97 meq/g) in pyridine and the reaction was stirred at 50° C. for 16 h. The resin was subsequently washed with methylenchloride and isopropanol.

Step 2: Resin Bound 2-Phenoxymethyl-1H-indole-5-carboxylic acid methyl ester

Resin bound 4-amino-3-iodo-benzoic acid methyl ester was suspended in DMF and treated with 15.6 g of phenyl propargylether, 60 ml of triethylamine and catalytic amounts of CuI and bis(triphenylphosphine)palladium(II) chloride. The resin was shaken for 6 h at 50° C. and washed subsequently with DMF, isopropanol/water and diethylether.

Step 3: 2-Phenoxymethyl-1H-indole-5-carboxylic acid methyl ester

The resin was treated with 1M TBAF/THF at 70° C. for 5 h. The filtrate was evaporated and the product extracted from ethylacetate/water. MS(ISP): 282.3 $(M+H)^+$.

Example 97

2-Phenoxymethyl-1-(4-trifluoromethylsulfanyl-benzyl)-1H-indole-5-carboxylic acid butylamide Step 1:

2-Phenoxymethyl-1-(4-trifluoromethylsulfanyl-benzyl)-1H-indole-5-carboxylic acid methyl ester 30 mg of 2-phenoxymethyl-1H-indole-5-carboxylic acid methyl ester were dissolved in 1 ml of THF and treated with 5 mg NaH (60%) at 0° C. for 15 min. 1.2 eq. of 1-bromomethyl-4-trifluoromethylsulfanyl-benzene were added and the reaction stirred for 1.5 h. The solvent was evaporated and the product extracted from methylenchloride/water. The product was purified by preparative HPLC. MS(ISP): 472.5 $(M+H)^+$.

Step 2:

2-Phenoxymethyl-1-(4-trifluoromethylsulfanyl-benzyl)-1H-indole-5-carboxylic acid 2-Phenoxymethyl-1-(4-trifluoromethylsulfanyl-benzyl)-1H-indole-5-carboxylic acid methyl ester was dissolved in dioxane and treated with 1M NaOH at 50° C. for 16 h. The solvents were evaporated and the remaining solid treated with 0.5 ml HCl/1 ml ethylacetate and extracted with water.

Step 3:

2-Phenoxymethyl-1-(4-trifluoromethylsulfanyl-benzyl)-1H-indole-5-carboxylic acid butylamide 2-Phenoxymethyl-1-(4-trifluoromethylsulfanyl-benzyl)-1H-indole-5-carboxylic acid was dissolved in methylenchloride. 1 eq. of DIPEA, HOBT and butylamine were added. 1 eq of EDCI was added at 0° C. and the reaction stirred at 25° C. for 16 h. The reaction was quenched with water and the organic phase evaporated. The product was purified by preparative HPLC. MS(ISP): 513.1 $(M+H)^+$.

According to the procedure described for the synthesis of example 1 further indole-derivatives have been synthesized from 2-phenoxymethyl-1H-indole-5-carboxylic acid methyl ester as indicated in table 3. The results are compiled in table 1 and comprise example 98 to example 145.

TABLE 3

| No. | MW | Name | Starting materials | $(M+H)^+$ found |
|---|---|---|---|---|
| 98 | 482.5 | 1-(2-fluoro-4-trifluoromethyl-benzyl)-2-phenoxymethyl-1H-indole-5-carboxylic acid cyclopropylamide | 2-phenoxymethyl-1H-indole-5-carboxylic acid, cyclopropylamine and 1-bromomethyl-2-fluoro-4-trifluoromethyl-benzene | 483.1 |

TABLE 3-continued

| No. | MW | Name | Starting materials | (M + H)+ found |
|---|---|---|---|---|
| 99 | 498.9 | 1-(2-chloro-5-trifluoromethyl-benzyl)-2-phenoxymethyl-1H-indole-5-carboxylic acid cyclopropylamide | 2-phenoxymethyl-1H-indole-5-carboxylic acid, cyclopropylamine and 1-bromomethyl-2-chloro-5-trifluoromethyl-benzene | 499.1 |
| 100 | 505.6 | 1-(2-difluoromethoxy-benzyl)-2-phenoxymethyl-1H-indole-5-carboxylic acid piperidin-1-ylamide | 2-phenoxymethyl-1H-indole-5-carboxylic acid, piperidin-1-ylamine and 1-bromomethyl-2-difluoro-methoxy-benzene | 506.2 |
| 101 | 496.5 | 2-phenoxymethyl-1-(4-trifluoromethoxy-benzyl)-1H-indole-5-carboxylic acid butylamide | 2-phenoxymethyl-1H-indole-5-carboxylic acid, butylamine and 1-bromomethyl-4-trifluoromethoxy-benzene | 497.2 |
| 102 | 442.6 | 1-(4-methoxy-benzyl)-2-phenoxymethyl-1H-indole-5-carboxylic acid butylamide | 2-phenoxymethyl-1H-indole-5-carboxylic acid, butylamine and 1-bromomethyl-4-methoxy-benzene | 443.2 |
| 103 | 512.6 | 2-phenoxymethyl-1-(2-trifluoromethylsulfanyl-benzyl)-1H-indole-5-carboxylic acid butylamide | 2-phenoxymethyl-1H-indole-5-carboxylic acid, butylamine and 1-bromomethyl-2-trifluoromethylsulfanyl-benzene | 513.1 |
| 104 | 462.5 | 1-(4-difluoromethoxy-benzyl)-2-phenoxy-methyl-1H-indole-5-carboxylic acid cyclopropylamide | 2-phenoxymethyl-1H-indole-5-carboxylic acid, cyclopropylamine and 1-bromomethyl-4-difluoro-methoxy-benzene | 463.2 |
| 105 | 523.6 | 2-phenoxymethyl-1-(2-trifluoromethoxy-benzyl)-1H-indole-5-carboxylic acid piperidin-1-ylamide | 2-phenoxymethyl-1H-indole-5-carboxylic acid, piperidin-1-ylamine and 1-bromomethyl-2-trifluoro-methoxy-benzene | 524.2 |
| 106 | 523.6 | 2-phenoxymethyl-1-(3-trifluoromethoxy-benzyl)-1H-indole-5-carboxylic acid piperidin-1-ylamide | 2-phenoxymethyl-1H-indole-5-carboxylic acid, piperidin-1-ylamine and 1-bromomethyl-3-trifluoro-methoxy-benzene | 524.2 |
| 107 | 498.5 | 1-(2-fluoro-5-trifluoro-methyl-benzyl)-2-phenoxymethyl-1H-indole-5-carboxylic acid butylamide | 2-phenoxymethyl-1H-indole-5-carboxylic acid, butylamine and 2-bromomethyl-1-fluoro-4-trifluoromethyl-benzene | 499.2 |
| 108 | 480.5 | 2-phenoxymethyl-1-(4-trifluoromethyl-benzyl)-1H-indole-5-carboxylic acid butylamide | 2-phenoxymethyl-1H-indole-5-carboxylic acid, butylamine and 1-bromomethyl-4-trifluoromethyl-benzene | 481.2 |
| 109 | 512.6 | 2-phenoxymethyl-1-(3-trifluoromethylsulfanyl-benzyl)-1H-indole-5-carboxylic acid butylamide | 2-phenoxymethyl-1H-indole-5-carboxylic acid, butylamine and 1-bromomethyl-3-trifluoromethylsulfanyl-benzene | 513.1 |
| 110 | 539.6 | 2-phenoxymethyl-1-(4-trifluoromethylsulfanyl-benzyl)-1H-indole-5-carboxylic acid piperidin-1-ylamide | 2-phenoxymethyl-1H-indole-5-carboxylic acid, piperidin-1-ylamine and 1-bromomethyl-4-trifluoro-methylsulfanyl-benzene | 540.1 |
| 111 | 448.5 | 1-(2,5-difluoro-benzyl)-2-phenoxymethyl-1H-indole-5-carboxylic acid butylamide | 2-phenoxymethyl-1H-indole-5-carboxylic acid, butylamine and 2-bromomethyl-1,4-difluoro-benzene | 449.2 |
| 112 | 450.5 | 2-phenoxymethyl-1-(2,4,5-trifluoro-benzyl)-1H-indole-5-carboxylic acid cyclopropylamide | 2-phenoxymethyl-1H-indole-5-carboxylic acid, cyclopropylamine and 1-bromomethyl-2,4,5-trifluoro-benzene | 451.1 |
| 113 | 462.5 | 1-(3-difluoromethoxy-benzyl)-2-phenoxy-methyl-1H-indole-5-carboxylic acid cyclopropylamide | 2-phenoxymethyl-1H-indole-5-carboxylic acid, cyclopropylamine and 1-bromomethyl-3-difluoro-methoxy-benzene | 463.1 |
| 114 | 498.5 | 1-(2-fluoro-4-trifluoromethyl-benzyl)-2-phenoxymethyl-1H-indole-5-carboxylic acid butylamide | 2-phenoxymethyl-1H-indole-5-carboxylic acid, butylamine and 1-bromomethyl-2-fluoro-4-trifluoromethyl-benzene | 499.1 |

TABLE 3-continued

| No. | MW | Name | Starting materials | (M + H)+ found |
|---|---|---|---|---|
| 115 | 413.5 | 2-phenoxymethyl-1-pyridin-2-ylmethyl-1H-indole-5-carboxylic acid butylamide | 2-phenoxymethyl-1H-indole-5-carboxylic acid, butylamine and 2-bromomethyl-pyridine | 414.2 |
| 116 | 514.9 | 1-(2-chloro-5-trifluoromethyl-benzyl)-2-phenoxymethyl-1H-indole-5-carboxylic acid butylamide | 2-phenoxymethyl-1H-indole-5-carboxylic acid, butylamine and 2-bromomethyl-1-chloro-4-trifluoromethyl-benzene | 515.1 |
| 117 | 462.5 | 1-(2-difluoromethoxy-benzyl)-2 phenoxymethyl-1H-indole-5-carboxylic acid cyclopropylamide | 2-phenoxymethyl-1H-indole-5-carboxylic acid, cyclopropylamine and 1-bromomethyl-2-difluoro-methoxy-benzene | 463.1 |
| 118 | 478.5 | 1-(4-difluoromethoxy-benzyl)-2-phenoxy-methyl-1H-indole-5-carboxylic acid butylamide | 2-phenoxymethyl-1H-indole-5-carboxylic acid, butylamine and 1-bromomethyl-4-difluoromethoxy-benzene | 479.2 |
| 119 | 448.5 | 1-(3,5-difluoro-benzyl)-2-phenoxymethyl-1H-indole-5-carboxylic acid butylamide | 2-phenoxymethyl-1H-indole-5-carboxylic acid, butylamine and 1-bromomethyl-3,5-difluoro-benzene | 449.2 |
| 120 | 480.5 | 2-phenoxymethyl-1-(2-trifluoromethoxy-benzyl)-1H-indole-5-carboxylic acid cyclopropylamide | 2-phenoxymethyl-1H-indole-5-carboxylic acid, cyclopropylamine and 1-bromomethyl-2-trifluoro-methoxy-benzene | 481.2 |
| 121 | 480.5 | 2-phenoxymethyl-1-(3-trifluoromethoxy-benzyl)-1H-indole-5-carboxylic acid cyclopropylamide | 2-phenoxymethyl-1H-indole-5-carboxylic acid, cyclopropylamine and 1-bromomethyl-3-trifluoro-methoxy-benzene | 481.1 |
| 122 | 496.6 | 2-phenoxymethyl-1-(4-trifluoromethylsulfanyl-benzyl)-1H-indole-5-carboxylic acid cyclopropylamide | 2-phenoxymethyl-1H-indole-5-carboxylic acid, cyclopropylamine and 1-bromomethyl-4-trifluoromethyl-sulfanyl-benzene | 497.1 |
| 123 | 525.5 | 1-(2-fluoro-4-trifluoromethyl-benzyl)-2-phenoxymethyl-1H-indole-5-carboxylic acid piperidin-1-ylamide | 2-phenoxymethyl-1H-indole-5-carboxylic acid, piperidin-1-yl-amine and 1-bromomethyl-2-fluoro-4-trifluoromethyl-benzene | 526.1 |
| 124 | 463.6 | 2-phenoxymethyl-1-quinolin-8-ylmethyl-1H-indole-5-carboxylic acid butylamide | 2-phenoxymethyl-1H-indole-5-carboxylic acid, butylamine and 8-bromomethyl-quinoline | 464.2 |
| 125 | 480.5 | 2-phenoxymethyl-1-(4-trifluoromethoxy-benzyl)-1H-indole-5-carboxylic acid cyclopropylamide | 2-phenoxymethyl-1H-indole-5-carboxylic acid, cyproylamine and 1-bromomethyl-4-trifluoro-methoxy-benzene | 481.1 |
| 126 | 426.5 | 1-(4-methoxy-benzyl)-2-phenoxymethyl-1H-indole-5-carboxylic acid cyclopropylamide | 2-phenoxymethyl-1H-indole-5-carboxylic acid, cyproylamine and 1-bromomethyl-4-methoxy-benzene | 427.2 |
| 127 | 496.6 | 2-phenoxymethyl-1-(2-trifluoromethylsulfanyl-benzyl)-1H-indole-5-carboxylic acid cyclopropylamide | 2-phenoxymethyl-1H-indole-5-carboxylic acid, cyproylamine and 1-bromomethyl-2-trifluoro-methylsulfanyl-benzene | 497.1 |
| 128 | 466.5 | 2-phenoxymethyl-1-(2,4,5-trifluoro-benzyl)-1H-indole-5-carboxylic acid butylamide | 2-phenoxymethyl-1H-indole-5-carboxylic acid, butylamine and 1-bromomethyl-2,4,5-trifluoro-benzene | 467.2 |
| 129 | 482.5 | 1-(2-fluoro-5-trifluoromethyl-benzyl)-2-phenoxymethyl-1H-indole-5-carboxylic acid cyclopropylamide | 2-phenoxymethyl-1H-indole-5-carboxylic acid, cyclopropylamine and 2-bromomethyl-1-fluoro-4-trifluoromethyl-benzene | 483.1 |
| 130 | 464.5 | 2-phenoxymethyl-1-(4-trifluoromethyl-benzyl)-1H-indole-5-carboxylic acid cyclopropylamide | 2-phenoxymethyl-1H-indole-5-carboxylic acid, cyclopropylamine and 2-bromomethyl-3-trifluoromethyl-benzene | 465.1 |

TABLE 3-continued

| No. | MW | Name | Starting materials | (M + H)+ found |
|---|---|---|---|---|
| 131 | 478.5 | 1-(2-difluoromethoxy-benzyl)-2-phenoxymethyl-1H-indole-5-carboxylic acid butylamide | 2-phenoxymethyl-1H-indole-5-carboxylic acid, butylamine and 1-bromomethyl-2-difluoromethoxy-benzene | 479.2 |
| 132 | 494.5 | 1-(4-methoxy-3-trifluoromethyl-benzyl)-2-phenoxymethyl-1H-indole-5-carboxylic acid cyclopropylamide | 2-phenoxymethyl-1H-indole-5-carboxylic acid, cyclopropylamine and 4-bromomethyl-1-methoxy-2-trifluoromethyl-benzene | 495.1 |
| 133 | 496.5 | 2-phenoxymethyl-1-(2-trifluoromethoxy-benzyl)-1H-indole-5-carboxylic acid butylamide | 2-phenoxymethyl-1H-indole-5-carboxylic acid, butylamine and 1-bromomethyl-2-trifluoromethoxy-benzene | 497.1 |
| 134 | 496.5 | 2-phenoxymethyl-1-(3-trifluoromethoxy-benzyl)-1H-indole-5-carboxylic acid butylamide | 2-phenoxymethyl-1H-indole-5-carboxylic acid, butylamine and 1-bromomethyl-3-trifluoromethoxy-benzene | 497.2 |
| 135 | 432.5 | 1-(2,5-Difluoro-benzyl)-2-phenoxymethyl-1H-indole-5-carboxylic acid cyclopropylamide | 2-phenoxymethyl-1H-indole-5-carboxylic acid, cyclopropylamine and 2-bromomethyl-1,4-difluoro-benzene | 433.1 |
| 136 | 450.5 | 2-Phenoxymethyl-1-(2,3,4-trifluoro-benzyl)-1H-indole-5-carboxylic acid cyclopropylamide | 2-phenoxymethyl-1H-indole-5-carboxylic acid, cyclopropylamine and 1-bromomethyl-2,3,4-trifluoro-benzene | 451.1 |
| 137 | 505.6 | 1-(3-difluoromethoxy-benzyl)-2-phenoxymethyl-1H-indole-5-carboxylic acid piperidin-1-ylamide | 2-phenoxymethyl-1H-indole-5-carboxylic acid, piperidin-1-yl-amine and 1-bromomethyl-3-difluoro-methoxy-benzene | 506.1 |
| 138 | 527.6 | 2-phenoxymethyl-1-(4-trifluoromethylsulfanyl-benzyl)-1H-indole-5-carboxylic acid N-butyl-hydrazide | 2-phenoxymethyl-1H-indole-5-carboxylic acid, butylhydrazine and 1-bromomethyl-4-trifluoro-methylsulfanyl-benzene | 528.2 |
| 139 | 511.6 | 2-phenoxymethyl-1-(4-trifluoromethoxy-benzyl)-1H-indole-5-carboxylic acid N-butyl-hydrazide | 2-phenoxymethyl-1H-indole-5-carboxylic acid, butylhydrazine and 1-bromomethyl-4-trifluoromethoxy-benzene | 512.2 |
| 140 | 527.6 | 2-phenoxymethyl-1-(3-trifluoromethylsulfanyl-benzyl)-1H-indole-5-carboxylic acid N-butyl-hydrazide | 2-phenoxymethyl-1H-indole-5-carboxylic acid, butylhydrazine and 1-bromomethyl-3-trifluoro-methylsulfanyl-benzene | 528.1 |
| 141 | 493.6 | 1-(3-difluoromethoxy-benzyl)-2-phenoxy-methyl-1H-indole-5-carboxylic acid N-butyl-hydrazide | 2-phenoxymethyl-1H-indole-5-carboxylic acid, butylhydrazine and 1-bromomethyl-3-difluoro-methoxy-benzene | 494.2 |
| 142 | 493.6 | 1-(2-difluoromethoxy-benzyl)-2-phenoxy-methyl-1H-indole-5-carboxylic acid N-butyl-hydrazide | 2-phenoxymethyl-1H-indole-5-carboxylic acid, butylhydrazine and 1-bromomethyl-2-difluoro-methoxy-benzene | 494.2 |
| 143 | 511.4 | 2-phenoxymethyl-1-(2-trifluoromethoxy-benzyl)-1H-indole-5-carboxylic acid N-butyl-hydrazide | 2-phenoxymethyl-1H-indole-5-carboxylic acid, butylhydrazine and 1-bromomethyl-2-trifluoromethoxy-benzene | 512.2 |
| 144 | 511.5 | 2-phenoxymethyl-1-(3-trifluoromethoxy-benzyl)-1H-indole-5-carboxylic acid N-butyl-hydrazide | 2-phenoxymethyl-1H-indole-5-carboxylic acid, butylhydrazine and 1-bromomethyl-3-trifluoromethoxy-benzene | 512.2 |
| 145 | 539.9 | 1-(2-chloro-5-trifluoromethyl-benzyl)-2-phenoxymethyl-1H-indole-5-carboxylic acid N-butyl-hydrazide | 2-phenoxymethyl-1H-indole-5-carboxylic acid, butylhydrazine and 2-bromomethyl-1-chloro-4-trifluoromethyl-benzene | 530.1 |

Example 146

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aq. solution/suspension of the above mentioned film coat.

Example 147

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 148

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

Example 149

The following tests were carried out in order to determine the activity of the compounds of formula I.

The affinity of the compounds of the invention for cannabinoid CB1 receptors was determined using membrane preparations of human embryonic kidney (HEK) cells in which the human cannabis CB1 receptor is transiently transfected using the Semliki Forest Virus system in conjunction with [3H]-CP-55,940 as radioligand. After incubation of a freshly prepared cell membrane preparation with the [3H]-ligand, with or without addition of compounds of the invention, separation of bound and free ligand was performed by filtration over glass-fiber filters. Radioactivity on the filter was measured by liquid scintillation counting.

The affinity of the compounds of the invention for cannabinoid CB2 receptors was determined using membrane preparations of human embryonic kidney (HEK) cells in which the human cannabis CB2 receptor is transiently transfected using the Semliki Forest virus system in conjunction with [3H]-CP-55,940 as radioligand. After incubation of a freshly prepared cell membrane preparation with the [3H]-ligand, with or without addition of compounds of the invention, separation of bound of bound and free ligand was performed by filtration over glassfiber filters. Radioactivity on the filter was measured by liquid scintillation counting.

The cannabinoid CB1 antagonistic activity of compounds of the invention was determined by functional studies using CHO cells in which human cannabinoid CB1 receptors are stably expressed (see M. Rinaldi-Carmona et. al., J. Pharmacol. Exp. Ther. 278 (1996) 871). The stable expression of the human cannabinoid receptor in cell systems was first described in Nature 1990, 346, 561-564 (CB1) and Nature 1993, 365, 61-65 (CB2) respectively. Adenylyl cyclase was stimulated using forskolin and measured by quantifying the amount of accumulated cyclic AMP. Concomitant activation of CB1 receptors by CB1 receptor agonists (e.g. CP-55,940 or (R)-WIN-55212-2) can attenuate the forskolin-induced accumulation of cAMP in a concentration dependent manner. This CB1 receptor mediated response can be antagonized by CB1 receptor antagonists such as the compounds of the invention.

The compounds of formula (I) show an excellent affinity for the CB1 receptor, determined with the experimental conditions described in Devane et. al. Mol. Pharmacol. 34 (1988) 605-613. The compounds of the present invention or their pharmaceutically acceptable salts are antagonists and selective for the CB1 receptor with affinities below $IC_{50} = 2$ μM, preferably 1 nM to 100 nM.

They exhibit at least a 10 fold selectivity against the CB2 receptor.

| Compound of Example | $IC_{50}$ [μM] |
|---|---|
| 51 | 0.06 |
| 61 | 0.03 |
| 101 | 0.02 |

Example 150

Effect of CB1 Receptor Antagonist/Inverse Agonist on CP 55,940-Induced Hypothermia in NMRI Mice Animals Male NMRI mice were used in this study and were obtained from Research Consulting Company Ltd (RCC) of Füllinsdorf (Switzerland). Mice, weighing 30-31 g were used in this study. Ambient temperature is approximately 20-21° C. and relative humidity 55-65%. A 12 hours light-dark cycle is maintained in the rooms with all tests being performed during the light phase. Access to tap water and food are ad libitum.

Method

All measurements were made between 12:00 am and 5:00 pm. Mice were brought in this environment and habituated for at least two hours before the start of the experiment. They had always free access to food and water. For each dose, 8 mice were used. Rectal body temperature measurements were recorded by mean of a rectal probe (RET2 of Physitemp) and digital thermometer (Digi-sense n°8528-20 of Cole Parmer, Chicago USA). The probe was inserted about 3.5 cm in each mouse.

The body temperature was taken 15 min before administration of either Vehicle or CB1 receptor antagonist/inverse agonist. 30 or 90 min after i.p. or p.o. administration of this compound, respectively, rectal body temperature was recorded in order to evaluate any influence of the compound itself. The CB receptor agonist CP 55,940 (0.3 mg/kg) was immediately administered intravenously, then 20 min after i.v. administration of CP 55940, body temperature was again measured.

Example 151

The in vivo activity of compounds of formula (1) was assessed for their ability to regulate feeding behavior by recording food consumption in food deprived animals.

Rats were trained to have access to food for 2 h per day and were food deprived for 22 h. When they were trained under this schedule, the amount of food taken every day during these 2 h food intake session was consistent day after day.

To test the ability of compounds of formula I to decrease food intake, 8 animals were used in a cross-over study. Rats were individually housed in Plexiglas boxes with a grid on the floor and a paper was placed below the cage floor to collect any spillage. A food dispenser (becher) filled with a pre-weighed amount of food was presented to them for 2 h. At the end of the food intake session, rats returned to their home cage. Each rat was weighed before the start of the experiment and the amount of food consumed during this 2 h food intake session was recorded. Either various doses of test compound or vehicle was administered orally 60 min before the 2 h food intake session. A positive control Rimonabant (SR141716) was included in the experiment. An Anova analysis with repeated measures was used followed by a posthoc test Student Neumann-Keuls. *P<0.05 compared to Saline-treated rats.

It is to be understood that the invention is not limited to the particular embodiments of the invention described above, as variations of the particular embodiments may be made and still fall within the scope of the appended claims.

The invention claimed is:

1. A compound of the formula I:

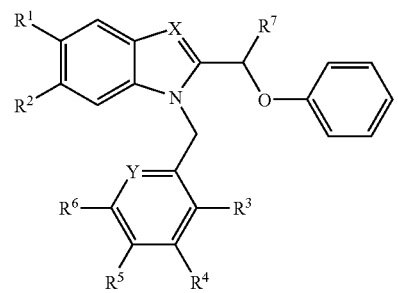

wherein
X is CH;
$R^1$ is —C(O)—NR$^8$R$^9$ or —C(O)—OR$^{10}$ and $R^2$ is hydrogen;
Y is CH;
$R^3$, $R^4$, $R^5$ and $R^6$ independently from each other are selected from the group consisting of hydrogen, halogen, lower alkoxy, lower fluoroalkyl, lower fluoroalkoxy, and lower fluoroalkylsulfanyl; or
$R^3$ and $R^4$ together with the carbon atoms they are attached to form a 5- or 6-membered unsaturated ring which may contain a heteroatom selected from the group consisting of N, O or S;
$R^7$ is hydrogen or lower alkyl;
$R^8$ is hydrogen or —NH$_2$;
$R^9$ is selected from the group consisting of lower alkyl, lower alkenyl, lower alkoxyalkyl,
—(CH$_2$)$_m$—C$_{3-7}$-cycloalkyl, —(CH$_2$)$_m$-piperidinyl,
—(CH$_2$)$_m$-phenyl, wherein the phenyl ring is unsubstituted or substituted by one or two groups selected from halogen, lower alkoxy, lower fluoroalkyl and lower fluoroalkoxy,
—(CH$_2$)$_m$-naphthyl, and
pyridylamino;
$R^{10}$ is lower alkyl or lower alkenyl; and
m is 0, 1 or 2;
or a pharmaceutically acceptable salt thereof.

2. The compound according to claim 1, wherein $R^1$ is —C(O)—NR$^8$R$^9$, $R^2$ is hydrogen and $R^8$ and $R^9$ are as defined in claim 1.

3. The compound according to claim 2, wherein $R^8$ is hydrogen and $R^9$ is selected from the group consisting of lower alkyl, lower alkenyl, lower alkoxyalkyl,
—(CH$_2$)$_m$—C$_{3-7}$-cycloalkyl, —(CH$_2$)$_m$-piperidinyl,
—(CH$_2$)$_m$-phenyl, wherein the phenyl ring is unsubstituted or substituted by one or two groups selected from halogen, lower alkoxy, lower fluoroalkyl and lower fluoroalkoxy, —(CH$_2$)$_m$-naphthyl, and pyridylamino, and m is 0, 1 or 2.

4. The compound according to claim 1, wherein $R^9$ is selected from the group consisting of lower alkyl, —(CH$_2$)$_m$—C$_{3-7}$-cycloalkyl and —(CH$_2$)$_m$-piperidinyl.

5. The compound according to claim 1, wherein $R^8$ is hydrogen and $R^9$ is selected from the group consisting of lower alkyl, —(CH$_2$)$_m$—C$_{3-7}$-cycloalkyl and —(CH$_2$)$_m$-piperidinyl and m is 0, 1 or 2.

6. The compound according to claim 1, wherein at least one of $R^3$, $R^4$, $R^5$ and $R^6$ is Selected from the group consisting of halogen, lower alkoxy, lower fluoroalkyl, lower fluoroalkoxy, and lower fluoroalkylsulfanyl; or wherein $R^3$ and $R^4$ together with the carbon atoms they are attached to form a 5- or 6-membered unsaturated ring which may contain a heteroatom selected from the group consisting of N, O or S.

7. The compound according to claim 1, wherein $R^5$ is selected from the group consisting of halogen, lower alkoxy, lower fluoroalkyl, lower fluoroalkoxy, and lower fluoroalkylsulfanyl and $R^3$, $R^4$ and $R^6$ are hydrogen.

8. The compound according to claim 1, wherein $R^3$ is selected from the group consisting of halogen, lower alkoxy, lower fluoroalkyl, lower fluoroalkoxy, and lower fluoroalkylsulfanyl and $R^4$, $R^5$ and $R^6$ are hydrogen.

9. The compound according to claim 1, wherein $R^4$ is selected from the group consisting of halogen, lower alkoxy, lower fluoroalkyl, lower fluoroalkoxy, and lower fluoroalkylsulfanyl and $R^3$, $R^5$ and $R^6$ are hydrogen.

10. The compound according to claim 1, wherein $R^7$ is hydrogen or methyl.

11. The compound according to claim 1, selected from the group consisting of:

2-phenoxymethyl-1-(4-trifluoromethylsulfanyl-benzyl)-1H-indole-5-carboxylic acid butylamide, 1-(2-chloro-5-trifluoromethyl-benzyl)-2-phenoxymethyl-1H-indole-5-carboxylic acid cyclopropylamide, 2-phenoxymethyl-1-(4-trifluoromethoxy-benzyl)-1H-indole-5-carboxylic acid butylamide, 1-(4-methoxy-benzyl)-2-phenoxymethyl-1H-indole-5-carboxylic acid butylamide, 2-phenoxymethyl-1-(2-trifluoromethoxy-benzyl)-1H-indole-5-carboxylic acid piperidin-1-ylamide, 2-phenoxymethyl-1-(3-trifluoromethylsulfanyl-benzyl)-1H-indole-5-carboxylic acid butylamide, 2-phenoxymethyl-1-(2-trifluoromethoxy-benzyl)-1H-indole-5-carboxylic acid cyclopropylamide, 2-phenoxymethyl-1-(4-trifluoromethylsulfanyl-benzyl)-1H-indole-5-carboxylic acid cyclopropylamide, 2-phenoxymethyl-1-(4-trifluoromethoxy-benzyl)-1H-indole-5-carboxylic acid cyclopropylamide, and 2-phenoxymethyl-1-(2-trifluoromethoxy-benzyl)-1H-indole-5-carboxylic acid butylamide, or a pharmaceutically acceptable salt thereof.

12. A pharmaceutical composition, comprising a therapeutically effective amount of a compound according to claim 1 and a pharmaceutically acceptable carrier and/or adjuvant.

* * * * *